(12) United States Patent
Hoerr et al.

(10) Patent No.: US 11,421,038 B2
(45) Date of Patent: Aug. 23, 2022

(54) RNA-CODED ANTIBODY

(75) Inventors: Ingmar Hoerr, Tübingen (DE); Jochen Probst, Wolfschlugen (DE); Steve Pascolo, Zurich (CH)

(73) Assignee: CureVac AG, Tübingen (DE)

( * ) Notice: Subject to any disclaimer, the term of this patent is extended or adjusted under 35 U.S.C. 154(b) by 0 days.

(21) Appl. No.: 12/522,214

(22) PCT Filed: Jan. 8, 2008

(86) PCT No.: PCT/EP2008/000081
§ 371 (c)(1),
(2), (4) Date: Jan. 4, 2010

(87) PCT Pub. No.: WO2008/083949
PCT Pub. Date: Jul. 17, 2008

(65) Prior Publication Data
US 2010/0189729 A1    Jul. 29, 2010

(30) Foreign Application Priority Data
Jan. 9, 2007  (DE) .................. 102007001370.3

(51) Int. Cl.
*A61K 39/00* (2006.01)
*C07K 16/28* (2006.01)
*C07K 16/32* (2006.01)

(52) U.S. Cl.
CPC ...... *C07K 16/2887* (2013.01); *C07K 16/2863* (2013.01); *C07K 16/32* (2013.01); *A61K 2039/53* (2013.01); *C07K 2317/24* (2013.01); *C07K 2317/56* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 4,563,510 A | 1/1986 | Ugelstad | |
| 5,316,908 A | 5/1994 | Carlson et al. | |
| 5,580,859 A | 12/1996 | Felgner et al. | |
| 5,736,137 A | 4/1998 | Anderson et al. | |
| 5,821,337 A | 10/1998 | Carter | |
| 5,851,829 A * | 12/1998 | Marasco et al. | 435/328 |
| 6,066,258 A | 5/2000 | Gjerde et al. | |
| 6,136,195 A | 10/2000 | Taylor et al. | |
| 6,156,206 A | 12/2000 | Gjerde et al. | |
| 6,214,804 B1 | 4/2001 | Felgner et al. | |
| 6,576,133 B2 | 6/2003 | Gjerde et al. | |
| 6,777,187 B2 * | 8/2004 | Makarov et al. | 435/6.12 |
| 6,960,469 B2 | 11/2005 | Leroy et al. | |
| 8,383,340 B2 | 2/2013 | Ketterer et al. | |
| 2003/0083272 A1 | 5/2003 | Wiederholt et al. | |
| 2003/0099646 A1 | 5/2003 | Serrero et al. | |
| 2003/0138419 A1 * | 7/2003 | Radic et al. | 424/143.1 |
| 2003/0153735 A1 | 8/2003 | Breece et al. | |
| 2003/0175239 A1 | 9/2003 | Margolin et al. | |
| 2004/0102389 A1 | 5/2004 | Pavco et al. | |
| 2004/0132683 A1 | 7/2004 | Felgner et al. | |
| 2004/0142885 A1 | 7/2004 | Paul et al. | |
| 2005/0011836 A1 | 1/2005 | Bidlingmeyer et al. | |
| 2005/0032730 A1 | 2/2005 | Von Der Mulbe et al. | |
| 2005/0059624 A1 | 3/2005 | Hoerr et al. | |
| 2005/0221435 A1 | 10/2005 | Acres et al. | |
| 2005/0250723 A1 | 11/2005 | Hoerr et al. | |
| 2006/0188490 A1 | 8/2006 | Hoerr et al. | |
| 2008/0025944 A1 * | 1/2008 | Hoerr et al. | 424/85.2 |
| 2008/0171711 A1 | 7/2008 | Hoerr et al. | |
| 2008/0267873 A1 | 10/2008 | Hoerr et al. | |
| 2009/0286852 A1 * | 11/2009 | Kariko et al. | 514/44 R |
| 2009/0324584 A1 | 12/2009 | Hoerr et al. | |
| 2010/0050543 A1 | 3/2010 | Greiner et al. | |
| 2010/0189729 A1 | 7/2010 | Hoerr et al. | |
| 2011/0143397 A1 | 6/2011 | Kariko et al. | |
| 2016/0185840 A1 | 6/2016 | Hoerr et al. | |

FOREIGN PATENT DOCUMENTS

| | | |
|---|---|---|
| EP | 1083232 | 3/2001 |
| EP | 1224943 | 7/2002 |
| EP | 1084246 | 9/2004 |
| EP | 1619254 | 1/2006 |
| EP | 2578685 | 4/2013 |
| EP | 2970456 | 1/2016 |
| EP | 2101823 | 11/2016 |
| EP | 3092250 | 11/2016 |
| WO | WO 1990-011092 | 10/1990 |

(Continued)

OTHER PUBLICATIONS

Campbell, Biological, 6th Edition, 2002, p. 321.*
Jana et al., Appl Microbiol. Biotechnol, 2004, 65:649-657.*
Wels et al, Biotechnology, 1992, 10(10):1128-1132.*
Albrecht et al., Cancer biotherapy & Radiopharmaceuticals, 2006, 21(4): 285-304.*
Bandbon Balenga NA et al., Bicistronic expression plasmid encoding allergen and anti-IgE single chain variable fragment antibody as a novel DNA vaccine for allergy therapy and prevention, Med Hypotheses. 2006;67(1):71-4. Epub Mar. 2, 2006.
Burke B et al., Microinjection of mRNA coding for an anti-Golgi antibody inhibits intracellular transport of a viral membrane protein, Cell. Apr. 1984;36(4):847-56., Only Abstract.

(Continued)

*Primary Examiner* — Michael D Burkhart
(74) *Attorney, Agent, or Firm* — Parker Highlander PLLC

(57) ABSTRACT

The present application describes an antibody-coding, non-modified or modified RNA and the use thereof for expression of this antibody, for the preparation of a pharmaceutical composition, in particular a passive vaccine, for treatment of tumours and cancer diseases, cardiovascular diseases, infectious diseases, auto-immune diseases, virus diseases and monogenetic diseases, e.g. also in gene therapy. The present invention furthermore describes an in vitro transcription method, in vitro methods for expression of this antibody using the RNA according to the invention and an in vivo method.

31 Claims, 27 Drawing Sheets

Specification includes a Sequence Listing.

(56) References Cited

FOREIGN PATENT DOCUMENTS

| WO | WO 1993-012814 | 7/1993 |
| --- | --- | --- |
| WO | WO 1999-014346 | 3/1999 |
| WO | WO 1999-057275 | 11/1999 |
| WO | WO 2001/055713 | 8/2001 |
| WO | WO 2003/051483 | 6/2003 |
| WO | WO 2003/059381 | 7/2003 |
| WO | WO 2003/074654 | 9/2003 |
| WO | WO-2004/085474 A2 | 10/2004 |
| WO | WO 2006024518 A1 * | 3/2006 |
| WO | WO 2006-037807 | 4/2006 |
| WO | WO 2006-116458 | 11/2006 |
| WO | WO 2006-122828 | 11/2006 |
| WO | WO 2007-024708 | 3/2007 |
| WO | WO 2008-052770 | 5/2008 |
| WO | WO 2008/083940 | 7/2008 |
| WO | WO 2008/083949 | 7/2008 |
| WO | WO 2010-037408 | 4/2010 |
| WO | WO 2010-037539 | 4/2010 |
| WO | WO 2014/152774 | 9/2014 |
| WO | WO 2015-062738 | 5/2015 |
| WO | WO 2015/105926 | 7/2015 |
| WO | WO 2016/066708 | 5/2016 |
| WO | WO 2017/201352 | 11/2017 |

OTHER PUBLICATIONS

Burks EA et al., In vitro scanning saturation mutagenesis of an antibody binding pocket, Proc Natl Acad Sci U S A. Jan. 21, 1997;94(2):412-7.

Fukuda I et al., In vitro evoluton of single-chain antibodies using mRNA display, Nucleic Acids Res. 2006;34(19):e127. Epub Sep. 29, 2006.

Hecker et al., Non-viral DNA and mRNA gene delivery to the CNS pre-operatively for neuroprotection and following neurotrauma, molecular therapy, 2004, vol. 9, p. 258.

Hoerr, Stabilized messenger RNA (RNActive™) as a tool for innovative gene delivery, Tissue Engineering, 2nd International Congress on Regenerative Biology, 9.-11.10.2006, vol. 13, No. 4, 2007, pp. 886-887.

Kitaguchi K et al., Immune deficiency enhances expression of recombinant human antibody in mice after nonviral in vivo gene transfer, Int J Mol Med. Oct. 2005;16(4):683-8.

Lesaffre B et al., Direct non-cell autonomous Pax6 activity regulates eye development in the zebrafish, Neural Dev. Jan. 17, 2007;2:2.

Pascolo S., Vaccination with messenger RNA, Methods Mol Med. 2006;127:23-40. Review.

Hu, S. et al., "Codon optimization, expression, and characterization of an internalizing anti-Erb82 single-chain antibody in Pichia pastoris." *Protein Expression and Purification* 47(1) (2006), 249-257.

Mayfield, S.P. et al., "Expression and assembly of a fully active antibody in algae." *Proceedings of the National Academy of Sciences of USA* 100(2) (2003), 438-442.

Vaquero, C. et al., "Transient expression of a tumor-specific single-chain fragment and a chimeric antibody in tobacco leaves." *Proceedings of the National Academy of Sciences of USA* 96(20) (1999), 11128-11133.

Kudla, G. et al., "High guanine and cytosine content increases mRNA levels in mammalian cells." *PLOS Biology* 4(6) (2006), e180.

Graf, M. et al., "Codon-optimized genes that enable increased heterologous excpression in mammalian cells and elicit efficient immune responses in mice after vaccination of naked DNA." *Methods in Molecular Medicine* 94 (2004), 197-210.

Khare, P.D. et al., "Tumor growth suppression by a retroviral vector displaying scFv antibody to CEA and carrying the iNOS gene." *Anticancer Research* 22 (2002), 2443-2446.

Ivanovska, N. et al., "Immunication with a DNA chimeric molecule encoding a hemagglutinin peptide and a scFv CD21-specific antibody fragment induces long-lasting IgM and CTL response to influenza virus." *Vaccine* 24(11) (2006), 1830-1837.

Ohashi, H. et al., "Efficient protein selection based on ribosome display system with purified components." *Biochemical and Biophysical Research Communications* 352(1) (2006), 270-276.

Zeytin, H.E. et al., "Construction and characterization of DNA vaccines encoding the single-chain variable fragment of the anti-idiotype antibody 1A7 mimicking the tumor-associated antigen disialoganglioside GD2." *Cancer Gene Therapy* 7(11) (2000), 1426-1436.

Carralot, J.-P. et al., "Polarization of immunity induced by direct injection of naked sequence-stabilized mRNA vaccines." *CMLS Cellular and Molecular Life Sciences* 61(18) (2004), 2418-2424.

Cree, B. et al., "Tolerability and effects of Rituximab (anti-CD20 antibhody) in neuromyelitis optica (NMO) and rapidly worsening multiple sclerosis (MS)." *Neurology* 62(7) Suppl. 5 (2004), A492.

Kolb, A.F. et al., "A virus-neutralising antibody is not cytotoxic in vitro." *Molecular Immunology* 43(6) (2006), 677-689.

Bakker, J.M. et al., "Therapeutic antibody gene transfer: An active approach to passive immunity." Molecular Therapy 10(3) (2004), 411-416.

Finger et al., "Replicating retroviral vectors mediating continuous production and secretion of therapeutic gene products from cancer cells," *Cancer Gene Ther.*, 12(5):464-474, 2005.

Hess et al., "Vaccination with mRNAs encoding tumor-associated antigens and granulocyte-macrophage colony-stimulating factor efficiently primes CTL responses, but is insufficient to overcome tolerance to a model tumor/self antigen," *Cancer Immunol Immunother.*, 55(6):672-683, 2006.

Probst et al., "Spontaneous cellular uptake of exogenous messenger RNA in vivo is nucleic acid-specific, saturable and ion dependent," *Gene Ther.*, 14(15):1175-1180, 2007.

Declaration Under 37 C.F.R. § 1.132 submitted in U.S. Appl. No. 13/709,897, filed Jul. 22, 2016.

Declaration Under 37 C.F.R. § 1.132 submitted in U.S. Appl. No. 15/007,072, filed Jul. 8, 2016.

Declaration Under 37 C.F.R. § 1.132 submitted in U.S. Appl. No. 15/015,657, filed Jul. 8, 2016.

Declaration Under 37 C.F.R. § 1.132 submitted in U.S. Appl. No. 15/015,798, filed Jul. 8, 2016.

Declaration Under 37 C.F.R. § 1.132 submitted in U.S. Appl. No. 15/053,826, filed Jul. 8, 2016.

Declaration Under 37 C.F.R. § 1.132 submitted in U.S. Appl. No. 15/053,890, filed Jul. 8, 2016.

Declaration Under 37 C.F.R. § 1.132 submitted in U.S. Appl. No. 15/067,160, filed Jul. 8, 2016.

Office Action issued in U.S. Appl. No. 13/709,897, dated Feb. 27, 2015.

Office Action issued in U.S. Appl. No. 13/709,897, dated Jan. 6, 2016.

Brekke and Sandlie, "Therapeutic antibodies for human diseases at the dawn of the twenty-first century," *Nat. Reviews*, 2:52-62, 2002.

Dreier et al., "T cell costimulus-independent and very efficacious inhibition of tumor growth in mice bearing subcutaneous or leukemic human B cell lymphoma xenografts by a CD19-/CD3-bispecific single-chain antibody construct," *J Immunology*, 170:4397-4402, 2003.

Goudsmit et al., "Comparison of an anti-rabies human monoclonal antibody combination with human polyclonal anti-rabies immune globulin," *The Journal of Infectious Diseases*, 193:796-801, 2006.

Office Action issued in U.S. Appl. No. 15/007,072, dated Apr. 13, 2016.

Office Action issued in U.S. Appl. No. 15/015,657, dated Apr. 8, 2016.

Office Action issued in U.S. Appl. No. 15/015,798, dated Apr. 8, 2016.

Office Action issued in U.S. Appl. No. 15/015,879, dated Apr. 8, 2016.

Office Action issued in U.S. Appl. No. 15/053,755, dated Apr. 8, 2016.

Office Action issued in U.S. Appl. No. 15/053,826, dated Apr. 13, 2016.

(56) References Cited

OTHER PUBLICATIONS

Office Action issued in U.S. Appl. No. 15/053,890, dated Apr. 8, 2016.
Office Action issued in U.S. Appl. No. 15/067,160, dated Apr. 8, 2016.
Sáez-Llorens et al., "Safety and pharmacokinetics of palivizumab therapy in children hospitalized with respiratory syncytial virus infection," *Pediatric Infect Dis. J.*, 23:707-712, 2004.
Trkola et al., "Delay of HIV-1 rebound after cessation of antiretroviral therapy through passive transfer of human neutralizing antibodies," *Nature Med.*, 11(6):615-622, 2005.
Barreau et al., "Liposome-mediated RNA transfection should be used with caution," *RNA*, 12(10):1790-1793, 2006.
Kariko et al., "mRNA is an endogenous ligand for toll-like receptor 3," *Journal of Biological Chemistry*, 279(13):12542-12550, 2004.
Pascolo, "Messenger RNA-based vaccines," *Expert Opinion on Biological Therapy*, 4(8):1285-1294, 2004.
Primus et al., "Self-reactive antibody expression by human carcinoma cells engineered with monoclonal antibody genes," *Cancer Research*, 53(14):3355-3361, 1993.
Schoonbroodt et al., "Oligonucleotide-assisted cleavage and ligation: a novel directional DNA cloning technology to capture cDNAs. Application in the construction of a human immune antibody phage-display library," *Nucleic Acids Research*, 33(9):E81, 2005.
Valle et al., "Synthesis and secretion of mouse immunoglobulin chains from Xenopus oocytes," *Nature*, 291(5813):338-340, 1981.
Wallach et al., "A high production rate of translatable IgG mRNA accounts for the amplified synthesis of IgG in myeloma cells," *European Journal of Biochemistry*, 110(2):545-554, 1980.
Willemsen et al., "A phage display selected Fab fragment with MHC class 1-restricted specificity for MAGE-A1 allows for retargeting of primary human T lymphocytes," *Gene Therapy*, 8(21):1601-1608, 2001.
"Antibody" definition from Oxford Dictionary of Biochemistry and Molecular Biology, Oxford University Press, p. 42, 2000.
"Immunoglobulin" definition from Oxford Dictionary of Biochemistry and Molecular Biology, Oxford University Press, p. 327, 2000.
"MRNA" definition from Oxford Dictionary of Biochemistry and Molecular Biology, Oxford University Press, p. 407, 2000.
"Rituxan®," prescribing information by IDEC Pharmaceuticals Corporation and Genentech, Inc., 2004.
Belizario, "Immunodeficient Mouse Models: An Overview," *The Open Immunology Journal*, 2:79-85, 2009.
Bettinger et al., "Peptide-mediated RNA delivery: a novel approach for enhanced transfection of primary and post-mitotic cells," *Nucleic Acids Research*, 29(18):3882-3891, 2001.
Bhattachary-Chatterjee et al., "Counterpoint. Cancer Vaccines: single epitope anti-idiotype vaccine versus multiple-epitope antigen vaccine," *Cancer Immunol. Immunother.* 49(3):133-141. 2000.
Biocca et al., "Expression and targeting of intracellular antibodies in mammalian cells," *The EMBO Journal*, 9(1):101-108, 1990.
Biocca et al., "Intracellular expression of anti-p21$^{ras}$ single chain Fv fragments inhibits meiotic maturation of xenopus oocytes," *Biochemical and Biophysical Research Communications*, 192(2):422-427, 1993.
Conry et al., "Characterization of a Messenger RNA polynucleotide Vaccine Vector," *Cancer Res.*, 55:1397-1400, 1995.
Deacon and Ebringer, "Post-translational modification of rat immunoglobulins synthesized in the Xenopus oocyte translation system," *Immunology*, 38:137-144, 1979.
Fang et al., "Stable antibody expression at therapeutic levels using the 2A peptide," *Nature Biotechnology*, 23(5):584-590, 2005.
Fleeton et al., "Self-Replicative RNA Vaccines Elicit Protection against Influenza A Virus, Respiratory Syncytial Virus, and a Tickborne Encephalitis Virus," *Journal of Infectious Diseases*, 183:1395-1398, 2001.
Greber and Gerace, "Nuclear Protein Import is Inhibited by an Antibody to a Lumenal Epitope of a Nuclear Pore Complex Glycoprotein," *The Journal of Cell Biology*, 116(1):15-30, 1992.

Hoerr et al., "In vivo application of RNA leads to induction of specific cytotoxic T lymphocytes and antibodies," *Eur J Immunol.*, 30:1-7, 2000.
Hotta et al., "Production of Anti-CD2 Chimeric Antibody by Recombinant Animal Cells," *J Biosci Bioeng*, 98(4):298-303. 2004.
Ito et al., "NOD/SCID/$\gamma_c^{null}$ mouse: an excellent recipient mouse model for engraftment of human cells," *Blood*, 100:3175-3182, 2002.
Jiang et al., "Gene therapy using adenovirus-mediated full-length anti-HER-2 antibody for HER-2 overexpression cancers," *Clin Cancer Res.*, 12(20):6179-6185, 2006.
Johanning et al., "A sindbis virus mRNA polynucleotide vector achieves prolonged and high level heterologous gene expression in vivo," *Nucleic Acids Research*, 23(9):1495-1501, 1995.
Kallen et al., "A novel, disruptive vaccination technology," *Human Vaccines & Immunotherapeutics*, 9:10, pp. 1-14, 2013.
Kariko et al., "Suppression of RNA Recognition by Toll-like Receptors: The Impact of Nucleoside Modification and the Evolutionary Origin of RNA," *Immunity*, 23:165-175, 2005.
Kolb and Siddell, "Expression of a Recombinant Monoclonal Antibody From a Bicistronic mRNA," *Hybridoma*, 16(5):421-426, 1997.
Leget et al., "Use of rituximab, the new FDA-approved antibody," *Current Opinion in Oncology*, 10:548-551, 1998.
Levene et al., "Therapeutic monoclonal antibodies in oncology," *Journal of the Royal Society of Medicine*, 98:146-152, 2005.
Lewis et al., "Generation of neutralizing activity against human immunodeficiency virus type 1 in serum by antibody gene transfer," *Journal of Virology*, 76(17):8769-8775, 2002.
Lin et al., "A phase I/II dose escalation study of apolizumab (Hu1D10) using a stepped-up dosing schedule in patients with chronic lymphocytic leukemia and acute leukemia," *Leukemia & Lymphoma*, 50(12):1958-1963, 2009.
Lutzky et al., "Antibody-based vaccines for the treatment of melanoma," *Seminars in Oncology*, 29(5):462-470. 2002.
Makeyev and Liebhaber, "The poly(C)-binding proteins: A multiplicity of functions and a search for mechanisms," *RNA*, 8:265-278, 2002.
Martinon et al., "Induction of virus-specific cytotoxic T lymphocytes in vivo by liposome-entrapped mRNA," *European Journal of Immunology*, 23:1719-1722, 1993.
Mielke et al., "Stabilized, long-term expression of heterodimeric proteins from tricistronic mRNA," *Gene*, 254:1-8, 2000.
Mizuguchi et al., "IRES-Dependent Second Gene Expression is Significantly Lower than Cap-Dependent First gene Expression in a Bicistronic Vector," *Mol. Ther.*, 1(4):376-382. 2000.
Mukherjee et al., "Prolonged prophylactic protection from botulism with a single adenovirus treatment promoting serum expression of a VHH-based antitoxin protein," *PLoS ONE*, 9(8):e106422, pp. 1-13, 2014.
Noel et al., "High in vivo production of a model monoclonal antibody on adenoviral gene transfer," *Human Gene Therapy*, 13:1483-1493, 2002.
Office Action issued in European Application No. 16001146.6, dated Jun. 16, 2017.
Office Action issued in U.S. Appl. No. 13/709,897, dated Aug. 10, 2017.
Office Action issued in U.S. Appl. No. 15/007,072, dated Jun. 16, 2017.
Office Action issued in U.S. Appl. No. 15/015,657, dated Jun. 16, 2017.
Office Action issued in U.S. Appl. No. 15/015,798, dated Jun. 16, 2017.
Office Action issued in U.S. Appl. No. 15/015,879, dated Jun. 30, 2017.
Office Action issued in U.S. Appl. No. 15/053,826, dated Apr. 7, 2017.
Office Action issued in U.S. Appl. No. 15/053,890, dated Jun. 16, 2017.
Office Action issued in U.S. Appl. No. 15/067,160, dated June 30, 2017.
Opposition to European Patent No. EP 2101823 by Dr. Gerhard Weinzierl, filed Aug. 23, 2017.

(56) References Cited

OTHER PUBLICATIONS

Opposition to European Patent No. EP 2101823 by eTheRNA Immunotherapies NV, filed Aug. 11, 2017.
Opposition to European Patent No. EP 2101823 by F. Hoffmann-La Roche AG, filed Aug. 17, 2017.
Opposition to European Patent No. EP 2101823 by Mathys & Squire LLP, filed Aug. 23, 2017.
Opposition to European Patent No. EP 2101823 by Moderna Therapeutics, Inc., filed Aug. 23, 2017.
Opposition to European Patent No. EP 2101823 by Strawman Limited, filed Aug. 23, 2017.
Pardi et al., "Administration of nucleoside-modified mRNA encoding broadly neutralizing antibody protects humanized mice from HIV-1 challenge," *Nature Communications*, 8:14630, 2017.
Pascolo, "Chapter 7.2: Plasmid DNA and Messenger RNA for therapy," *Handbook of Pharmaceutical Biotechnology*, John Wiley & Sons, 2007.
Pascolo, "RNA-based Therapies," In Cox (Ed.) *Drug Discovery Handbook*, 27:1259-1308. 2005.
Pelegrin et al., "Monoclonal antibody-based genetic immunotherapy," *Current Gene Therapy*, 4(3):347-356, 2004.
Perez et al., "Regulatable systemic production of monoclonal antibodies by in vivo muscle electroporation," *Genetic Vaccines and Therapy*, 2:2, 2004.
Rabinovich et al., "Synthetic messenger RNA as a tool for gene therapy," *Human Gene Therapy*, 17:1027-1035, 2006.
Rammensee, "Some consideration on the use of peptides and mRNA for therapeutic vaccination against cancer," *Immunology and Cell Biology*, 84:290-294, 2006.
Reff et al., Depletion of B cells in vivo by a chimeric mouse human monoclonal antibody to CD20, *Blood*, 83(2):435-445, 1994.
Response filed in European regional phase 08701020.3, submitted Dec. 23, 2009.
Response filed in European regional phase 08701020.3, submitted Jun. 2, 2010.
Response filed in European regional phase 08701020.3, submitted Jun. 20, 2012.
Response filed in European regional phase 08701020.3, submitted May 17, 2016.
Response filed in European regional phase 08701020.3, submitted Oct. 5, 2015.
Richardson et al., "Intrabody -mediated knockout of the high-affinity IL2 receptor in primary human T cells using abicistronic lentivirus vector," *Gene Therapy*, 5:635-644, 1998.
Rosa et al., "An Antibody against Secretogranin I (Chromogranin B) Is Packaged into Secretory Granules," *Journal of Cell Biol.*, 109:17-34, 1989.
Seiden et al., "A phase II trial of EMD72000 (matuzumab), a humanized anti-EGFR monoclonal antibody, in patients with platinum-resistant ovarian and primary peritoneal malignancies," *Gynecologic Oncology*, 104(3):727-731, 2007.
Soreq and Huez, "The biosynthesis of biologically active proteins in mRNA-microinjected xenopus oocyte," *Critical Reviews in Biochemistry*, 18(3):199-238, 1985.
Stadler et al., "Elimination of large tumors in mice by mRNA-encoded bispecific antibodies," *Nature Medicine*, 23(7):815-817, 2017.
Tamura et al., "Cellular and humoral immune response in mice, I. Development of delayed-type footpad swelling against sheep erythrocytes and its suppression by intraperitoneal administration of the antigen," *J. Med. Sci. Biol.*, 26:161-168, 1973.
Thess et al., "Sequence-engineered mRNA Without Chemical Nucleoside Modifications Enables an Effective Protein Therapy in Large Animals," *Molecular* Therapy, 23(9):1456-1464, 2015.
Thran et al., "mRNA mediates passive vaccination against infectious agents, toxins, and tumors," *EMBO Molecular Medicine*, and Appendix, e201707678, 2017.
Tjelle et al., "Monoclonal antibodies produced by muscle after plasmid injection and electroporation," *Mol Therapy*, 9(3):328-336, 2004.
Valle et al., "Anti-ovalbumin monoclonal antibodies interact with their antigen in internal membranes of *Xenopus* oocytes," *Letters to Nature*, 300:71-74, 1982.
Weide et al., "Plasmid DNA- and messenger RNA-based anti-cancer vaccination," *Immunology Letters*, 115:33-42, 2008.
Weide et al., "Results of the first phase I/II clinical vaccination trial with direct injection of mRNA," *J Immunother*, 31(2):180-188, 2008.
Wolff et al., "Direct gene transfer into mouse muscle in vivo," *Science*, 247:1465-1468, 1990.
Youn et al., "Modified mRNA as an alternative to plasmid DNA (pDNA) for transcript replacement and vaccination therapy," *Expert Opin Biol Ther.*, 15(9):1337-1348. 2015.
Anderson et al., "Incorporation of pseudouridine into mRNA enhances translation by diminishing PKR activation," *Nucleic Acids Research*, 38(17):5884-5892, 2010.
Daugherty et al., "Formulation and delivery issues for monoclonal antibody therapeutics," *Advanced Drug Delivery Reviews*, 58:686-706, 2006.
Karikó et al., "Generating the optical mRNA for therapy: HPLC purification eliminates immune activation and improves translation of nucleoside-modified protein-encoding mRNA," *Nucleic Acids Research*, 39(21):e142, 2011.
Pardi et al., "Expression kinetics of nucleoside-modified mRNA delivered in lipid nanoparticles to mice by various routes," *J Control Release*, 217:345-351, 2015.
Weissman et al., "HPLC purification of in vitro transcribed long RNA," *Methods Mol Biol.*, 969:43-54, 2013.
Gallie, "The cap and poly(A) tail function synergistically to regulate mRNA translational efficiency," *Genes Develop.*, 5(11):2108-2116, 1991.
Löffler et al., "A recombinant bispecific single-chain antibody, CD19 × CD3, indices rapid and high lymphoma-directed cytotoxicity by unstimulated T lymphocytes," *Blood*, 95(6):2098-2103, 2000.
Wittel et al., "The in vivo characteristics of genetically engineered divalent and tetravalent single-chain antibody constructs," *Nucl. Med. Biol.*, 32(2):157-164, 2005.
Alberts et al., Glossery in *Molecular Biology of the Cell*, $3^{rd}$ ed., 1994.
Anderson et al., "Incorporation of pseudouridine into mRNA enhances translation by diminishing PKR activation," *Nucleic Acids Res.*, 38(17):5884-5892, 2010.
Arazani and Hecker, "RNA analysis by ion-pair reversed-phase high performance liquid chromatography," *Nucleic Acids Res.*, 29(2):e7, 2001.
Barik and Bitko, "Prospects of RNA interference therapy in respiratory viral diseases: update 2006," *Expert Opin. Biol. Ther.*, 6(11):1151-1160, 2006.
Chow et al., "Synthesis of oligodeoxyribonucleotides on silica gel support," *Nucleic Acids Res.*, 9(12):2807-2817, 1981.
Cooper and Hausman, *The Cell: A Molecular Approach*, 2004.
Curriculum Vitae of Alexander Schwenger.
Curriculum Vitae of David Hornby.
Curriculum Vitae of Frantisek Svec.
Curriculum Vitae of Mariola Fotin-Mleczek.
Curriculum Vitae of Moritz Thran.
Declaration ($2^{nd}$) of Frantisek Svec in IPR2017-02194, U.S. Pat. No. 8,383,340, executed Jul. 18, 2018.
Declaration of Alexander Schwenger in IPR2017-02194, U.S. Pat. No. 8,383,340, executed Jul. 18, 2018.
Declaration of David Hornby in IPR2017-02194, U.S. Pat. No. 8,383,340, executed Sep. 29, 2017.
Declaration of Frantisek Svec in IPR2017-02194, U.S. Pat. No. 8,383,340, executed Jan. 18, 2018.
Declaration of Mariola Fotin-Mleczek in IPR2017-02194, U.S. Pat. No. 8,383,340, executed Jul. 18, 2018.
Declaration of Moritz Thran in IPR2017-02194, U.S. Pat. No. 8,383,340, executed Jul. 18, 2018.
Deposition of Alexander Schwenger.
Deposition of Frantisek.
Deposition of Moritz Thran.
Deposition Transcript of Dr. Hornby.

(56) References Cited

OTHER PUBLICATIONS

Deshmukh et al., "Purification of Antisense Oligonucleotides," *Methods Enzymol.*, 313:203-226, 1999.
Dickman and Hornby, "Enrichment and analysis of RNA centered on ion pair reverse phase methodology," *RNA*, 12:691-696, 2006.
Drager and Regnier, "High-Performance Anion-Exchange Chromatography of Oligonucleotides," *Anal. Biochem.*, 145:47-56, 1985.
Eeltink et al., "Advances in organic polymer-based monolithic column technologyfor high-resolution liquid chromatography-mass spectrometryprofiling of antibodies, intact proteins, oligonucleotides, and peptides", *J. Chromatogr. A*, 1498:8-21, 2017.
Ettre, "Nomenclature for Chromatography," *Pure Appl. Chem.*, 65(4):819-872, 1993.
File History for U.S. Pat. No. 8,383,340.
Gelhaus et al., "Rapid purification of RNA secondary structures", *Nucleic Acids Res.*, 31(21):e135, 2003.
Georgopoulos and Leibowitz, "Use of high-performance liquid chromatographic fractionation of large RNA molecules in the assay of group I intron ribozyme activity," *J. Chromatogr. A.*, 868:109-114, 2000.
Gjerde et al., "DNA Chromatography," 2002.
Gjerde, "RNA Separation: Substrates, Functional Groups, Mechanisms, and Control," In: *RNA Purification and Analysis: Sample Preparation, Extraction, Chromatography*, Chapter 3, pp. 37-66, 2009.
Gniadecki et al., "Trends and Developments in the Pharmacological Treatment of Psoriasis", *Acta Derm. Venereol*, 82:401-410, 2002.
Green et al., "The Role of Antisense RNA in Gene Regulation," *Ann. Rev. Biochem.*, 55:569-597, 1986.
Guillot et al., "Involvement of Toll-like Receptor 3 in the Immune Response of Lung Epithelial Cells to Double-stranded RNA and Influenza A Virus," *J. Biol. Chem.*, 280(7):5571-5580, 2005.
Haupt and Pingoud, "Comparison of several high-performance liquid chromatography techniques for the separation of oligonucleotides according to their chain lengths," *J. Chromatogr.*, 260:419-427, 1983.
Holzl et al., "Analysis of Biological and Synthetic Ribonucleic Acids by Liquid Chromatography-Mass Spectrometry Using Monolithic Capillary Columns," *Anal. Chem.*, 77:673-680, 2005.
Horvath et al., "Enhancement of Retention by Ion-Pair Formation in Liquid Chromatography with Nonpolar Stationary Phases," *Anal. Chem.*, 49(14):2295-2305, 1977.
Huber et al., "High-resolution liquid chromatography of DNA fragments on non-porous poly(styrene-divinylbenzene) particles", *Nucleic Acids Res.*, 21(5):1061-1066, 1993.
Huber et al., "Mutation detection by capillary denaturing high-performance liquid chromatography using monolithic columns," *J. Biochem. Biophys. Methods.*, 47:5-19, 2001.
Huck and Bonn, "Poly(Slyrene-Divinylbenzene) Based Media for Liquid Chromatography," *Chem. Eng. Technol.*, 28(12):1457-1472, 2005.
Huck and Bonn, "Polyslyrene/Divinylbenzene Based Monolithic and Encapsulated Capillary Columens for the Analysis of Nucleic Acids by high-Performance Liquid Chromatography-Electrospray Ionization Mass Spectrometry," *Eng. Life Sci.*, 5(5):431-435, 2005.
Isis press release 2002.
Kariko et al., "Generating the optimal mRNA for therapy: HPLC purification eliminates immune activation and improves translation of nucleoside-modified, protein-encoding mRNA," *Nucleic Acids Res.*, Advance Access, 1-10, 2011.
Kariko et al., "Incorporation of Pseudouridine Into mRNA Yields Superior Nonimmunogenic Vector With Increased Translational Capacity and Biological Stability," *Mol. Ther.*, 16(11):1833-1840, 2008.
Kieft nd Batey, "A general method for rapid and nondenaturing purification RNAs," *RNA*, 10:988-995, 2004.
Koolman and Roehm, "Color Atlas of Biochemistry," $2^{nd}$ Ed., 2005.
Kurreck "Antisense technologies: Improvement through novel chemical modifications", 270:1628-1644, 2003.
LC/GC Europe Catalogue, 17(8), 2004.
Li and Breaker, "Kinetics of RNA Degradation by Specific Base Catalysis of Transesterification Involving the 2'-Hydroxyl Group," *J. Am. Chem. Soc.*, 121:5364-5372, 1999.
Lloyd et al., "Oligonucleotide analysis by anion exchange HPLC," *Bioseparation*, 2:207-215, 1991.
Lloyd et al., "Rigid polymeries: the future of oligonucleotide analysis and purification," *J. Chromatogr. A.*, 1009:223-230, 2003.
Lloyd, "Rigid macroporous copolymers as stationary phases in high-performance liquid chromatography," *J. Chromatogr.*, 544:201-217, 1991.
Martins et al., "Ribonucleic acid purification," *J. Chromatogr. A*,1355:1-14, 2014.
Matthews and van Holde, "Chapter 4: Nucleic Acids", In:*Biochemistry*, $2^{nd}$ Edition, The Benjamin/Cummings Publishing Company, 1996.
McFarland and Borer, "Separation of o6go-RNA by reverse-phase HPLC," *Nucleic Acids Res.*, 7(4):1067-1080, 1979.
Morgan and Celebuski, "Large-scale purification of haptenated oligonucleotides using high-performance liquid chromatography," *J. Chromatogr.*, 536:85-93, 1991.
Motion to Exclude.
Nallagatla et al., "RNA structure and regulation of innate immunity through protein kinase PKR," *Curr. Opin. Struct. Biol.*, 21(1):119-127, 2011.
Neue, "Physical Properties of HPLC Packings," Chapter 4 In: *HPLC Columns: Theory, Technology, and Practice*, pp. 81-92, 1997.
Neue, "Reversed-Phase Chromatography," Chapter 10 In: *HPLC Columns Theory, Technology, and Practice*, pp. 183-216, 1997.
Neue, "Theory of Chromatography," Chapter 2 In: *HPLC Columns Theory, Technology, and Practice*, pp. 6-40, 1997.
Nguyen et al., "High-Resolution Preparative-Scale Purification of RNA Using the Prep Cell," *Anal. Biochem.*, 269:216-218, 1999.
Nielsen et al., "High-performance liquid chromatography purification of 26-bp serial analysis of gene expression ditags results in higher yields, longer concatemers, and substantial time savings," *Anal. Biochem.*, 313:128-132, 2003.
Oberacher et al., "Characterization of some physical and chromatographic properties of monolithic poly(styrene-co-divinylbenzene) columns," *J. Chromatogr. A*, 1030:201-208, 2004.
Oberacher, "Capillary monoliths for the analysis of nucleic acids by high-performance liquid chromatography-electrospray ionization mass spectrometry," *Trends Anal. Chem.*, 21(3):166-174, 2002.
Oefner and Huber, "A decade of high-resolution liquid chromatography of nucleic acids on styrene-divinylbenzene copolymers," *J. Chromatogr. B*, 782:27-55, 2002.
Patent Owner Motion to Exclude, served Dec. 10, 2018.
Patent Owner's Preliminary Response, served Jan. 19, 2018.
Patent Owner's Response, served Jul. 18, 2018.
Patent Owners SurReply, served Dec. 10, 2018.
Petition for IPR, Patent 8,383,340, served Sep. 29, 2017.
Petitioner's Reply, Redacted, served Oct. 18, 2018.
Phillips, "Antisense Therapeutics," $2^{nd}$ ed., 2005.
Polymer Laboratories Online Product Literature Request Form.
Polymer Laboratories, "Chromatography Products from Polymer Laboratories," Catalogue, 2004.
Polymer Laboratories, "Chromatography Products from Polymer Laboratories," Marketing Material.
Premstaller et al., "High-Performance Liquid Chromatography-Electrospray Ionization Mass Spectrometry of Single- and Double-Stranded Nucleic Acids Using Monolithic Capillary Columns," *Anal. Chem.*, 72:4386-4393, 2000.
Putral et al., "RNA Interference for the Treatment of Cancer," *Drug News Persp.*, 19(6):317-324, 2006.
Rathore and Velayudhan, "Scale-Up and Optimization in Preparative Chromatography," 2003.
Redacted Fotin-Mleczek Transcript.
Redacted Second Hornby Declaration.
Rodrigues et al., "Importance of intraparticle convection in the performance of chromatographic processes," *J. Chromatogr.*, 590:93-100, 1992.
Rodrigues et al., "Peak resolution in linear chromatography," *J. Chromatogr. A*, 653:189-198, 1993.

(56) References Cited

OTHER PUBLICATIONS

Russell and Zomerdjik, "The RNA polymerase I transcription machinery," *Biochem. Soc. Symp.*, 73:203-216, 2006.
Sambrook and Russell, *Molecular Cloning: A Laboratory Manual*, 3rd Edition, Cold Harbor Spring Press, 2001.
Sambrook et al., *Molecular Cloning: A Laboratory Manual*, 2nd Edition, Cold Spring Harbor Laboratory Press, 1989.
Schott and Schrade, "Single-step elongation of oligodeoxynucelotides using terminal deoxynucleotidyltransferase," *Eur. J. Biochem.*, 143:613-620, 1984.
Schott et al., "Column chromatographic purification of guanylate-rich synthetic oligodeoxyribonucleotides," *J. Chromatogr.*, 389:165-176, 1987.
Scott and Klug, "Ribozymes: structure and mechanism in RNA catalysis," *Trends Biochem. Sci.*, 220-224, 1996.
Shimabukuro-Vornhagen et al., "Cytokine release syndrome," *J. Immunother. Cancer*, 6(56):1-14,2018.
Skoog et al., "Principles of Instrumental Analysis," 5th ed., 1998.
Snyder, "Introduction to Modern Liquid Chromatography," 2nd ed., 1979.
Steitz and Moore, "RNA, the first macromolecular catalyst: the ribosome is a ribozyme," *Trends Biochem. Sci.*, 28(8):411-418, 2003.
Storz, "An Expanding Universe of Noncoding RNAs", *Science*, 296:1260-1263, 2002.
Sullenger and Gilboa, "Emerging clinical applications RNA," *Nature*, 418:252-258, 2002.
Svec and Frechet, "Kinetic Control of Pore Formation in Macroporous Polymers. Formation of "Molded" Porous Materials with High Flow Characteristics for Separations or Catalysis", *Chem. Mater.*, 7:707-715, 1995.
Svec, "Chapter 2: Organic Polymer Support Materials", In: *HPLC of Biological Macromolecules*, 2nd Edition, ed. Gooding and Regnier, Marcel Dekker, 2002.
Swiderski et al., "Polystyrene Reverse-Phase Ion-Pair Chromatography of Chimeric Ribozymes", In: *Analytical Biochemistry*, 216(1):83-88, 1994.
Tanaka et al., "IL-6 in Inflammation, Immunity, and Disease," *Cold Spring Harb. Perspect. Biol.*, 6:a016295, 2014.
Taniguchi and Hayashi, "A liquid chromatography/electrospray mass spectrometric study on the post-transcriptional modification of tRNA," *Nucleic Acids Res.*, 26(6):1481-1486, 1998.
Turkova, "Affinity Chromatography," 1978.
Tweeten and Tweeten, "Reversed-phase chromatography of proteins on resin-based wide-pore packings," *J. Chromatogr.*, 359:111-119, 1986.
Vaidyanathan et al., "Uridine Depletion and Chemical Modification Increase Cas9 mRNA Activity and Reduce Immunogenicity without HPLC Purification," *Mol Ther. Nucleic Acids*, 12:530-542 and supplemental information, 2018.
Viklund et al., "Monolithic, "Molded", Porous Materials with High Flow Characteristics for Separations, Catalysis, or Solid-Phase Chemistry: Control of Porous Properties during Polymerization," *Chem. Mater.*, 8:744-750, 1996.
Voet and Voet, Chapters 28-30 in: *Biochemistry*, John Wiley & Sons, Inc., 1990.
Waghmere et al., "Studying the mechanism of RNA separations using RNA chromatography and its application in the analysis of ribosomal RNA and RNA::RNA interactions," *J. Chromatogr. A*, 1216:1377-1382, 2009.
Zhang et al., "Antisense Inhibition," Chapter 2 In: *Antisense Therapeutics*, pp. 11-34, 2005.
Azarani and Hecker, "RNA analysis by ion-pair reversed-phase high performance liquid chromatography", *Nucleic Acids Research*, 29:e7, 2001.
Berinstein et al., "Association of serum Rituximab (IDEC-C2B8) concentration and antitumor response in the treatment of recurrent low-grade or follicular non-Hodgkin's lymphoma", *Ann. Oncol.*, 9:995-1001, 1998.
Bessis et al, "Immune responses to gene therapy vectors, influence on vector function an effector mechanisms", *Gene Ther.*, 2004,11.
Center for Biological Sequence Analysis, "SignalIP-5.0 Server", accessed May 28, 2019.
Chi et al., "Physical Stability of Proteins in Aqueous Solution: Mechanism and Driving Forces in Nonnative Protein Aggregation", *Pharm. Res.*, 20(9):1325-1336, 2003.
CureVac, "Custom RNActive", Capture from CureVac website on Jun. 16, 2006, obtained from the Internet Archive.
Declaration by Dr. Steve Pascolo Sep. 5, 2018.
Declaration by Dr. Thomas Schlake Sep. 5, 2018.
Declaration by Dr. Thomas Schlake, May 29, 2019.
Declaration by Prof. Jung, May 31, 2019.
Declaration of George Georgiou, Mar. 11, 2019.
Declaration of Graham K. Farrington PhD, Apr. 24, 2019.
Diebold et al, "Innate Antiviral Responses by Means of TLR7-Mediated Recognition of Single-Stranded RNA", *Science*, 303(5663):1529-1531, 2004.
Experimental results: "Anti-Drug Antibody Assay".
Experimental results: "IV administered. mRNA encoding Herceptin results in prolonged survival and: reduction of tumor volume in a mouse tumour model".
Fernandez-Pol, "Epidermal Growth Factor Receptor of A431 Cells—Characterization of a Monoclonal Anti-Receptor Antibody Non-competitive Agonist of Epidermal Growth Factor Action", *J. Biol. Chem.*, 260(8):5003-5011, 1985.
Heil et al, "Species-Specific recognition of Single-Stranded RNA via Toll-like Receptor 7 and 8", *Science*, 303(5663):1526-1529, 2004.
Hein et al., "Receptor and Binding Studies", In: Practical Methods in Cardiovascular Research, 723-783, 2005.
Hillmen et al: "The Complement Inhibitor Eculizumab in Paroxysmal Nocturnal Hemoglobinuria", *New Engl. J. Med.*, 355(12):1233-1243, 2006.
Hu et al., "Intratumoral injection of adenoviral vectors encoding tumor-targeted immunoconjugates for cancer immunotherapy", *Proc. Natl. Acad. Sci.*, 97(16):9221-9225, 2000.
Igarashi et al., "Factors affecting toxicity, response and progression-free survival in relapsed patients with indolent B-cell lymphoma and mantle cell lymphoma treated with rituximab: a Japanese phase II study", *Ann. Oncol.*, 13(6):928-943, 2002.
Joss et al, "Immunity to adenovirus and adeno-associated viral vectors, implications for gene therapy", *Gene Ther.*, 10:955-963, 2003.
Kurai et al., "Antibody-Dependent Cellular Cytotoxicity Mediated by Cetuximab against Lung Cancer Cell Lines", *Clin. Cancer Res.*, 13(5):1552-1561, 2007.
Kurien and Scofield, "Western Blotting", *Methods*, 38:283-293, 2006.
Kurt-Jones et al., "The role of antigen-presenting B cells in T cell priming in vivo. Studies of B cell-deficient mice", *J. Immunol.*, 140(11):3773-3778, 1988.
Leef et al., "Protective immunity to Bordetella pertussis requires both B cells and CD4(+) T cells for key functions other than specific antibody production", *J. Exper. Med.*, 191(11):1841-1852, 2000.
Lodish et al., "Molecular Cell Biology", 4th edition, W.H. Freeman and Company, 2000.
Lukavsky and Pulisi, "Large-scale preparation and purification of polyacrylamide-free RNA oligonucleotides", *RNA*, 10:889-893, 2004.
McKenna et al., "Purification and characterization of transcribed RNAs using gel filtration chromatography", *Nat. Protoc.*, 2(12):3270-3277, 2007.
Putzlitz and Blum, "Intrazelluläre Antikörper: Ein nenes Therapiekonzept gegen Virusinfektionen und Tumorerkrankungen", *Dtsch. Med. Wschr.*, 124:357-360., 1999.
Schlake et al., "mRNA as novel technology for passing immunotherapy", *Cell. Mol. Life Sci.*, 76(2):301-328, 2018.
Schlake et al., "mRNA: A Novel Avenue to Antibody Therapy?" *Mol. Ther.*, 37(4):773-784, 2019.
Seth, "Vector-Mediated Cancer Gene Therapy", *Cancer Biol. Ther.*, 4(5):512-517, 2005.

(56) References Cited

OTHER PUBLICATIONS

Shields et al., "High-performance liquid chromatography purification of homogenous-length RNA produced by trans cleavage with a hammerhead ribozyme", *RNA*, 5:1259-1267, 1999.

Simmons et al., "Prophylactic and Therapeutic Efficacy of Human Monoclonal Antibodies against H5N1 Influenza", *PLoS Med.*, 4(5):0928-0936, 2007.

Tobinai et al., "Japanese multicenter phase II and pharmacokinetic study of rituximab in relapsed or refractory patients with aggressive B-cell lymphoma", *Ann. Oncol.*, 15(5):821-830, 2004.

Tokuda et al., "Dose escalation and pharmacokinetic study of a humanized anti-HER2 monoclonal antibody in patients with HER2/neu-overexpressing metastatic breast cancer", *Br. J. Cancer*, 81(8):1419-1425, 1999.

Ye et al, "Naked DNA Transfer of Factor VIII Induced Transgene-Specific, Species-Independent Immune Response in Hemophilia A Mice", *Mol. Ther.*, 10(1):117-126, 2004.

Final Written Decision issued in Inter Partes Review IPR2017-02194, entered on Apr. 16, 2019.

Xue et al., "RNA Encoding the MPT83 Antigen Induces Protective Immune Responses against *Mycobacterium tuberculosis* Infection", *Infection and Immunity*, 72(11):6324-6329, 2004.

\* cited by examiner

```
CAG GCG TAT CTG CAG CAG AGC GGC GCG GAA CTG GTG CGC CCG
GGC GCG AGC GTG AAA ATG AGC TGC AAA GCG AGC GGC TAT ACC
TTT ACC AGC TAT AAC ATG CAT TGG GTG AAA CAG ACC CCG CGC
CAG GGC CTG GAA TGG ATT GGC GCG ATT TAT CCG GGC AAC GGC
GAT ACC AGC TAT AAC CAG AAA TTT AAA GGC AAA GCG ACC CTG
ACC GTG GAT AAA AGC AGC AGC ACC GCG TAT ATG CAG CTG AGC
AGC CTG ACC AGC GAA GAT AGC GCG GTG TAT TTT TGC GCG CGC
GTG GTG TAT TAT AGC AAC AGC TAT TGG TAT TTT GAT GTG TGG
GGC ACC GGC ACC ACC GTG ACC GTG AGC GGC CCG AGC GTG TTT
CCG CTG GCG CCG AGC AGC AAA AGC ACC AGC GGC GGC ACC GCG
GCG CTG GGC TGC CTG GTG AAA GAT TAT TTT CCG GAA CCG GTG
ACC GTG AGC TGG AAC AGC GGC GCG CTG ACC AGC GGC GTG CAT
ACC TTT CCG GCG GTG CTG CAG AGC AGC GGC CTG TAT AGC CTG
AGC AGC GTG GTG ACC GTG CCG AGC AGC AGC CTG GGC ACC CAG
ACC TAT ATT TGC AAC GTG AAC CAT AAA CCG AGC AAC ACC AAA
GTG GAT AAA AAA GCG GAA CCG AAA AGC TGC GAT AAA ACC CAT
ACC TGC CCG CCG TGC CCG GCG CCG GAA CTG CTG GGC GGC CCG
AGC GTG TTT CTG TTT CCG CCG AAA CCG AAA GAT ACC CTG ATG
ATT AGC CGC ACC CCG GAA GTG ACC TGC GTG GTG GTG GAT GTG
AGC CAT GAA GAT CCG GAA GTG AAA TTT AAC TGG TAT GTG GAT
GGC GTG GAA GTG CAT AAC GCG AAA ACC AAA CCG CGC GAA GAA
CAG TAT AAC AGC ACC TAT CGC GTG GTG AGC GTG CTG ACC GTG
CTG CAT CAG GAT TGG CTG AAC GGC AAA GAA TAT AAA TGC AAA
GTG AGC AAC AAA GCG CTG CCG GCG CCG ATT GAA AAA ACC ATT
AGC AAA GCG AAA GGC CAG CCG CGC GAA CCG CAG GTG TAT ACC
CTG CCG CCG AGC CGC GAT GAA CTG ACC AAA AAC CAG GTG AGC
CTG ACC TGC CTG GTG AAA GGC TTT TAT CCG AGC GAT ATT GCG
GTG GAA TGG GAA AGC AAC GGC CAG CCG GAA AAC AAC TAT AAA
ACC ACC CCG CCG GTG CTG GAT AGC GAT GGC AGC TTT TTT CTG
TAT AGC AAA CTG ACC GTG GAT AAA AGC CGC TGG CAG CAG GGC
AAC GTG TTT AGC TGC AGC GTG ATG CAT GAA GCG CTG CAT AAC
CAT TAT ACC CAG AAA AGC CTG AGC CTG AGC CCG GGC AAA TAA
```

Fig. 8

```
CAG GCC TAC CTG CAG CAG AGC GGC GCG GAG CTC GTG CGG CCG
GGG GCC TCG GTC AAG ATG AGC TGC AAG GCC AGC GGC TAC ACC
TTC ACG AGC TAC AAC ATG CAC TGG GTG AAG CAG ACC CCG CGC
CAG GGG CTG GAG TGG ATC GGC GCC ATC TAC CCC GGG AAC GGC
GAC ACC AGC TAC AAC CAG AAG TTC AAG GGC AAG GCG ACC CTG
ACG GTG GAC AAG TCG AGC AGC ACC GCC TAC ATG CAG CTC AGC
AGC CTG ACC TCG GAG GAC AGC GCC GTC TAC TTC TGC GCC CGG
GTG GTG TAC TAC AGC AAC AGC TAC TGG TAC TTC GAC GTC TGG
GGG ACC GGC ACG ACC GTG ACC GTG AGC GGG CCC AGC GTC TTC
CCC CTG GCC CCC TCG AGC AAG AGC ACC AGC GGC GGC ACG GCG
GCC CTC GGG TGC CTG GTG AAG GAC TAC TTC CCC GAG CCC GTG
ACC GTC AGC TGG AAC TCG GGC GCC CTG ACC AGC GGG GTG CAC
ACC TTC CCG GCC GTG CTC CAG AGC AGC GGC CTG TAC AGC CTG
AGC TCG GTC GTG ACG GTG CCC AGC AGC AGC CTC GGG ACC CAG
ACC TAC ATC TGC AAC GTC AAC CAC AAG CCC AGC AAC ACC AAG
GTG GAC AAG AAG GCG GAG CCC AAG TCG TGC GAC AAG ACG CAC
ACC TGC CCG CCC TGC CCC GCC CCC GAG CTG CTG GGC GGC CCG
AGC GTG TTC CTC TTC CCG CCC AAG CCC AAG GAC ACC CTG ATG
ATC AGC CGC ACC CCC GAG GTC ACG TGC GTG GTG GTC GAC GTG
AGC CAC GAG GAC CCC GAG GTG AAG TTC AAC TGG TAC GTC GAC
GGG GTG GAG GTG CAC AAC GCC AAG ACC AAG CCC CGG GAG GAG
CAG TAC AAC AGC ACC TAC CGC GTC GTG AGC GTG CTG ACC GTC
CTC CAC CAG GAC TGG CTG AAC GGC AAG GAG TAC AAG TGC AAG
GTG TCG AAC AAG GCC CTG CCG GCC CCC ATC GAG AAG ACG ATC
AGC AAG GCG AAG GGG CAG CCC CGG GAG CCC CAG GTG TAC ACC
CTC CCG CCC AGC CGC GAC GAG CTG ACC AAG AAC CAG GTC AGC
CTG ACC TGC CTC GTG AAG GGC TTC TAC CCC AGC GAC ATC GCC
GTG GAG TGG GAG TCG AAC GGG CAG CCC GAG AAC AAC TAC AAG
ACG ACC CCG CCC GTC CTG GAC AGC GAC GGC AGC TTC TTC CTG
TAC AGC AAG CTC ACC GTG GAC AAG AGC CGG TGG CAG CAG GGC
AAC GTG TTC AGC TGC TCG GTC ATG CAC GAG GCC CTG CAC AAC
CAC TAC ACC CAG AAG AGC CTG AGC CTC AGC CCC GGG AAG TGA
```

Fig. 9

```
CAG ATT GTG CTG AGC CAG AGC CCG GCG ATT CTG AGC GCG AGC
CCG GGC GAA AAA GTG ACC ATG ACC TGC CGC GCG AGC AGC AGC
GTG AGC TAT ATG CAT TGG TAT CAG CAG AAA CCG GGC AGC AGC
CCG AAA CCG TGG ATT TAT GCG CCG AGC AAC CTG GCG AGC GGC
GTG CCG GCG CGC TTT AGC GGC AGC GGC AGC GGC ACC AGC TAT
AGC CTG ACC ATT AGC CGC GTG GAA GCG GAA GAT GCG GCG ACC
TAT TAT TGC CAG CAG TGG AGC TTT AAC CCG CCG ACC TTT GGC
GCG GGC ACC AAA CTG GAA CTG AAA CGC ACC GTG GCG GCG CCG
AGC GTG TTT ATT TTT CCG CCG AGC GAT GAA CAG CTG AAA AGC
GGC ACC GCG AGC GTG GTG TGC CTG CTG AAC AAC TTT TAT CCG
CGC GAA GCG AAA GTG CAG TGG AAA GTG GAT AAC GCG CTG CAG
AGC GGC AAC AGC CAG GAA AGC GTG ACC GAA CAG GAT AGC AAA
GAT AGC ACC TAT AGC CTG AGC AGC ACC CTG ACC CTG AGC AAA
GCG GAT TAT GAA AAA CAT AAA GTG TAT GCG TGC GAA GTG ACC
CAT CAG GGC CTG AGC AGC CCG GTG ACC AAA AGC TTT AAC CGC
TAA
```

Fig. 10

```
CAG ATC GTG CTG AGC CAG TCG CCG GCC ATC CTC AGC GCG AGC
CCC GGC GAG AAG GTC ACC ATG ACG TGC CGG GCC AGC AGC TCG
GTG AGC TAC ATG CAC TGG TAC CAG CAG AAG CCC GGG AGC AGC
CCC AAG CCG TGG ATC TAC GCC CCC AGC AAC CTG GCC TCG GGC
GTG CCC GCG CGC TTC AGC GGG AGC GGC AGC GGG ACC AGC TAC
AGC CTG ACC ATC TCG CGG GTC GAG GCC GAG GAC GCC GCC ACC
TAC TAC TGC CAG CAG TGG AGC TTC AAC CCG CCC ACG TTC GGC
GCC GGC ACC AAG CTC GAG CTG AAG CGC ACC GTG GCG GCC CCC
AGC GTG TTC ATC TTC CCG CCC AGC GAC GAG CAG CTG AAG AGC
GGG ACC GCC TCG GTC GTG TGC CTC CTG AAC AAC TTC TAC CCC
CGG GAG GCC AAG GTG CAG TGG AAG GTC GAC AAC GCG CTG CAG
AGC GGC AAC AGC CAG GAG AGC GTG ACG GAG CAG GAC AGC AAG
GAC AGC ACC TAC TCG CTC AGC AGC ACC CTG ACC CTG AGC AAG
GCC GAC TAC GAG AAG CAC AAG GTG TAC GCC TGC GAG GTC ACG
CAC CAG GGG CTC AGC TCG CCC GTG ACC AAG AGC TTC AAC CGC
TGA
```

Fig. 11

AAGCTTACCATGGCCGTGATGGCGCCGCGGACCCTGGTCCTCCTGCTGAGCGGCGCCC
TCGCCCTGACGCAGACCTGGGCCGGGCAGGCCTACCTGCAGCAGAGCGGCGCGGAGCT
CGTGCGGCCGGGGGCCTCGGTCAAGATGAGCTGCAAGGCCAGCGGCTACACCTTCACG
AGCTACAACATGCACTGGGTGAAGCAGACCCCGCGCCAGGGGCTGGAGTGGATCGGCG
CCATCTACCCCGGGAACGGCGACACCAGCTACAACCAGAAGTTCAAGGGCAAGGCGAC
CCTGACGGTGGACAAGTCGAGCAGCACCGCCTACATGCAGCTCAGCAGCCTGACCTCG
GAGGACAGCGCCGTCTACTTCTGCGCCCGGGTGGTGTACTACAGCAACAGCTACTGGT
ACTTCGACGTCTGGGGGACCGGCACGACCGTGACCGTGAGCGGGCCCAGCGTCTTCCC
CCTGGCCCCCTCGAGCAAGAGCACCAGCGGCGGCACGGCGGCCCTCGGGTGCCTGGTG
AAGGACTACTTCCCCGAGCCCGTGACCGTCAGCTGGAACTCGGGCGCCCTGACCAGCG
GGGTGCACACCTTCCCGGCCGTGCTCCAGAGCAGCGGCCTGTACAGCCTGAGCTCGGT
CGTGACGGTGCCCAGCAGCAGCCTCGGGACCCAGACCTACATCTGCAACGTCAACCAC
AAGCCCAGCAACACCAAGGTGGACAAGAAGGCGGAGCCCAAGTCGTGCGACAAGACGC
ACACCTGCCCGCCCTGCCCCGCCCCGAGCTGCTGGGCGGCCCGAGCGTGTTCCTCTT
CCCGCCCAAGCCCAAGGACACCCTGATGATCAGCCGCACCCCGAGGTCACGTGCGTG
GTGGTCGACGTGAGCCACGAGGACCCCGAGGTGAAGTTCAACTGGTACGTCGACGGGG
TGGAGGTGCACAACGCCAAGACCAAGCCCCGGGAGGAGCAGTACAACAGCACCTACCG
CGTCGTGAGCGTGCTGACCGTCCTCCACCAGGACTGGCTGAACGGCAAGGAGTACAAG
TGCAAGGTGTCGAACAAGGCCCTGCCGGCCCCCATCGAGAAGACGATCAGCAAGGCGA
AGGGGCAGCCCCGGGAGCCCCAGGTGTACACCCTCCCGCCCAGCCGCGACGAGCTGAC
CAAGAACCAGGTCAGCCTGACCTGCCTCGTGAAGGGCTTCTACCCCAGCGACATCGCC
GTGGAGTGGGAGTCGAACGGGCAGCCCGAGAACAACTACAAGACGACCCCGCCCGTCC
TGGACAGCGACGGCAGCTTCTTCCTGTACAGCAAGCTCACCGTGGACAAGAGCCGGTG
GCAGCAGGGCAACGTGTTCAGCTGCTCGGTCATGCACGAGGCCCTGCACAACCACTAC
ACCCAGAAGAGCCTGAGCCTCAGCCCCGGGAAGCATCATCATCATCATCATTGACCAG
ATCTTTCTGACATTTCTGACATTTCTGACATTTCTGACATTTCTGACATTTCTGACAT
TTCTGACATTTCTGACATTTCTGACATTTCTGACATATGCATACCATGGCCGTGATGG
CGCCGCGGACCCTGGTCCTCCTGCTGAGCGGCGCCCTCGCCCTGACGCAGACCTGGGC
CGGGCAGATCGTGCTGAGCCAGTCGCCGGCCATCCTCAGCGCGAGCCCCGGCGAGAAG
GTCACCATGACGTGCCGGGCCAGCAGCTCGGTGAGCTACATGCACTGGTACCAGCAGA
AGCCCGGGAGCAGCCCCAAGCCGTGGATCTACGCCCCAGCAACCTGGCCTCGGGCGT
GCCCGCGCGCTTCAGCGGGAGCGGCAGCGGGACCAGCTACAGCCTGACCATCTCGCGG
GTCGAGGCCGAGGACGCCGCCACCTACTACTGCCAGCAGTGGAGCTTCAACCCGCCCA
CGTTCGGCGCCGGCACCAAGCTCGAGCTGAAGCGCACCGTGGCGGCCCCAGCGTGTT
CATCTTCCCGCCCAGCGACGAGCAGCTGAAGAGCGGGACCGCCTCGGTCGTGTGCCTC
CTGAACAACTTCTACCCCGGGAGGCCAAGGTGCAGTGGAAGGTCGACAACGCGCTGC
AGAGCGGCAACAGCCAGGAGAGCGTGACGGAGCAGGACAGCAAGGACAGCACCTACTC
GCTCAGCAGCACCCTGACCCTGAGCAAGGCCGACTACGAGAAGCACAAGGTGTACGCC
TGCGAGGTCACGCACCAGGGGCTCAGCTCGCCCGTGACCAAGAGCTTCAACCGCTGAC
CACTAGT

Fig. 12

```
CAG GTG CAG CTG AAA CAG AGC GGC CCG GGC CTG GTG CAG CCG
AGC CAG AGC CTG AGC ATT ACC TGC ACC GTG AGC GGC TTT AGC
CTG ACC AAC TAT GGC GTG CAT TGG GTG CGC CAG AGC CCG GGC
AAA GGC CTG GAA TGG CTG GGC GTG ATT TGG AGC GGC GGC AAC
ACC GAT TAT AAC ACC CCG TTT ACC AGC CGC CTG AGC ATT AAC
AAA GAT AAC AGC AAA AGC CAG GTG TTT TTT AAA ATG AAC AGC
CTG CAG AGC AAC GAT ACC GCG ATT TAT TAT TGC GCG CGC GCG
CTG ACC TAT TAT GAT TAT GAA TTT GCG TAT TGG GGC CAG GGC
ACC CTG GTG ACC GTG AGC GCG GCG AGC ACC AAA GGC CCG AGC
GTG TTT CCG CTG GCG CCG AGC AGC AAA AGC ACC AGC GGC GGC
ACC GCG GCG CTG GGC TGC CTG GTG AAA GAT TAT TTT CCG GAA
CCG GTG ACC GTG AGC TGG AAC AGC GGC GCG CTG ACC AGC GGC
GTG CAT ACC TTT CCG GCG GTG CTG CAG AGC AGC GGC CTG TAT
AGC CTG AGC AGC GTG GTG ACC GTG CCG AGC AGC AGC CTG GGC
ACC CAG ACC TAT ATT TGC AAC GTG AAC CAT AAA CCG AGC AAC
ACC AAA GTG GAT AAA CGC GTG GAA CCG AAA AGC CCG AAA AGC
TGC GAT AAA ACC CAT ACC TGC CCG CCG TGC CCG GCG CCG GAA
CTG CTG GGC GGC CCG AGC GTG TTT CTG TTT CCG CCG AAA CCG
AAA GAT ACC CTG ATG ATT AGC CGC ACC CCG GAA GTG ACC TGC
GTG GTG GTG GAT GTG AGC CAT GAA GAT CCG GAA GTG AAA TTT
AAC TGG TAT GTG GAT GGC GTG GAA GTG CAT AAC GCG AAA ACC
AAA CCG CGC GAA GAA CAG TAT AAC AGC ACC TAT CGC GTG GTG
AGC GTG CTG ACC GTG CTG CAT CAG GAT TGG CTG AAC GGC AAA
GAA TAT AAA TGC AAA GTG AGC AAC AAA GCG CTG CCG GCG CCG
ATT GAA AAA ACC ATT AGC AAA GCG AAA GGC CAG CCG CGC GAA
CCG CAG GTG TAT ACC CTG CCG CCG AGC CGC GAT GAA CTG ACC
AAA AAC CAG GTG AGC CTG ACC TGC CTG GTG AAA GGC TTT TAT
CCG AGC GAT ATT GCG GTG GAA TGG GAA AGC AAC GGC CAG CCG
GAA AAC AAC TAT AAA ACC ACC CCG CCG GTG CTG GAT AGC GAT
GGC AGC TTT TTT CTG TAT AGC AAA CTG ACC GTG GAT AAA AGC
CGC TGG CAG CAG GGC AAC GTG TTT AGC TGC AGC GTG ATG CAT
GAA GCG CTG CAT AAC CAT TAT ACC CAG AAA AGC CTG AGC CTG
AGC CCG GGC AAA TAA
```

Fig. 13

```
CAG GTG CAG CTG AAG CAG AGC GGC CCG GGG CTC GTC CAG CCC
TCG CAG AGC CTG AGC ATC ACC TGC ACG GTG AGC GGC TTC AGC
CTG ACC AAC TAC GGG GTG CAC TGG GTC CGG CAG TCG CCC GGC
AAG GGG CTC GAG TGG CTG GGC GTG ATC TGG AGC GGC GGG AAC
ACC GAC TAC AAC ACC CCC TTC ACG AGC CGC CTG AGC ATC AAC
AAG GAC AAC AGC AAG TCG CAG GTG TTC TTC AAG ATG AAC AGC
CTC CAG AGC AAC GAC ACC GCC ATC TAC TAC TGC GCG CGG GCC
CTG ACC TAC TAC GAC TAC GAG TTC GCC TAC TGG GGC CAG GGG
ACC CTG GTC ACG GTG AGC GCC GCG AGC ACC AAG GGC CCG AGC
GTG TTC CCC CTC GCC CCC TCG AGC AAG AGC ACC AGC GGC GGG
ACC GCC GCC CTG GGC TGC CTG GTC AAG GAC TAC TTC CCC GAG
CCG GTG ACG GTG AGC TGG AAC TCG GGG GCC CTC ACC AGC GGC
GTC CAC ACC TTC CCC GCG GTG CTG CAG AGC AGC GGG CTG TAC
AGC CTC AGC TCG GTG GTC ACC GTG CCC AGC AGC AGC CTG GGC
ACG CAG ACC TAC ATC TGC AAC GTG AAC CAC AAG CCC AGC AAC
ACC AAG GTC GAC AAG CGC GTG GAG CCG AAG TCG CCC AAG AGC
TGC GAC AAG ACC CAC ACG TGC CCG CCC TGC CCC GCC CCC GAG
CTG CTC GGC GGG CCC AGC GTG TTC CTG TTC CCG CCC AAG CCC
AAG GAC ACC CTG ATG ATC AGC CGG ACC CCC GAG GTC ACC TGC
GTG GTG GTC GAC GTG AGC CAC GAG GAC CCG GAG GTG AAG TTC
AAC TGG TAC GTC GAC GGC GTG GAG GTG CAC AAC GCC AAG ACG
AAG CCC CGC GAG GAG CAG TAC AAC AGC ACC TAC CGG GTC GTG
TCG GTG CTC ACC GTC CTG CAC CAG GAC TGG CTG AAC GGG AAG
GAG TAC AAG TGC AAG GTG AGC AAC AAG GCC CTC CCC GCG CCC
ATC GAG AAG ACC ATC AGC AAG GCC AAG GGC CAG CCG CGC GAG
CCC CAG GTG TAC ACG CTG CCC CCC AGC CGG GAC GAG CTG ACC
AAG AAC CAG GTC AGC CTC ACC TGC CTG GTG AAG GGG TTC TAC
CCG TCG GAC ATC GCC GTG GAG TGG GAG AGC AAC GGC CAG CCC
GAG AAC AAC TAC AAG ACC ACG CCC CCG GTC CTG GAC AGC GAC
GGC AGC TTC TTC CTC TAC AGC AAG CTG ACC GTG GAC AAG AGC
CGC TGG CAG CAG GGG AAC GTG TTC TCG TGC AGC GTC ATG CAC
GAG GCC CTG CAC AAC CAC TAC ACC CAG AAG AGC CTC AGC CTG
AGC CCC GGC AAG TGA
```

Fig. 14

```
GAT ATT CTG CTG ACC CAG AGC CCG GTG ATT CTG AGC GTG AGC
CCG GGC GAA CGC GTG AGC TTT AGC TGC CGC GCG AGC CAG AGC
ATT GGC ACC AAC ATT CAT TGG TAT CAG CAG CGC ACC AAC GGC
AGC CCG CGC CTG CTG ATT AAA TAT GCG AGC GAA AGC ATT AGC
GGC ATT CCG AGC CGC TTT AGC GGC AGC GGC AGC GGC ACC GAT
TTT ACC CTG AGC ATT AAC AGC GTG GAA AGC GAA GAT ATT GCG
GAT TAT TAT TGC CAG CAG AAC AAC AAC TGG CCG ACC ACC TTT
GGC GCG GGC ACC AAA CTG GAA CTG AAA CGC ACC GTG GCG GCG
CCG AGC GTG TTT ATT TTT CCG CCG AGC GAT GAA CAG CTG AAA
AGC GGC ACC GCG AGC GTG GTG TGC CTG CTG AAC AAC TTT TAT
CCG CGC GAA GCG AAA GTG CAG TGG AAA GTG GAT AAC GCG CTG
CAG AGC GGC AAC AGC CAG GAA AGC GTG ACC GAA CAG GAT AGC
AAA GAT AGC ACC TAT AGC CTG AGC AGC ACC CTG ACC CTG AGC
AAA GCG GAT TAT GAA AAA CAT AAA GTG TAT GCG TGC GAA GTG
ACC CAT CAG GGC CTG AGC AGC CCG GTG ACC AAA AGC TTT AAC
CGC GGC GCG TAA
```

Fig. 15

```
GAC ATC CTG CTC ACC CAG AGC CCG GTG ATC CTG TCG GTC AGC
CCC GGC GAG CGG GTG AGC TTC AGC TGC CGC GCC AGC CAG TCG
ATC GGG ACG AAC ATC CAC TGG TAC CAG CAG CGG ACC AAC GGC
AGC CCC CGC CTG CTC ATC AAG TAC GCG AGC GAG AGC ATC AGC
GGG ATC CCC TCG CGG TTC AGC GGC AGC GGG AGC GGC ACC GAC
TTC ACC CTG AGC ATC AAC AGC GTG GAG TCG GAG GAC ATC GCC
GAC TAC TAC TGC CAG CAG AAC AAC AAC TGG CCG ACG ACC TTC
GGC GCC GGG ACC AAG CTG GAG CTC AAG CGC ACC GTC GCC GCG
CCC AGC GTG TTC ATC TTC CCG CCC AGC GAC GAG CAG CTG AAG
AGC GGC ACG GCC AGC GTG GTC TGC CTG CTC AAC AAC TTC TAC
CCC CGG GAG GCC AAG GTG CAG TGG AAG GTG GAC AAC GCC CTG
CAG TCG GGG AAC AGC CAG GAG AGC GTC ACC GAG CAG GAC AGC
AAG GAC AGC ACC TAC AGC CTG TCG AGC ACC CTC ACG CTG AGC
AAG GCC GAC TAC GAG AAG CAC AAG GTG TAC GCG TGC GAG GTG
ACC CAC CAG GGC CTG AGC AGC CCC GTC ACC AAG TCG TTC AAC
CGC GGC GCC TGA
```

Fig. 16

AAGCTTACCATGGCCGTGATGGCGCCGCGGACCCTGGTCCTCCTGCTGAGCGGCGCCC
TCGCCCTGACGCAGACCTGGGCCGGGCAGGTGCAGCTGAAGCAGAGCGGCCCGGGGCT
CGTCCAGCCCTCGCAGAGCCTGAGCATCACCTGCACGGTGAGCGGCTTCAGCCTGACC
AACTACGGGGTGCACTGGGTCCGGCAGTCGCCCGGCAAGGGGCTCGAGTGGCTGGGCG
TGATCTGGAGCGGCGGGAACACCGACTACAACACCCCCTTCACGAGCCGCCTGAGCAT
CAACAAGGACAACAGCAAGTCGCAGGTGTTCTTCAAGATGAACAGCCTCCAGAGCAAC
GACACCGCCATCTACTACTGCGCGCGGGCCCTGACCTACTACGACTACGAGTTCGCCT
ACTGGGGCCAGGGGACCCTGGTCACGGTGAGCGCCGCGAGCACCAAGGGCCCGAGCGT
GTTCCCCCTCGCCCCTCGAGCAAGAGCACCAGCGGCGGGACCGCCGCCCTGGGCTGC
CTGGTCAAGGACTACTTCCCCGAGCCGGTGACGGTGAGCTGGAACTCGGGGGCCCTCA
CCAGCGGCGTCCACACCTTCCCCGCGGTGCTGCAGAGCAGCGGGCTGTACAGCCTCAG
CTCGGTGGTCACCGTGCCCAGCAGCAGCCTGGGCACGCAGACCTACATCTGCAACGTG
AACCACAAGCCCAGCAACACCAAGGTCGACAAGCGCGTGGAGCCGAAGTCGCCCAAGA
GCTGCGACAAGACCCACACGTGCCCGCCCTGCCCCGCCCCGAGCTGCTCGGCGGGCC
CAGCGTGTTCCTGTTCCCGCCCAAGCCCAAGGACACCCTGATGATCAGCCGGACCCCC
GAGGTCACCTGCGTGGTGGTCGACGTGAGCCACGAGGACCCGGAGGTGAAGTTCAACT
GGTACGTCGACGGCGTGGAGGTGCACAACGCCAAGACGAAGCCCCGCGAGGAGCAGTA
CAACAGCACCTACCGGGTCGTGTCGGTGCTCACCGTCCTGCACCAGGACTGGCTGAAC
GGGAAGGAGTACAAGTGCAAGGTGAGCAACAAGGCCCTCCCCGCGCCCATCGAGAAGA
CCATCAGCAAGGCCAAGGGCCAGCCGCGCGAGCCCCAGGTGTACACGCTGCCCCCCAG
CCGGGACGAGCTGACCAAGAACCAGGTCAGCCTCACCTGCCTGGTGAAGGGGTTCTAC
CCGTCGGACATCGCCGTGGAGTGGGAGAGCAACGGCCAGCCCGAGAACAACTACAAGA
CCACGCCCCCGGTCCTGGACAGCGACGGCAGCTTCTTCCTCTACAGCAAGCTGACCGT
GGACAAGAGCCGCTGGCAGCAGGGGAACGTGTTCTCGTGCAGCGTCATGCACGAGGCC
CTGCACAACCACTACACCCAGAAGAGCCTCAGCCTGAGCCCCGGCAAGCATCATCATC
ATCATCATTGACCAGATCTTTCTGACATTTCTGACATTTCTGACATTTCTGACATTTC
TGACATTTCTGACATTTCTGACATTTCTGACATTTCTGACATTTCTGACATATGCATA
CCATGGCCGTGATGGCGCCGCGGACCCTGGTCCTCCTGCTGAGCGGCGCCCTCGCCCT
GACGCAGACCTGGGCCGGGACATCCTGCTCACCCAGAGCCCGGTGATCCTGTCGGTC
AGCCCCGGCGAGCGGGTGAGCTTCAGCTGCCGCGCCAGCCAGTCGATCGGGACGAACA
TCCACTGGTACCAGCAGCGGACCAACGGCAGCCCCCGCCTGCTCATCAAGTACGCGAG
CGAGAGCATCAGCGGGATCCCCTCGCGGTTCAGCGGCAGCGGGAGCGGCACCGACTTC
ACCCTGAGCATCAACAGCGTGGAGTCGGAGGACATCGCCGACTACTACTGCCAGCAGA
ACAACAACTGGCCGACGACCTTCGGCGCCGGGACCAAGCTGGAGCTCAAGCGCACCGT
CGCCGCGCCCAGCGTGTTCATCTTCCCGCCCAGCGACGAGCAGCTGAAGAGCGGCACG
GCCAGCGTGGTCTGCCTGCTCAACAACTTCTACCCCGGGAGGCCAAGGTGCAGTGGA
AGGTGGACAACGCCCTGCAGTCGGGGAACAGCCAGGAGAGCGTCACCGAGCAGGACAG
CAAGGACAGCACCTACAGCCTGTCGAGCACCCTCACGCTGAGCAAGGCCGACTACGAG
AAGCACAAGGTGTACGCGTGCGAGGTGACCCACCAGGGCCTGAGCAGCCCCGTCACCA
AGTCGTTCAACCGCGGCGCCTGACCACTAGT

Fig. 17

```
GAA GTG CAG CTG GTG GAA AGC GGC GGC GGC CTG GTG CAG CCG
GGC GGC AGC CTG CGC CTG AGC TGC GCG GCG AGC GGC TTT AAC
ATT AAA GAT ACC TAT ATT CAT TGG GTG CGC CAG GCG CCG GGC
AAA GGC CTG GAA TGG GTG GCG CGC ATT TAT CCG ACC AAC GGC
TAT ACC CGC TAT GCG GAT AGC GTG AAA GGC CGC TTT ACC ATT
AGC GCG GAT ACC AGC AAA AAC ACC GCG TAT CTG CAG ATG AAC
AGC CTG CGC GCG GAA GAT ACC GCG GTG TAT TAT TGC AGC CGC
TGG GGC GGC GAT GGC TTT TAT GCG ATG GAT TAT TGG GGC CAG
GGC ACC CTG GTG ACC GTG AGC AGC GCG AGC ACC AAA GGC CCG
AGC GTG TTT CCG CTG GCG CCG AGC AGC AAA AGC ACC AGC GGC
GGC ACC GCG GCG CTG GGC TGC CTG GTG AAA GAT TAT TTT CCG
GAA CCG GTG ACC GTG AGC TGG AAC AGC GGC GCG CTG ACC AGC
GGC GTG CAT ACC TTT CCG GCG GTG CTG CAG AGC AGC GGC CTG
TAT AGC CTG AGC AGC GTG GTG ACC GTG CCG AGC AGC AGC CTG
GGC ACC CAG ACC TAT ATT TGC AAC GTG AAC CAT AAA CCG AGC
AAC ACC AAA GTG GAT AAA AAA GTG GAA CCG CCG AAA AGC TGC
GAT AAA ACC CAT ACC TGC CCG CCG TGC CCG GCG CCG GAA CTG
CTG GGC GGC CCG AGC GTG TTT CTG TTT CCG CCG AAA CCG AAA
GAT ACC CTG ATG ATT AGC CGC ACC CCG GAA GTG ACC TGC GTG
GTG GTG GAT GTG AGC CAT GAA GAT CCG GAA GTG AAA TTT AAC
TGG TAT GTG GAT GGC GTG GAA GTG CAT AAC GCG AAA ACC AAA
CCG CGC GAA GAA CAG TAT AAC AGC ACC TAT CGC GTG GTG AGC
GTG CTG ACC GTG CTG CAT CAG GAT TGG CTG AAC GGC AAA GAA
TAT AAA TGC AAA GTG AGC AAC AAA GCG CTG CCG GCG CCG ATT
GAA AAA ACC ATT AGC AAA GCG AAA GGC CAG CCG CGC GAA CCG
CAG GTG TAT ACC CTG CCG CCG AGC CGC GAT GAA CTG ACC AAA
AAC CAG GTG AGC CTG ACC TGC CTG GTG AAA GGC TTT TAT CCG
AGC GAT ATT GCG GTG GAA TGG GAA AGC AAC GGC CAG CCG GAA
AAC AAC TAT AAA ACC ACC CCG CCG GTG CTG GAT AGC GAT GGC
AGC TTT TTT CTG TAT AGC AAA CTG ACC GTG GAT AAA AGC CGC
TGG CAG CAG GGC AAC GTG TTT AGC TGC AGC GTG ATG CAT GAA
GCG CTG CAT AAC CAT TAT ACC CAG AAA AGC CTG AGC CTG AGC
CCG GGC AAA TAA
```

Fig. 18

```
GAG GTG CAG CTG GTC GAG AGC GGC GGG GGC CTC GTG CAG CCG
GGC GGG TCG CTG CGG CTG AGC TGC GCC GCG AGC GGG TTC AAC
ATC AAG GAC ACC TAC ATC CAC TGG GTG CGC CAG GCC CCC GGC
AAG GGC CTC GAG TGG GTC GCC CGG ATC TAC CCC ACG AAC GGG
TAC ACC CGC TAC GCC GAC AGC GTG AAG GGC CGG TTC ACC ATC
AGC GCG GAC ACC TCG AAG AAC ACG GCC TAC CTG CAG ATG AAC
AGC CTG CGC GCC GAG GAC ACC GCC GTG TAC TAC TGC AGC CGG
TGG GGC GGC GAC GGG TTC TAC GCC ATG GAC TAC TGG GGG CAG
GGC ACC CTC GTC ACC GTG AGC AGC GCG TCG ACG AAG GGG CCC
AGC GTG TTC CCG CTG GCC CCC AGC AGC AAG AGC ACC AGC GGC
GGG ACC GCC GCC CTG GGC TGC CTC GTC AAG GAC TAC TTC CCC
GAG CCC GTG ACC GTG TCG TGG AAC AGC GGC GCG CTG ACG AGC
GGG GTC CAC ACC TTC CCG GCC GTG CTG CAG AGC AGC GGC CTC
TAC TCG CTG AGC AGC GTG GTC ACC GTG CCC AGC AGC AGC CTG
GGG ACC CAG ACG TAC ATC TGC AAC GTG AAC CAC AAG CCC TCG
AAC ACC AAG GTC GAC AAG AAG GTG GAG CCC CCG AAG AGC TGC
GAC AAG ACC CAC ACC TGC CCG CCC TGC CCC GCC CCC GAG CTC
CTG GGC GGG CCC AGC GTG TTC CTG TTC CCG CCC AAG CCC AAG
GAC ACG CTC ATG ATC AGC CGC ACC CCC GAG GTC ACC TGC GTG
GTG GTC GAC GTG AGC CAC GAG GAC CCC GAG GTG AAG TTC AAC
TGG TAC GTC GAC GGC GTG GAG GTG CAC AAC GCC AAG ACC AAG
CCG CGG GAG GAG CAG TAC AAC TCG ACG TAC CGC GTC GTG AGC
GTG CTG ACC GTC CTG CAC CAG GAC TGG CTC AAC GGC AAG GAG
TAC AAG TGC AAG GTG AGC AAC AAG GCC CTG CCC GCG CCC ATC
GAG AAG ACC ATC AGC AAG GCC AAG GGG CAG CCC CGG GAG CCG
CAG GTG TAC ACC CTG CCC CCC AGC CGC GAC GAG CTC ACG AAG
AAC CAG GTC AGC CTG ACC TGC CTG GTG AAG GGC TTC TAC CCC
TCG GAC ATC GCC GTG GAG TGG GAG AGC AAC GGG CAG CCG GAG
AAC AAC TAC AAG ACC ACC CCG CCC GTC CTC GAC AGC GAC GGC
AGC TTC TTC CTG TAC AGC AAG CTG ACG GTG GAC AAG TCG CGG
TGG CAG CAG GGC AAC GTG TTC AGC TGC AGC GTC ATG CAC GAG
GCC CTC CAC AAC CAC TAC ACC CAG AAG AGC CTG AGC CTG AGC
CCC GGG AAG TGA
```

Fig. 19

GAT ATT CAG ATG ACC CAG AGC CCG AGC AGC CTG AGC GCG AGC
GTG GGC GAT CGC GTG ACC ATT ACC TGC CGC GCG AGC CAG GAT
GTG AAC ACC GCG GTG GCG TGG TAT CAG CAG AAA CCG GGC AAA
GCG CCG AAA CTG CTG ATT TAT AGC GCG AGC TTT CTG TAT AGC
GGC GTG CCG AGC CGC TTT AGC GGC AGC CGC AGC GGC ACC GAT
TTT ACC CTG ACC ATT AGC AGC CTG CAG CCG GAA GAT TTT GCG
ACC TAT TAT TGC CAG CAG CAT TAT ACC ACC CCG CCG ACC TTT
GGC CAG GGC ACC AAA GTG GAA ATT AAA CGC ACC GTG GCG GCG
CCG AGC GTG TTT ATT TTT CCG CCG AGC GAT GAA CAG CTG AAA
AGC GGC ACC GCG AGC GTG GTG TGC CTG CTG AAC AAC TTT TAT
CCG CGC GAA GCG AAA GTG CAG TGG AAA GTG GAT AAC GCG CTG
CAG AGC GGC AAC AGC CAG GAA AGC GTG ACC GAA CAG GAT AGC
AAA GAT AGC ACC TAT AGC CTG AGC AGC ACC CTG ACC CTG AGC
AAA GCG GAT TAT GAA AAA CAT AAA GTG TAT GCG TGC GAA GTG
ACC CAT CAG GGC CTG AGC AGC CCG GTG ACC AAA AGC TTT AAC
CGC GGC GAA TGC TAA

Fig. 20

```
GAC ATC CAG ATG ACC CAG AGC CCG TCG AGC CTG AGC GCC AGC
GTG GGC GAC CGG GTC ACG ATC ACC TGC CGC GCG AGC CAG GAC
GTG AAC ACC GCC GTG GCC TGG TAC CAG CAG AAG CCC GGG AAG
GCC CCC AAG CTC CTG ATC TAC TCG GCG AGC TTC CTG TAC AGC
GGC GTC CCC AGC CGG TTC AGC GGG TCG CGC AGC GGC ACC GAC
TTC ACG CTC ACC ATC AGC AGC CTG CAG CCG GAG GAC TTC GCC
ACC TAC TAC TGC CAG CAG CAC TAC ACC ACG CCC CCC ACC TTC
GGG CAG GGC ACC AAG GTG GAG ATC AAG CGG ACC GTG GCC GCC
CCC AGC GTC TTC ATC TTC CCG CCC AGC GAC GAG CAG CTG AAG
TCG GGC ACG GCC AGC GTG GTG TGC CTC CTG AAC AAC TTC TAC
CCC CGC GAG GCG AAG GTC CAG TGG AAG GTG GAC AAC GCC CTG
CAG AGC GGG AAC AGC CAG GAG AGC GTG ACC GAG CAG GAC TCG
AAG GAC AGC ACC TAC AGC CTC AGC AGC ACC CTG ACG CTG AGC
AAG GCC GAC TAC GAG AAG CAC AAG GTC TAC GCC TGC GAG GTG
ACC CAC CAG GGG CTC TCG AGC CCC GTG ACC AAG AGC TTC AAC
CGG GGC GAG TGC TGA
```

Fig. 21

AAGCTTACCATGGCCGTGATGGCGCCGCGGACCCTGGTCCTCCTGCTGAGCGGCGCCC
TCGCCCTGACGCAGACCTGGGCCGGGGAGGTGCAGCTGGTCGAGAGCGGCGGGGGCCT
CGTGCAGCCGGGCGGGTCGCTGCGGCTGAGCTGCGCCGCGAGCGGGTTCAACATCAAG
GACACCTACATCCACTGGGTGCGCCAGGCCCCCGGCAAGGGCCTCGAGTGGGTCGCCC
GGATCTACCCCACGAACGGGTACACCCGCTACGCCGACAGCGTGAAGGGCCGGTTCAC
CATCAGCGCGGACACCTCGAAGAACACGGCCTACCTGCAGATGAACAGCCTGCGCGCC
GAGGACACCGCCGTGTACTACTGCAGCCGGTGGGCGGCGACGGGTTCTACGCCATGG
ACTACTGGGGCAGGGCACCCTCGTCACCGTGAGCAGCGCGTCGACGAAGGGGCCCAG
CGTGTTCCCGCTGGCCCCAGCAGCAAGAGCACCAGCGGCGGGACCGCCGCCCTGGGC
TGCCTCGTCAAGGACTACTTCCCCGAGCCCGTGACCGTGTCGTGGAACAGCGGCGCGC
TGACGAGCGGGGTCCACACCTTCCCGGCCGTGCTGCAGAGCAGCGGCCTCTACTCGCT
GAGCAGCGTGGTCACCGTGCCCAGCAGCAGCCTGGGGACCCAGACGTACATCTGCAAC
GTGAACCACAAGCCCTCGAACACCAAGGTCGACAAGAAGGTGGAGCCCCCGAAGAGCT
GCGACAAGACCCACACCTGCCCGCCCTGCCCCGCCCCCGAGCTCCTGGGCGGGCCCAG
CGTGTTCCTGTTCCCGCCCAAGCCCAAGGACACGCTCATGATCAGCCGCACCCCCGAG
GTCACCTGCGTGGTGGTCGACGTGAGCCACGAGGACCCCGAGGTGAAGTTCAACTGGT
ACGTCGACGGCGTGGAGGTGCACAACGCCAAGACCAAGCCGCGGGAGGAGCAGTACAA
CTCGACGTACCGCGTCGTGAGCGTGCTGACCGTCCTGCACCAGGACTGGCTCAACGGC
AAGGAGTACAAGTGCAAGGTGAGCAACAAGGCCCTGCCCGCGCCCATCGAGAAGACCA
TCAGCAAGGCCAAGGGGCAGCCCCGGGAGCCGCAGGTGTACACCCTGCCCCCCAGCCG
CGACGAGCTCACGAAGAACCAGGTCAGCCTGACCTGCCTGGTGAAGGGCTTCTACCCC
TCGGACATCGCCGTGGAGTGGGAGAGCAACGGGCAGCCGGAGAACAACTACAAGACCA
CCCCGCCCGTCCTCGACAGCGACGGCAGCTTCTTCCTGTACAGCAAGCTGACGGTGGA
CAAGTCGCGGTGGCAGCAGGGCAACGTGTTCAGCTGCAGCGTCATGCACGAGGCCCTC
CACAACCACTACACCCAGAAGAGCCTGAGCCTGAGCCCCGGGAAGCATCATCATCATC
ATCATTGACC**AGATCTTTCTGACATTTCTGACATTTCTGACATTTCTGACATTTCTGA
CATTTCTGACATTTCTGACATTTCTGACATTTCTGACATTTCTGACATATGCATACCA**
*TG*GCCGTGATGGCGCCGCGGACCCTGGTCCTCCTGCTGAGCGGCGCCCTCGCCCTGAC
GCAGACCTGGGCCGGGGACATCCAGATGACCCAGAGCCCGTCGAGCCTGAGCGCCAGC
GTGGGCGACCGGGTCACGATCACCTGCCGCGCGAGCCAGGACGTGAACACCGCCGTGG
CCTGGTACCAGCAGAAGCCCGGGAAGGCCCCCAAGCTCCTGATCTACTCGGCGAGCTT
CCTGTACAGCGGCGTCCCCAGCCGGTTCAGCGGGTCGCGCAGCGGCACCGACTTCACG
CTCACCATCAGCAGCCTGCAGCCGGAGGACTTCGCCACCTACTACTGCCAGCAGCACT
ACACCACGCCCCCCACCTTCGGGCAGGGCACCAAGGTGGAGATCAAGCGGACCGTGGC
CGCCCCAGCGTCTTCATCTTCCCGCCCAGCGACGAGCAGCTGAAGTCGGGCACGGCC
AGCGTGGTGTGCCTCCTGAACAACTTCTACCCCCGCGAGGCGAAGGTCCAGTGGAAGG
TGGACAACGCCCTGCAGAGCGGGAACAGCCAGGAGAGCGTGACCGAGCAGGACTCGAA
GGACAGCACCTACAGCCTCAGCAGCACCCTGACGCTGAGCAAGGCCGACTACGAGAAG
CACAAGGTCTACGCCTGCGAGGTGACCCACCAGGGGCTCTCGAGCCCCGTGACCAAGA
GCTTCAACCGGGGCGAGTGCTGATGACCACTAG

Fig. 22

AAGCTTACCATGGCCGTGATGGCGCCGCGGACCCTGGTCCTCCTGCTGAGCGGCGCCC
TCGCCCTGACGCAGACCTGGGCCGGGCAGGCCTACCTGCAGCAGAGCGGCGCGGAGCT
CGTGCGGCCGGGGGCCTCGGTCAAGATGAGCTGCAAGGCCAGCGGCTACACCTTCACG
AGCTACAACATGCACTGGGTGAAGCAGACCCCGCGCCAGGGGCTGGAGTGGATCGGCG
CCATCTACCCCGGGAACGGCGACACCAGCTACAACCAGAAGTTCAAGGGCAAGGCGAC
CCTGACGGTGGACAAGTCGAGCAGCACCGCCTACATGCAGCTCAGCAGCCTGACCTCG
GAGGACAGCGCCGTCTACTTCTGCGCCCGGGTGGTGTACTACAGCAACAGCTACTGGT
ACTTCGACGTCTGGGGGACCGGCACGACCGTGACCGTGAGCGGGCCCAGCGTCTTCCC
CCTGGCCCCCTCGAGCAAGAGCACCAGCGGCGGCACGGCGGCCCTCGGGTGCCTGGTG
AAGGACTACTTCCCCGAGCCCGTGACCGTCAGCTGGAACTCGGGCGCCCTGACCAGCG
GGGTGCACACCTTCCCGGCCGTGCTCCAGAGCAGCGGCCTGTACAGCCTGAGCTCGGT
CGTGACGGTGCCCAGCAGCAGCCTCGGGACCCAGACCTACATCTGCAACGTCAACCAC
AAGCCCAGCAACACCAAGGTGGACAAGAAGGCGGAGCCCAAGTCGTGCGACAAGACGC
ACACCTGCCCGCCCTGCCCCGCCCCCGAGCTGCTGGGCGGCCCGAGCGTGTTCCTCTT
CCCGCCCAAGCCCAAGGACACCCTGATGATCAGCCGCACCCCCGAGGTCACGTGCGTG
GTGGTCGACGTGAGCCACGAGGACCCCGAGGTGAAGTTCAACTGGTACGTCGACGGGG
TGGAGGTGCACAACGCCAAGACCAAGCCCCGGGAGGAGCAGTACAACAGCACCTACCG
CGTCGTGAGCGTGCTGACCGTCCTCCACCAGGACTGGCTGAACGGCAAGGAGTACAAG
TGCAAGGTGTCGAACAAGGCCCTGCCGGCCCCCATCGAGAAGACGATCAGCAAGGCGA
AGGGGCAGCCCCGGGAGCCCCAGGTGTACACCCTCCCGCCCAGCCGCGACGAGCTGAC
CAAGAACCAGGTCAGCCTGACCTGCCTCGTGAAGGGCTTCTACCCCAGCGACATCGCC
GTGGAGTGGGAGTCGAACGGGCAGCCCGAGAACAACTACAAGACGACCCCGCCCGTCC
TGGACAGCGACGGCAGCTTCTTCCTGTACAGCAAGCTCACCGTGGACAAGAGCCGGTG
GCAGCAGGGCAACGTGTTCAGCTGCTCGGTCATGCACGAGGCCCTGCACAACCACTAC
ACCCAGAAGAGCCTGAGCCTCAGCCCCGGGAAGCATCATCATCATCATCATTGACCAT
GCATTTCTGACATTTCTGACATTTCTGACATTTCTGACATTTCTGACATTTCTGACAT
TTCTGACATTTCTGACATTTCTGACATTTCTGACATAGATCTACCATGGCCGTGATGG
CGCCGCGGACCCTGGTCCTCCTGCTGAGCGGCGCCCTCGCCCTGACGCAGACCTGGGC
CGGGCAGATCGTGCTGAGCCAGTCGCCGGCCATCCTCAGCGCGAGCCCCGGCGAGAAG
GTCACCATGACGTGCCGGGCCAGCAGCTCGGTGAGCTACATGCACTGGTACCAGCAGA
AGCCCGGGAGCAGCCCCAAGCCGTGGATCTACGCCCCCAGCAACCTGGCCTCGGGCGT
GCCCGCGCGCTTCAGCGGGAGCGGCAGCGGGACCAGCTACAGCCTGACCATCTCGCGG
GTCGAGGCCGAGGACGCCGCCACCTACTACTGCCAGCAGTGGAGCTTCAACCCGCCCA
CGTTCGGCGCCGGCACCAAGCTCGAGCTGAAGCGCACCGTGGCGGCCCCCAGCGTGTT
CATCTTCCCGCCCAGCGACGAGCAGCTGAAGAGCGGGACCGCCTCGGTCGTGTGCCTC
CTGAACAACTTCTACCCCCGGGAGGCCAAGGTGCAGTGGAAGGTCGACAACGCGCTGC
AGAGCGGCAACAGCCAGGAGAGCGTGACGGAGCAGGACAGCAAGGACAGCACCTACTC
GCTCAGCAGCACCCTGACCCTGAGCAAGGCCGACTACGAGAAGCACAAGGTGTACGCC
TGCGAGGTCACGCACCAGGGGCTCAGCTCGCCCGTGACCAAGAGCTTCAACCGCTGAC
CACTAGT

Fig. 25

AAGCTTACCATGGCCGTGATGGCGCCGCGGACCCTGGTCCTCCTGCTGAGCGGCGCCC
TCGCCCTGACGCAGACCTGGGCCGGGCAGGTGCAGCTGAAGCAGAGCGGCCCGGGGCT
CGTCCAGCCCTCGCAGAGCCTGAGCATCACCTGCACGGTGAGCGGCTTCAGCCTGACC
AACTACGGGGTGCACTGGGTCCGGCAGTCGCCCGGCAAGGGGCTCGAGTGGCTGGGCG
TGATCTGGAGCGGCGGGAACACCGACTACAACACCCCCTTCACGAGCCGCCTGAGCAT
CAACAAGGACAACAGCAAGTCGCAGGTGTTCTTCAAGATGAACAGCCTCCAGAGCAAC
GACACCGCCATCTACTACTGCGCGCGGGCCCTGACCTACTACGACTACGAGTTCGCCT
ACTGGGGCCAGGGGACCCTGGTCACGGTGAGCGCCGCGAGCACCAAGGGCCCGAGCGT
GTTCCCCCTCGCCCCCTCGAGCAAGAGCACCAGCGGCGGGACCGCCGCCCTGGGCTGC
CTGGTCAAGGACTACTTCCCCGAGCCGGTGACGGTGAGCTGGAACTCGGGGGCCCTCA
CCAGCGGCGTCCACACCTTCCCCGCGGTGCTGCAGAGCAGCGGGCTGTACAGCCTCAG
CTCGGTGGTCACCGTGCCCAGCAGCAGCCTGGGCACGCAGACCTACATCTGCAACGTG
AACCACAAGCCCAGCAACACCAAGGTCGACAAGCGCGTGGAGCCGAAGTCGCCCAAGA
GCTGCGACAAGACCCACACGTGCCCGCCCTGCCCCGCCCCGAGCTGCTCGGCGGGCC
CAGCGTGTTCCTGTTCCCGCCCAAGCCCAAGGACACCCTGATGATCAGCCGGACCCCC
GAGGTCACCTGCGTGGTGGTCGACGTGAGCCACGAGGACCCGGAGGTGAAGTTCAACT
GGTACGTCGACGGCGTGGAGGTGCACAACGCCAAGACGAAGCCCCGCGAGGAGCAGTA
CAACAGCACCTACCGGGTCGTGTCGGTGCTCACCGTCCTGCACCAGGACTGGCTGAAC
GGGAAGGAGTACAAGTGCAAGGTGAGCAACAAGGCCCTCCCCGCGCCCATCGAGAAGA
CCATCAGCAAGGCCAAGGGCCAGCCGCGCGAGCCCCAGGTGTACACGCTGCCCCCCAG
CCGGGACGAGCTGACCAAGAACCAGGTCAGCCTCACCTGCCTGGTGAAGGGGTTCTAC
CCGTCGGACATCGCCGTGGAGTGGGAGAGCAACGGCCAGCCCGAGAACAACTACAAGA
CCACGCCCCCGGTCCTGGACAGCGACGGCAGCTTCTTCCTCTACAGCAAGCTGACCGT
GGACAAGAGCCGCTGGCAGCAGGGGAACGTGTTCTCGTGCAGCGTCATGCACGAGGCC
CTGCACAACCACTACACCCAGAAGAGCCTCAGCCTGAGCCCCGGCAAGCATCATCATC
ATCATCATTGACCATGCATTTCTGACATTTCTGACATTTCTGACATTTCTGACATTTC
TGACATTTCTGACATTTCTGACATTTCTGACATTTCTGACATTTCTGACATAGATCTA
CCATGGCCGTGATGGCGCCGCGGACCCTGGTCCTCCTGCTGAGCGGCGCCCTCGCCCT
GACGCAGACCTGGGCCGGGGACATCCTGCTCACCCAGAGCCCGGTGATCCTGTCGGTC
AGCCCCGGCGAGCGGGTGAGCTTCAGCTGCCGCGCCAGCCAGTCGATCGGGACGAACA
TCCACTGGTACCAGCAGCGGACCAACGGCAGCCCCGCCTGCTCATCAAGTACGCGAG
CGAGAGCATCAGCGGGATCCCCTCGCGGTTCAGCGGCAGCGGGAGCGGCACCGACTTC
ACCCTGAGCATCAACAGCGTGGAGTCGGAGGACATCGCCGACTACTACTGCCAGCAGA
ACAACAACTGGCCGACGACCTTCGGCGCCGGGACCAAGCTGGAGCTCAAGCGCACCGT
CGCCGCGCCCAGCGTGTTCATCTTCCCGCCCAGCGACGAGCAGCTGAAGAGCGGCACG
GCCAGCGTGGTCTGCCTGCTCAACAACTTCTACCCCGGGAGGCCAAGGTGCAGTGGA
AGGTGGACAACGCCCTGCAGTCGGGGAACAGCCAGGAGAGCGTCACCGAGCAGGACAG
CAAGGACAGCACCTACAGCCTGTCGAGCACCCTCACGCTGAGCAAGGCCGACTACGAG
AAGCACAAGGTGTACGCGTGCGAGGTGACCCACCAGGGCCTGAGCAGCCCCGTCACCA
AGTCGTTCAACCGCGGCGCCTGACCACTAGT

Fig. 26

AAGCTTACCATGGCCGTGATGGCGCCGCGGACCCTGGTCCTCCTGCTGAGCGGCGCCC
TCGCCCTGACGCAGACCTGGGCCGGGGAGGTGCAGCTGGTCGAGAGCGGCGGGGGCCT
CGTGCAGCCGGGCGGGTCGCTGCGGCTGAGCTGCGCCGCGAGCGGGTTCAACATCAAG
GACACCTACATCCACTGGGTGCGCCAGGCCCCCGGCAAGGGCCTCGAGTGGGTCGCCC
GGATCTACCCCACGAACGGGTACACCCGCTACGCCGACAGCGTGAAGGGCCGGTTCAC
CATCAGCGCGGACACCTCGAAGAACACGGCCTACCTGCAGATGAACAGCCTGCGCGCC
GAGGACACCGCCGTGTACTACTGCAGCCGGTGGGCGGCGACGGGTTCTACGCCATGG
ACTACTGGGGCAGGGCACCCTCGTCACCGTGAGCAGCGCGTCGACGAAGGGGCCCAG
CGTGTTCCCGCTGGCCCCAGCAGCAAGAGCACCAGCGGCGGGACCGCCGCCCTGGGC
TGCCTCGTCAAGGACTACTTCCCCGAGCCCGTGACCGTGTCGTGGAACAGCGGCGCGC
TGACGAGCGGGGTCCACACCTTCCCGGCCGTGCTGCAGAGCAGCGGCCTCTACTCGCT
GAGCAGCGTGGTCACCGTGCCCAGCAGCAGCCTGGGGACCCAGACGTACATCTGCAAC
GTGAACCACAAGCCCTCGAACACCAAGGTCGACAAGAAGGTGGAGCCCCCGAAGAGCT
GCGACAAGACCCACACCTGCCCGCCCTGCCCCGCCCCCGAGCTCCTGGGCGGGCCCAG
CGTGTTCCTGTTCCCGCCCAAGCCCAAGGACACGCTCATGATCAGCCGCACCCCCGAG
GTCACCTGCGTGGTGGTCGACGTGAGCCACGAGGACCCCGAGGTGAAGTTCAACTGGT
ACGTCGACGGCGTGGAGGTGCACAACGCCAAGACCAAGCCGCGGGAGGAGCAGTACAA
CTCGACGTACCGCGTCGTGAGCGTGCTGACCGTCCTGCACCAGGACTGGCTCAACGGC
AAGGAGTACAAGTGCAAGGTGAGCAACAAGGCCCTGCCCGCGCCCATCGAGAAGACCA
TCAGCAAGGCCAAGGGGCAGCCCCGGGAGCCGCAGGTGTACACCCTGCCCCCCAGCCG
CGACGAGCTCACGAAGAACCAGGTCAGCCTGACCTGCCTGGTGAAGGGCTTCTACCCC
TCGGACATCGCCGTGGAGTGGGAGAGCAACGGGCAGCCGGAGAACAACTACAAGACCA
CCCCGCCCGTCCTCGACAGCGACGGCAGCTTCTTCCTGTACAGCAAGCTGACGGTGGA
CAAGTCGCGGTGGCAGCAGGGCAACGTGTTCAGCTGCAGCGTCATGCACGAGGCCCTC
CACAACCACTACACCCAGAAGAGCCTGAGCCTGAGCCCCGGGAAGCATCATCATCATC
ATCATTGACCATGCATTTCTGACATTTCTGACATTTCTGACATTTCTGACATTTCTGA
CATTTCTGACATTTCTGACATTTCTGACATTTCTGACATTTCTGACATAGATCTACCA
TGGCCGTGATGGCGCCGCGGACCCTGGTCCTCCTGCTGAGCGGCGCCCTCGCCCTGAC
GCAGACCTGGGCCGGGGACATCCAGATGACCCAGAGCCCGTCGAGCCTGAGCGCCAGC
GTGGGCGACCGGGTCACGATCACCTGCCGCGCGAGCCAGGACGTGAACACCGCCGTGG
CCTGGTACCAGCAGAAGCCCGGGAAGGCCCCCAAGCTCCTGATCTACTCGGCGAGCTT
CCTGTACAGCGGCGTCCCCAGCCGGTTCAGCGGGTCGCGCAGCGGCACCGACTTCACG
CTCACCATCAGCAGCCTGCAGCCGGAGGACTTCGCCACCTACTACTGCCAGCAGCACT
ACACCACGCCCCCCACCTTCGGGCAGGGCACCAAGGTGGAGATCAAGCGGACCGTGGC
CGCCCCCAGCGTCTTCATCTTCCCGCCCAGCGACGAGCAGCTGAAGTCGGGCACGGCC
AGCGTGGTGTGCCTCCTGAACAACTTCTACCCCGCGAGGCGAAGGTCCAGTGGAAGG
TGGACAACGCCCTGCAGAGCGGGAACAGCCAGGAGAGCGTGACCGAGCAGGACTCGAA
GGACAGCACCTACAGCCTCAGCAGCACCCTGACGCTGAGCAAGGCCGACTACGAGAAG
CACAAGGTCTACGCCTGCGAGGTGACCCACCAGGGGCTCTCGAGCCCCGTGACCAAGA
GCTTCAACCGGGGCGAGTGCTGATGACCACTAG

Fig. 27

RNA-CODED ANTIBODY

RELATED APPLICATIONS

This application is a national stage application (under 35 U.S.C. § 371) of PCT/EP2008/000081, filed Jan. 8, 2008, which claims benefit of German application 102007001370.3, filed Jan. 9, 2007.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 22122000.txt. The size of the text file is 54,741 bytes, and the text file was created on Jan. 10, 2013.

The present application describes an antibody-coding, non-modified or modified RNA and the use thereof for expression of this antibody, for the preparation of a pharmaceutical composition, in particular a passive vaccine, for treatment of tumours and cancer diseases, cardiovascular diseases, infectious diseases, autoimmune diseases, virus diseases and monogenetic diseases, e.g. also in gene therapy. The present invention furthermore describes an in vitro transcription method, in vitro methods for expression of this antibody using the RNA according to the invention and an in vivo method.

The occurrence of tumours and cancer diseases is, alongside cardiovascular and infectious diseases, one of the most frequent causes of death in modern societies and is associated with usually considerable costs during the therapy and subsequent rehabilitation measures. The treatment of tumours and cancer diseases depends greatly, for example, on the nature of the tumour which occurs and at present conventionally is undertaken by using radio- or chemotherapy, in addition to invasive interventions. However, these therapies represent an exceptional burden on the immune system, and in some cases can be employed to only a limited extent. Furthermore, these therapy forms usually require long pauses between the individual treatments for regeneration of the immune system. In recent years, alongside these "conventional methods", molecular biology programmes in particular have emerged as promising for the treatment or for assisting these therapies.

An example of these molecular biology methods comprises the use of antibodies or immunoglobulins as essential effectors of the immune system. Antibodies or immunoglobulins can be generated either in vitro by using known molecular biology methods or by the immune system of the organism itself to be treated. The immune system of higher vertebrates thus has two separate functions of the immune system: the innate immune system, which reacts non-specifically to pathogens (e.g. by macrophage-mediated phagocytosis) and the adaptive immune system, which reacts specifically to pathogens by means of specialized effector cells (e.g. B and T cells). The antibodies or immunoglobulins which are secreted by plasma cells during an immune response are part of this adaptive immune system. Together with the complement system, they form the humoral branch of the immune response.

Alongside their essential importance for the immune system in higher vertebrates, precisely because of their high affinity and specificity for a particular antigen antibodies are an outstanding means both in biochemical and molecular biology research and in diagnostics and medical uses. Thus, antibodies are capable of binding specifically to their target structures (e.g. antigens, which substantially comprise proteins, peptides, in some cases lipids, carbohydrates etc.) and of thereby blocking (inhibiting) or, where appropriate, labelling these. They can moreover activate the immune system by means of their Fc part, so that the labelled cells are destroyed. Over 100 therapeutic antibodies are currently to be found in clinical studies. Antibodies which can be employed in cancer therapy play by far the greatest role in this context. Most of the antibodies prepared for this at present are monoclonal antibodies which originate originally, for example, from the mouse. In order to prevent an immune reaction against such monoclonal antibodies, at present chiefly humanized or human antibodies are employed for therapy (cf. David Male; "Immunologie auf einen Blick [Immunology at a Glance]", 1st German edition, 2005, Elsevier-Urban & Fischer Verlag; Charles A. Janeway, Paul Travers, Mark Walport and Mark Shlomchik, Immunobiology, 5th edition, 2001, Garland Publishing; Dissertation by Christian Klein, Monoklonale Antikorper and rekombinante Antikörperfragmente gegen sekundäre Arzneipflanzenmetabolite [Monoclonal Antibodies and Recombinant Antibody Fragments Against Secondary Medicinal Plant Metabolites], 2004; Andreas Schmiedl and Stefan Dübel, Rekombinante Antikörper & Phagen-Display [Recombinant Antibody & Phage Display], 2004, Molekulare Biotechnologie [Molecular Biotechnology] (Wiley-VCH)).

Antibodies generally can be assigned to the group of immunoglobulins. These immunoglobulins can in turn be differentiated into five main classes of immunoglobulins on the basis of their heavy chain, the IgM (μ), IgD (δ), IgG (γ), IgA (α) and IgE (ε) antibodies, IgG antibodies making up the largest proportion. Immunoglobulins can moreover be differentiated into the isotypes κ and λ on the basis of their light chains.

In spite of their different specificity, antibodies are structurally quite similar in construction. Thus, IgG antibodies typically are built up two identical light and two heavy protein chains which are bonded to one another via disulfide bridges. The light chain comprises the N-terminal variable domain $V_L$ and the C-terminal constant domain $C_L$. The heavy chain of an IgG antibody can be divided into an N-terminal variable domain $V_H$ and three constant domains $C_H1$, $C_H2$ and $C_H3$ (cf. FIG. 1). While the amino acid sequence is largely the same in the region of the constant domains, wide differences in sequence are typically found within the variable domains.

The antibody repertoire of a human comprises about at least $10^{11}$ different antibody specificities. In higher vertebrates, the formation of antibodies takes place naturally in the immune system by somatic recombination. In this context, an organism is indeed theoretically capable of generating an antibody of appropriate specificity against any antigen. However, if each of these antibodies were to be coded by an endogenous gene, they would burst the human genome. Instead, in humans antibody genes are composed of a large number of individual gene segments. The part of the antibody gene which codes for the variable region of a light chain is formed from a V gene segment and a J gene segment. In this context, numerous different V and J segments are available, which can be combined with one another virtually as desired. In this context, the variable region of a heavy chain is composed of three different gene segments. In addition to the V and J segments, additional D segments are also found here. The $V_H$, $D_H$ and $J_H$ segments can likewise be combined with one another virtually as desired to form the variable region of the heavy chain (cf. FIG. 2). The mechanism by which the various gene segments are combined to form complete antibody genes is called immunoglobulin rearrangement or somatic recombination. It takes place exclusively in B lymphocytes at certain times of cell development.

In addition to pure gene rearrangement, further mechanisms for increasing the antibody diversity also exist. Two mechanisms which are accompanied by somatic recombination are first to be mentioned in this context: The junctional diversity in this context describes controlled imprecise joining together of the rearranged gene segments, as a result of which random removal and insertion of nucleotides occurs at the cleavage sites. A further combinatorial diversity results from the possibility of combining a particular rearranged light chain with a particular rearranged heavy chain. Finally, the diversity of antibodies is also additionally increased after successful rearrangement and later activation of B cells, in that an affinity maturation of antibodies occurs due to an increased rate of mutation in the region of the variable regions of activated B cells (somatic hypermutation).

In addition to the formation of antibodies which takes place naturally by the immune system of the particular organism, antibodies can also be generated by molecular biology methods. However, in order to utilize the system elaborated for specification of antibody formation and specification thereof for particular antigens or nucleic acids, the formation of antibodies is at present typically induced in selected organisms by injection of a particular antigen, and the antibody is then isolated from the organism for further use. In this context, the B lymphocytes of the organism are conventionally purified selectively and fused with an immortal myeloma cell to form a hybridoma cell. Those cells which secrete the corresponding antigen-specific antibodies are then determined by selection methods.

In addition to use of hybridoma cells, recombinant preparation of these antibodies with the desired specificity is also possible after isolation and sequencing. Cells which provide the required posttranslational modifications are typically used for this. On the basis of the immune reaction with formation of human anti-mouse antibodies in the human organism in the case of native antibodies produced in the mouse (or in other hosts), chimeric, humanized or human antibodies are preferably prepared here.

After expression, these antibodies, optionally prepared by recombinant methods, can be employed as agents both in biochemical and molecular biology research, and in diagnostics and for medical uses.

In medical uses, however, in many cases antibodies can be employed directly only with difficulty, since these usually have only a very short half-life in vivo and therefore, possibly, cannot reach their target antigen or their target nucleic acid at all. This requires either high active compound concentrations of the desired antibody, or alternative methods which are suitable for providing large amounts of antibodies in vivo.

Such methods include, e.g. molecular medicine methods of gene therapy and genetic vaccination which, when used generally in the therapy and prevention of diseases, have considerable effects on medical practice. Both methods are based on the introduction of nucleic acids into cells or into tissue of the patient and on subsequent processing by the cells or, respectively, tissue of the information coded by the nucleic acids introduced, i.e. expression of the desired polypeptides, e.g. antibodies, in the cells or respectively, the tissue.

The conventional procedure of methods of gene therapy and of genetic vaccination to date is based on the use of DNA to sluice the required genetic information into the cell. Various methods for introducing DNA into cells have been developed in this connection, such as, for example, calcium phosphate transfection, polyprene transfection, protoplast fusion, electroporation, microinjection, lipofection and the use of gene canons, lipofection in particular having emerged as a suitable method.

A further method which has been proposed in particular in the case of genetic vaccination methods is the use of DNA viruses as DNA vehicles. Such viruses have the advantage that because of their infectious properties a very high transfection rate can be achieved. The viruses used are genetically modified, so that no functional infectious particles are formed in the transfected cell. The use of DNA viruses as DNA vehicles, however, has been criticized in recent years because of the risk of recombination of non-active viruses to give active viruses.

The use of DNA as an agent in gene therapy and genetic vaccination or for passive immunization (by passive vaccines), e.g. by using coding sequences for antibodies, may, however, also be less advantageous from some points of view. DNA is degraded only relatively slowly in the bloodstream, so that when (foreign) DNA is used as the coding sequence for a desired protein, a formation of anti-DNA antibodies may occur, which has been confirmed in an animal model in the mouse (Gilkeson et al., J. Clin. Invest. 1995, 95: 1398-1402). The possible persistence of (foreign) DNA in the organism can thus lead to a hyperactivation of the immune system, which as is known results in splenomegaly in mice (Montheith et al., Anticancer Drug Res. 1997, 12(5): 421-432). Furthermore, (foreign) DNA can interact with the host genome, and in particular cause mutations by integration into the host genome. Thus, for example, the (foreign) DNA introduced may be inserted into an intact gene, which represents a mutation which can impede or even completely switch off the function of the endogenous gene. On the one hand enzyme systems which are vital for the cell may be destroyed by such integration events, and on the other hand there is also the danger of a transformation of the cell modified in this way into a degenerated state if a gene which is decisive for regulation of cell growth is modified by the integration of the foreign DNA. With the methods to date of gene therapy and genetic vaccination and also of passive immunization, a risk of development of cancer therefore cannot necessarily be ruled out when (foreign) DNA is used. In this context, passive immunization (by so-called "passive vaccines") is to be strictly differentiated from so-called active immunization. In active immunization, an antigen ("active vaccine") is typically administered, after which the organism forms antibodies against this antigen. Active immunization thus creates a permanent immunization of the organism against the particular antigen, which can be associated with the disadvantages described above. In passive immunization, in contrast, only an antiserum or the purified antibody itself ("passive vaccine") is administered to the organism. The coding sequence for the antibody can likewise be administered, as described above, as a so-called passive vaccine for passive immunization.

Summarizing, in the prior art there is an increased demand for and a considerable interest in agents which are suitable for employing antibodies effectively in vivo, in particular for providing increased active compound amounts of antibodies in vivo, without the risks hitherto associated with the use of DNA.

This object is achieved according to the invention by the use of an RNA (sequence) for intracellular expression of an antibody, wherein the RNA (sequence) codes for an antibody or contains at least one coding region, which codes for at least one antibody, respectively. In connection with the present invention, an antibody-coding RNA according to the invention includes any RNA which encodes an antibody. More generally, the RNA of the present invention (directed to intracellular expression) contains at least one coding region, wherein the at least one coding region codes for at least one antibody. If more than one coding region is contained in the RNA molecule of the invention, the second, third etc. coding region may code for antibodies as well, which may be the same or distinct from the first antibody coding region. In a preferred embodiment, the inventive RNA contains at least two coding regions, all of them coding for identical or distinct antibodies. In still another embodiment of the present invention, an inventive RNA may code for more than one antibody within the same coding region. In summary, the inventive RNA may be mono-, bi- or multicistronic, codes for at least one antibody.

The antibody-coding RNA according to the invention can be single-stranded or double-stranded, linear or circular, or in particular in the form of mRNA. The antibody-coding RNA according to the invention is particularly preferably in the form of single-stranded RNA, even more preferably in the form of mRNA.

An antibody-coding RNA according to the invention preferably has a length of from 50 to 15,000 nucleotides, more preferably a length of from 50 to 10,000 nucleotides, even more preferably a length of from 500 to 10,000 nucleotides and most preferably a length of from 500 to 7,000, 500 to 5,000 or 700 to 3,000 nucleotides.

In connection with the present invention, the antibodies coded by the RNA according to the invention can be chosen from all antibodies, e.g. from all antibodies which are generated by recombinant methods or are naturally occurring and are known to a person skilled in the art from the prior art, in particular antibodies which are (can be) employed for therapeutic purposes or for diagnostic or for research purposes or have been found with particular diseases, e.g. cancer diseases, infectious diseases etc.

In the context of the present invention, antibodies which are coded by an RNA according to the invention typically include all antibodies (described above) which are known to a person skilled in the art, e.g. naturally occurring antibodies or antibodies generated in a host organism by immunization, antibodies prepared by recombinant methods which have been isolated and identified from naturally occurring antibodies or antibodies generated in a host organism by (conventional) immunization or have been generated with the aid of molecular biology methods, as well as chimeric antibodies, human antibodies, humanized antibodies, bispecific antibodies, intrabodies, i.e. antibodies expressed in cells and possibly localized in particular cell compartments, and fragments of the abovementioned antibodies. Insofar, the term antibody is to be understood in its broadest meaning. In this context, antibodies in general typically comprise a light chain and a heavy chain, both of which have variable and constant domains. The light chain comprises the N-terminal variable domain $V_L$ and the C-terminal constant domain $C_L$. The heavy chain of an IgG antibody, in contrast, can be divided into an N-terminal variable domain $V_H$ and three constant domains $C_H1$, $C_H2$ and $C_H3$ (cf. FIG. 1).

RNA molecules according to the invention can also be prepared on the basis of polyclonal antibodies or, as an antibody-coding RNA cocktail, can have a polyclonal character. In the context of this invention, polyclonal antibodies are typically mixtures of antibodies against a specific antigen or immunogen or epitope of a protein which have been generated by immunization of a host organism, for example mammals, i.e. animals, including cattle, pigs, dogs, cats, donkeys, monkeys, including rodents, e.g. mice, hamsters, rabbits etc., and man. Polyclonal antibodies conventionally recognize different epitopes or regions of the same specific antigen, each of these epitopes in turn being capable of generating a clone of B lymphocytes which produces an antibody against this epitope. From such polyclonal antibodies or from the antibody sera obtained from the host organism, the individual antibodies specific against the particular epitopes can be obtained by individualization to monoclonal antibodies. The present invention accordingly also provides RNA which codes for a monoclonal antibody obtained by individualization of polyclonal antibodies.

Monoclonal antibodies in the context of this invention are therefore typically antibodies which are specific for a particular antigen or epitope (of a protein), i.e. bind this antigen or epitope (of a protein) with a high affinity, and conventionally are expressed by a hybridoma cell. For the preparation of such monoclonal antibodies, the corresponding antigen or immunogen or epitope of a protein is typically injected at least once, but typically several times, into a host organism as described here, as a result of which the immune system of the host organism, in the presence of suitable adjuvants, is preferably stimulated to antibody production via activation of correspondingly specific B cells. The B lymphocytes are then conventionally selectively purified from the spleen or other organs or fluids suitable for this from an animal immunized in this manner, and are fused with an immortal myeloma cell to give the so-called hybridoma cell. After selection methods and cloning of the hybridomas or hybridoma cells formed, those clones which secernate, i.e. express and secrete, antibodies of the desired specificity can be determined. These clones can be isolated and sequenced with known molecular biology methods. The data obtained from such a sequencing can serve further in a nucleic acid synthesis for generation of synthetic DNA sequences or for screening a cDNA library and isolation of the cDNA fragments and generation of a DNA or nucleic acid template for in vitro or in vivo synthesis of the RNA according to the invention which codes for an antibody. Where appropriate, the RNA contained in the hybridomas can also be isolated, for example by fractionation, and subsequently the RNA molecules according to the invention which code for the hybridoma antibody can be purified by methods known to the person skilled in the art.

Nevertheless, RNA molecules which code for non-human monoclonal or polyclonal antibody, e.g. murine monoclonal antibodies or monoclonal antibodies from other, as described here, non-human host organisms or hybridoma cells are of only limited suitability for therapeutic use in humans, since in the human organism itself they conventionally cause an immune reaction with formation of human anti-antibodies directed against these non-human host antibodies. As a result, such non-human monoclonal or polyclonal antibodies as a rule can be administered to a person only a single time. To by-pass this problem, RNA molecules which code for chimeric, humanized and human antibodies can also be provided according to the invention.

Chimeric antibodies in the context of the present invention are preferably antibodies in which the constant domains of an antibody as described here have been replaced by human sequences. Preferably, chimeric antibodies are formed from monoclonal or polyclonal antibodies as described here.

Humanized antibodies in the context of the present invention are antibodies in which the constant and variable domains described above of the non-human monoclonal or polyclonal antibodies, with the exception of the hypervariable regions, have been replaced by human sequences.

RNA molecules which code for human antibodies, i.e. antibodies which have completely human sequences, that is to say in the constant and variable domains, including the hypervariable regions, can furthermore be used in the context of the present invention. Such RNA molecules which code for human antibodies can be isolated from human tissue or originate from immunized host organisms as described here, e.g. mice, which are then transgenic for the human IgG gene locus. RNA molecules which code for human antibodies and have been isolated by means of phage display and cloned with the aid of molecular biology methods are furthermore provided (see below).

Antibodies which are coded by RNAs according to the invention particularly preferably include so-called full length antibodies, i.e. antibodies which comprise both the complete heavy and the complete light chains, as described above.

RNAs which alternatively code for one or more antibody fragment(s) of the antibodies described above, instead of the corresponding full length antibody, can furthermore be provided in the context of the present invention. Examples of such antibody fragments are any antibody fragments known to a person skilled in the art, e.g. Fab, Fab', F(ab)$_2$, Fc, Facb, pFc', Fd, and Fv fragments of the abovementioned antibodies etc. A diagram of the structure of such antibody fragments is shown by way of example in FIG. 4. Protein fragments consisting of the minimal binding subunit of antibodies known as single-chain antibodies (scFvs) have excellent binding specificity and affinity for their ligands. In contrast to antibodies, scFvs lack the non-binding regions. Accordingly, RNA encoding scFvs are also encompassed by the present invention.

For example, an Fab (fragment antigen binding) fragment typically comprises the variable and a constant domain of a light and a heavy chain, e.g. the $C_H1$ and the $V_H$ domain of the heavy chain and the complete light chain. The two chains are bonded to one another via a disulfide bridge. An Fab fragment thus conventionally contains the complete antigen-binding region of the original antibody and usually has the same affinity for the antigen, the immunogen or an epitope of a protein. Antibody fragments, as also described above for antibodies, can be prepared with the aid of molecular biology methods. In this context, the DNA sequences which code for the various domains of the antibody fragment are cloned into a specific expression vector. The RNA which codes for these antibody fragments can then be expressed e.g. in suitable host cells. Suitable host cells in connection with the present invention include, inter alia, *E. coli*, yeasts, transgenic plants or mammalian cells etc. (see below). In contrast, an scFv fragment (single chain variable fragment) typically comprises the variable domain of the light and of the heavy chain, which are bonded to one another via an artificial polypeptide linker. In the cloning of such scFv fragments, RNAs which code for a $V_H$ and $V_L$, these being linked to one another by a polypeptide linker, are preferably provided. As a rule, a polypeptide built up from 15-25 glycine, proline and/or serine residues (cf. FIG. 5) or the associated nucleotide sequence is used at the RNA level for the provision of this component.

Furthermore, RNA molecules which code for bispecific antibodies can also be provided in the context of the present invention. Bispecific antibodies in the context of the present invention are preferably antibodies which can act as adaptors between an effector and a corresponding target, e.g. for recruiting effector molecules (e.g. toxins, active compounds (drugs), cytokines etc.), targeting of effector cells (e.g. CTL, NK cells, macrophages, granulocytes etc. (see, for example, review by Kontermann R. E., Acta Pharmacol. Sin, 2005, 26(1): 1-9). In this context, bispecific antibodies are in principle built up such as is described here in general for antibodies, these bispecific antibodies e.g. recognizing two different antigens, immunogens or epitopes, or active compounds, cells, or other molecules (or structures) as mentioned above, i.e. the antigen-binding regions of the antibody are specific for two different molecules (or structures). The various antigens, immunogens or epitopes etc., for example, can thus be brought spatially close. Furthermore, by the binding e.g. of a binding domain or other specificities, the function of the antibody can be extended specifically, e.g. of a binding protein, an immunotoxin etc. Such bispecific antibodies can also be single-chain antibodies (e.g. scFv fragments etc.). Bispecific antibodies can be used, for example, to bring two reaction partners, e.g. two cells, two proteins, a protein and the substrate thereof etc., spatially close in order to promote an interaction between these (e.g. protein-protein interactions, substrate conversions, modifications etc.). Bispecific antibodies are used above all to bring effector cells (such as, for example, T cells, NK cells, macrophages etc.) and target cells (e.g. tumour cells, infected cells etc.) spatially close. Examples of bispecific antibodies can include, without being limited thereto, e.g. those anti-bodies or antibody fragments which bind on the one hand a surface factor as described here, and on the other hand an antigen as described here, preferably a tumour antigen as described here. This includes e.g. CD28 and a tumour antigen (Grosse-Hovest L. et al., 2003, Eur. Immunol. 33(5); 1334-40, (A recombinant bispecific single-chain antibody induces targeted, supra-agonistic CD28-stimulation and tumor cell killing)), CD19 and CD3 (CD19 tumour antigen of B cell lymphoma) etc.

Without being limited thereto, according to the present invention RNAs which code for antibodies inter alia code for those antibodies which bind antigens or specific nucleic acids. Antigens in the context of the present invention are typically molecules which are recognized as exogenous by the immune system and conventionally cause an immune reaction or immune response with the formation of antibodies directed specifically against them. However, antigens can also include, especially in the case of autoimmune diseases, endogenous molecules or structures which are incorrectly recognized as exogenous by the immune system and thereby trigger an immune reaction. Alternatively formulated, antigens are therefore all molecules which are recognized by an antibody in the context of the present invention. Antigens substantially comprise proteins, peptides or epitopes of these proteins or peptides. In this context, epitopes (also called "antigenic determinants") are typically small regions (molecular sections) lying on the surface of such protein or peptide structures and having a length of from 5 to 15, in rare case also to 25, preferably 6 to 9 amino acids. Antigens can furthermore also include lipids, carbohydrates etc. In the context of the present invention, antigens also include, for example, so-called immunogens, i.e. antigens which lead to an immunity of the organism transfected therewith. Antigens by way of example include, without being limited thereto, surface antigens of cells, tumour antigens etc. For example, according to the present invention antibodies can bind the following antigens (which typically occur in vertebrates), e.g. tumour-specific surface antigens (TSSA), e.g. 5T4, α5β1-integrin, 707-AP, AFP, ART-4, B7H4, BAGE, β-catenin/m, Bcr-abl, MN/C IX-antigen, CA125, CAMEL, CAP-1, CASP-8, CD4, CD19, CD20, CD22, CD25, CDC27/m, CD 30, CD33, CD52, CD56, CD80, CDK4/m, CEA, CT, Cyp-B, DAM, EGFR, ErbB3, ELF2M, EMMPRIN, EpCam, ETV6-AML1, G250, GAGE, GnT-V, Gp100, HAGE, HER-2/neu, HLA-A*0201-R170I, HPV-E7, HSP70-2M, HAST-2, hTERT (or hTRT), iCE, IGF-1R, IL-2R, IL-5, KIAA0205, LAGE, LDLR/FUT, MAGE, MART-1/Melan-A, MART-2/Ski, MC1R, myosin/m, MUC1, MUM-1, -2, -3, NA88-A, NY-ESO1, PAP, proteinase-3, p190 minor bcr-abl, Pml/RARα, PRAMS, PSA, PSM, PSMA, RAGE, RU1 or RU2, SAGE, SART-1 or SART-3, survivin, TEL/AML1, TGFβ, TPI/m, TRP-1, TRP-2, TRP-2/INT2, VEGF and WT1, or sequences, such as e.g. NY-Eso-1 or NY-Eso-B. Tumour antigens can, for example, typically be responsible for metastasing, that is to say dissolving of tumour cells out of their native tissue, transfer into the vascular system (lymph or blood vessel system), exit from the vascular system and colonization in a new tissue. In this context, such tumour antigens which cause modified cell-cell interactions compared with the native state are of interest in particular.

Antibodies encoded by the inventive RNA may also be directed against tumour antigens listed by Table 1 or Table 2. In particular, RNA encoding those antibodies may be used to treat (or, may be used to prepare a medicament to treat, respectively) the cancer diseases given in the last column of Tables 1 and 2.

TABLE 1

Antigens expressed in cancer diseases

| Tumor antigen | Name of tumor antigen | Cancers or cancer diseases related thereto |
| --- | --- | --- |
| 5T4 | | colorectal cancer, gastric cancer, ovarian cancer |
| 707-AP | 707 alanine proline | melanoma |
| 9D7 | | renal cell carcinoma |
| AFP | alpha-fetoprotein | hepatocellular carcinoma, gallbladder cancer, testicular cancer, ovarian cancer, bladder cancer |
| AlbZIP HPG1 | | prostate cancer |
| alpha5beta1-Integrin | | |
| alpha5beta6-Integrin | | colon cancer |
| alpha-methylacyl-coenzyme A racemase | | prostate cancer |
| ART-4 | adenocarcinoma antigen recognized by T cells 4 | lung cancer, head and neck cancer, leukemia, esophageal cancer, gastric cancer, cervical cancer, ovarian cancer, breast cancer, squamous cell carcinoma |
| B7H4 | | ovarian cancer |
| BAGE-1 | B antigen | bladder cancer, head and neck cancer, lung cancer, melanoma, squamous cell carcinoma |
| BCL-2 | | leukemia |
| BING-4 | | melanoma |
| CA 15-3/CA 27-29 | | breast cancer, ovary cancer, lung cancer, prostate cancer |
| CA 19-9 | | gastric cancer, pancreatic cancer, liver cancer, breast cancer, gallbladder cancer, colon cancer, ovary cancer, lung cancer |
| CA 72-4 | | ovarian cancer |
| CA125 | | ovarian cancer, colorectal cancer, gastric cancer, liver cancer, pancreatic cancer, uterus cancer, cervix carcinoma, colon cancer, breast cancer, lung cancer |
| calreticulin | | bladder cancer |
| CAMEL | CTL-recognized antigen on melanoma | melanoma |
| CASP-8 | caspase-8 | head and neck cancer |
| cathepsin B | | breast cancer |
| cathepsin L | | breast cancer |
| CD19 | | B-cell malignancies |
| CD20 | | |
| CD22 | | |
| CD25 | | |
| CD30 | | |
| CD33 | | |
| CD4 | | |
| CD52 | | |
| CD55 | | |
| CD56 | | |
| CD80 | | |
| CEA | carcinoembryonic antigen | gut carcinoma, colorectal cancer, colon cancer, hepatocellular cancer, lung cancer, breast cancer, thyroid cancer, pancreatic cancer, liver cancer cervix cancer, bladder cancer, melanoma |
| CLCA2 | calcium-activated chloride channel-2 | lung cancer |
| CML28 | | leukemia |
| Coactosin-like protein | | pancreatic cancer |
| Collagen XXIII | | prostate cancer |
| COX-2 | | ovarian cancer, breast cancer, colorectal cancer |
| CT-9/BRD6 | bromodomain testis-specific protein | |
| Cten | C-terminal tensin-like protein | prostate cancer |
| cyclin B1 | | |

TABLE 1-continued

Antigens expressed in cancer diseases

| Tumor antigen | Name of tumor antigen | Cancers or cancer diseases related thereto |
|---|---|---|
| cyclin D1 | | ovarian cancer |
| cyp-B | cyclophilin B | bladder cancer, lung cancer, T-cell leukemia, squamous cell carcinoma, |
| CYPB1 | cytochrom P450 1B1 | leukemia |
| DAM-10/MAGE-B1 | differentiation antigen melanoma 10 | melanoma, skin tumors, ovarian cancer, lung cancer |
| DAM-6/MAGE-B2 | differentiation antigen melanoma 6 | melanoma, skin tumors, ovarian cancer, lung cancer |
| EGFR/Her1 | | lung cancer, ovarian cancer, head and neck cancer, colon cancer, pancreatic cancer, breast cancer |
| EMMPRIN | tumor cell-associated extracellular matrix metalloproteinase inducer/ | lung cancer, breast cancer, bladder cancer, ovarian cancer, brain cancer, lymphoma |
| EpCam | epithelial cell adhesion molecule | ovarian cancer, breast cancer, colon cancer, lung cancer |
| EphA2 | ephrin type-A receptor 2 | glioma |
| EphA3 | ephrin type-A receptor 2 | melanoma, sarcoma, lung cancer |
| ErbB3 | | breast cancer |
| EZH2 | (enhancer of Zeste homolog 2) | endometrium cancer, melanoma, prostate cancer, breast cancer |
| FGF-5 | fibroblast growth factor-5 | renal cell carcinoma, breast cancer, prostate cancer |
| FN | fibronectin | melanoma |
| Fra-1 | Fos-related antigen-1 | breast cancer, esophageal cancer, renal cell carcinoma, thyroid cancer |
| G250/CAIX | glycoprotein 250 | leukemia, renal cell carcinoma, head and neck cancer, colon cancer, ovarian cancer, cervical cancer |
| GAGE-1 | G antigen 1 | bladder cancer, lung cancer, sarcoma, melanoma, head and neck cancer |
| GAGE-2 | G antigen 2 | bladder cancer, lung cancer, sarcoma, melanoma, head and neck cancer |
| GAGE-3 | G antigen 3 | bladder cancer, lung cancer, sarcoma, melanoma, head and neck cancer |
| GAGE-4 | G antigen 4 | bladder cancer, lung cancer, sarcoma, melanoma, head and neck cancer |
| GAGE-5 | G antigen 5 | bladder cancer, lung cancer, sarcoma, melanoma, head and neck cancer |
| GAGE-6 | G antigen 6 | bladder cancer, lung cancer, sarcoma, melanoma, head and neck cancer |
| GAGE-7b | G antigen 7b | bladder cancer, lung cancer, sarcoma, melanoma, head and neck cancer |
| GAGE-8 | G antigen 8 | bladder cancer, lung cancer, sarcoma, melanoma, head and neck cancer |
| GDEP | gene differentially expressed in prostate | prostate cancer |
| GnT-V | N-acetylglucosaminyltransferase V | glioma, melanoma |
| gp100 | glycoprotein 100 kDa | melanoma |
| GPC3 | glypican 3 | hepatocellular carcinoma, melanoma |
| HAGE | helicase antigen | bladder cancer |
| HAST-2 | human signet ring tumor-2 | |
| hepsin | | prostate |
| Her2/neu/ErbB2 | human epidermal receptor-2/neurological | breast cancer, bladder cancer, melanoma, ovarian cancer, pancreas cancer, gastric cancer |
| HERV-K-MEL | | melanoma |
| HNE | human neutrophil elastase | leukemia |
| homeobox NKX 3.1 | | prostate cancer |
| HOM-TES-14/SCP-1 | | ovarian cancer |
| HOM-TES-85 | | |
| HPV-E6 | | cervical cancer |
| HPV-E7 | | cervical cancer |
| HST-2 | | gastric cancer |
| hTERT | human telomerase reverse transcriptase | breast cancer, melanoma, lung cancer, ovarian cancer, sarcoma, Non-Hodgkin-lymphoma, acute leukemia |
| iCE | intestinal carboxyl esterase | renal cell carcinoma |
| IGF-1R | | colorectal cancer |
| IL-13Ra2 | interleukin 13 receptor alpha 2 chain | glioblastoma |
| IL-2R | | colorectal cancer |
| IL-5 | | |
| immature laminin receptor | | renal cell carcinoma |
| kallikrein 2 | | prostate cancer |
| kallikrein 4 | | prostate cancer |
| Ki67 | | prostate cancer, breast cancer, Non-Hodgkin-lymphoma, melanoma |
| KIAA0205 | | bladder cancer |
| KK-LC-1 | Kita-kyushu lung cancer antigen 1 | lung cancer |

TABLE 1-continued

Antigens expressed in cancer diseases

| Tumor antigen | Name of tumor antigen | Cancers or cancer diseases related thereto |
|---|---|---|
| KM-HN-1 | | tongue cancer, hepatocellular carcinomas, melanoma, gastric cancer, esophageal, colon cancer, pancreatic cancer |
| LAGE-1 | L antigen | bladder cancer, head and neck cancer, melanoma |
| livin | | bladder cancer, melanoma |
| MAGE-A1 | melanoma antigen-A1 | bladder cancer, head and neck cancer, melanoma, colon cancer, lung cancer, sarcoma, leukemia |
| MAGE-A10 | melanoma antigen-A10 | bladder cancer, head and neck cancer, melanoma, colon cancer, lung cancer, sarcoma, leukemia |
| MAGE-A12 | melanoma antigen-A12 | bladder cancer, head and neck cancer, melanoma, colon cancer, lung cancer, sarcoma, leukemia, prostate cancer, myeloma, brain tumors |
| MAGE-A2 | melanoma antigen-A2 | bladder cancer, head and neck cancer, melanoma, colon cancer, lung cancer, sarcoma, leukemia |
| MAGE-A3 | melanoma antigen-A3 | bladder cancer, head and neck cancer, melanoma, colon cancer, lung cancer, sarcoma, leukemia |
| MAGE-A4 | melanoma antigen-A4 | bladder cancer, head and neck cancer, melanoma, colon cancer, lung cancer, sarcoma, leukemia |
| MAGE-A6 | melanoma antigen-A6 | bladder cancer, head and neck cancer, melanoma, colon cancer, lung cancer, sarcoma, leukemia |
| MAGE-A9 | melanoma-antigen-A9 | bladder cancer, head and neck cancer, melanoma, colon cancer, lung cancer, sarcoma, leukemia |
| MAGE-B1 | melanoma-antigen-B1 | melanoma |
| MAGE-B10 | melanoma-antigen-B10 | melanoma |
| MAGE-B16 | melanoma-antigen-B16 | melanoma |
| MAGE-B17 | melanoma-antigen-B17 | melanoma |
| MAGE-B2 | melanoma-antigen-B2 | melanoma |
| MAGE-B3 | melanoma-antigen-B3 | melanoma |
| MAGE-B4 | melanoma-antigen-B4 | melanoma |
| MAGE-B5 | melanoma-antigen-B5 | melanoma |
| MAGE-B6 | melanoma-antigen-B6 | melanoma |
| MAGE-C1 | melanoma-antigen-C1 | bladder cancer, melanoma |
| MAGE-C2 | melanoma-antigen-C2 | melanoma |
| MAGE-C3 | melanoma-antigen-C3 | melanoma |
| MAGE-D1 | melanoma-antigen-D1 | melanoma |
| MAGE-D2 | melanoma-antigen-D2 | melanoma |
| MAGE-D4 | melanoma-antigen-D4 | melanoma |
| MAGE-E1 | melanoma-antigen-E1 | bladder cancer, melanoma |
| MAGE-E2 | melanoma-antigen-E2 | melanoma |
| MAGE-F1 | melanoma-antigen-F1 | melanoma |
| MAGE-H1 | melanoma-antigen-H1 | melanoma |
| MAGEL2 | MAGE-like 2 | melanoma |
| mammaglobin A | | breast cancer |
| MART-1/Melan-A | melanoma antigen recognized by T cells-1/melanoma antigen A | melanoma |
| MART-2 | melanoma antigen recognized by T cells-2 | melanoma |
| matrix protein 22 | | bladder cancer |
| MC1R | melanocortin 1 receptor | melanoma |
| M-CSF | macrophage colony-stimulating factor gene | ovarian cancer |
| mesothelin | | ovarian cancer |
| MG50/PXDN | | breast cancer, glioblastoma, melanoma |
| MMP 11 | M-phase phosphoprotein 11 | leukemia |
| MN/CA IX-antigen | | renal cell carcinoma |
| MRP-3 | multidrug resistance-associated protein 3 | lung cancer |
| MUC1 | mucin 1 | breast cancer |
| MUC2 | mucin 2 | breast cancer, ovarian cancer, pancreatic cancer |
| NA88-A | NA cDNA clone of patient M88 | melanoma |
| N-acetylglucos-aminyltransferase-V | | |
| Neo-PAP | Neo-poly(A) polymerase | |
| NGEP | | prostate cancer |
| NMP22 | | bladder cancer |
| NPM/ALK | nucleophosmin/anaplastic lymphoma kinase fusion protein | |
| NSE | neuron-specific enolase | small cell cancer of lung, neuroblastoma, Wilm' tumor, melanoma, thyroid cancer, kidney cancer, testicle cancer, pancreas cancer |
| NY-ESO-1 | New York esophageous 1 | bladder cancer, head and neck cancer, melanoma, sarcoma, B-lymphoma, hepatoma, pancreatic cancer, ovarian cancer, breast cancer |
| NY-ESO-B | | |
| OA1 | ocular albinism type 1 protein | melanoma |
| OFA-iLRP | oncofetal antigen-immature laminin receptor | leukemia |

TABLE 1-continued

Antigens expressed in cancer diseases

| Tumor antigen | Name of tumor antigen | Cancers or cancer diseases related thereto |
|---|---|---|
| OGT | O-linked N-acetylglucosamine transferase gene | |
| OS-9 | | |
| osteocalcin | | prostate cancer |
| osteopontin | | prostate cancer, breast cancer, ovarian cancer |
| p15 | protein 15 | |
| p15 | | melanoma |
| p190 minor bcr-abl | | |
| p53 | | |
| PAGE-4 | prostate GAGE-like protein-4 | prostate cancer |
| PAI-1 | plasminogen acitvator inhibitor 1 | breast cancer |
| PAI-2 | plasminogen acitvator inhibitor 2 | breast cancer |
| PAP | prostate acic phosphatase | prostate cancer |
| PART-1 | | prostate cancer |
| PATE | | prostate cancer |
| PDEF | | prostate cancer |
| Pim-1-Kinase | | |
| Pin1 | Propyl isomerase | prostate cancer |
| POTE | | prostate cancer |
| PRAME | preferentially expressed antigen of melanoma | melanoma, lung cancer, leukemia, head and neck cancer, renal cell carcinoma, sarcoma |
| prostein | | prostate cancer |
| proteinase-3 | | |
| PSA | prostate-specific antigen | prostate cancer |
| PSCA | | prostate cancer |
| PSGR | | prostate cancer |
| PSM | | |
| PSMA | prostate-specific membrane antigen | prostate cancer |
| RAGE-1 | renal antigen | bladder cancer, renal cancer, sarcoma, colon cancer |
| RHAMM/CD168 | receptor for hyaluronic acid mediated motility | leukemia |
| RU1 | renal ubiquitous 1 | bladder cancer, melanoma, renal cancer |
| RU2 | renal ubiquitous 1 | bladder cancer, melanoma, sarcoma, brain tumor, esophagel cancer, renal cancer, colon cancer, breast cancer |
| S-100 | | melanoma |
| SAGE | sarcoma antigen | |
| SART-1 | squamous antigen rejecting tumor 1 | esophageal cancer, head and neck cancer, lung cancer, uterine cancer |
| SART-2 | squamous antigen rejecting tumor 1 | head and neck cancer, lung cancer, renal cell carcinoma, melanoma, brain tumor |
| SART-3 | squamous antigen rejecting tumor 1 | head and neck cancer, lung cancer, leukemia, melanoma, esophageal cancer |
| SCC | squamous cell carcinoma antigen | lung cancer |
| Sp17 | sperm protein 17 | multiple myeloma |
| SSX-1 | synovial sarcoma X breakpoint 1 | hepatocellular cell carcinom, breast cancer |
| SSX-2/HOM-MEL-40 | synovial sarcoma X breakpoint 2 | breast cancer |
| SSX-4 | synovial sarcoma X breakpoint 4 | bladder cancer, hepatocellular cell carcinoma, breast cancer |
| STAMP-1 | | prostate cancer |
| STEAP | six transmembrane epithelial antigen prostate | prostate cancer |
| survivin | | bladder cancer |
| survivin-2B | intron 2-retaining survivin | bladder cancer |
| TA-90 | | melanoma |
| TAG-72 | | prostate carcinoma |
| TARP | | prostate cancer |
| TGFb | TGFbeta | |
| TGFbRII | TGFbeta receptor II | |
| TGM-4 | prostate-specific transglutaminase | prostate cancer |
| TRAG-3 | taxol resistant associated protein 3 | breast cancer, leukemia, and melanoma |
| TRG | testin-related gene | |
| TRP-1 | tyrosine related protein 1 | melanoma |
| TRP-2/6b | TRP-2/novel exon 6b | melanoma, glioblastoma |
| TRP-2/INT2 | TRP-2/intron 2 | melanoma, glioblastoma |
| Trp-p8 | | prostate cancer |
| Tyrosinase | | melanoma |
| UPA | urokinase-type plasminogen activator | breast cancer |
| VEGF | vascular endothelial growth factor | |
| VEGFR-2/FLK-1 | vascular endothelial growth factor receptor-2 | |
| WT1 | Wilm' tumor gene | gastric cancer, colon cancer, lung cancer, breast cancer, ovarian cancer, leukemia |

TABLE 2

Mutant antigens expressed in cancer diseases

| Mutant antigen | Name of mutant antigen | Cancers or cancer diseases related thereto |
|---|---|---|
| alpha-actinin-4/m | | lung carcinoma |
| ARTC1/m | | melanoma |
| bcr/abl | breakpoint cluster region-Abelson fusion protein | CML |
| beta-Catenin/m | beta-Catenin | melanoma |
| BRCA1/m | | breast cancer |
| BRCA2/m | | breast cancer |
| CASP-5/m | | colorectal cancer, gastric cancer, endometrial carcinoma |
| CASP-8/m | | head and neck cancer, squamous cell carcinoma |
| CDC27/m | cell-division-cycle 27 | |
| CDK4/m | cyclin-dependent kinase 4 | melanoma |
| CDKN2A/m | | melanoma |
| CML66 | | CML |
| COA-1/m | | colorectal cancer |
| DEK-CAN | fusion protein | AML |
| EFTUD2/m | | melanoma |
| ELF2/m | Elongation factor 2 | lung squamous cell carcinoma |
| ETV6-AML1 | Ets variant gene6/acute myeloid leukemia 1 gene fusion protein | ALL |
| FN1/m | fibronectin 1 | melanoma |
| GPNMB/m | | melanoma |
| HLA-A*0201-R170I | arginine to isoleucine exchange at residue 170 of the alpha-helix of the alpha2-domain in the HLA-A2 gene | renal cell carcinoma |
| HLA-A11/m | | melanoma |
| HLA-A2/m | | renal cell carcinoma |
| HSP70-2M | heat shock protein 70-2 mutated | renal cell carcinoma, melanoma, neuroblastoma |
| KIAA0205/m | | bladder tumor |
| K-Ras/m | | pancreatic carcinoma, colorectal carcinoma |
| LDLR-FUT | LDR-Fucosyltransferase fusion protein | melanoma |
| MART2/m | | melanoma |
| ME1/m | | non-small cell lung carcinoma |
| MUM-1/m | melanoma ubiquitous mutated 1 | melanoma |
| MUM-2/m | melanoma ubiquitous mutated 2 | melanoma |
| MUM-3/m | melanoma ubiquitous mutated 3 | melanoma |
| Myosin class I/m | | melanoma |
| neo-PAP/m | | melanoma |
| NFYC/m | | lung squamous cell carcinoma |
| N-Ras/m | | melanoma |
| OGT/m | | colorectal carcinoma |
| OS-9/m | | melanoma |
| p53/m | | |
| Pml/RARa | promyelocytic leukemia/retinoic acid receptor alpha | APL, PML |
| PRDX5/m | | melanoma |
| PTPRX/m | receptor-type protein-tyrosine phosphatase kappa | melanoma |
| RBAF600/m | | melanoma |
| SIRT2/m | | melanoma |
| SYT-SSX-1 | synaptotagmin I/synovial sarcoma X fusion protein | sarcoma |
| SYT-SSX-2 | synaptotagmin I/synovial sarcoma X fusion protein | sarcoma |
| TEL-AML1 | translocation Ets-family leukemia/acute myeloid leukemia 1 fusion protein | AML |
| TGFbRII | TGFbeta receptor II | colorectal carcinoma |
| TPI/m | triosephosphate isomerase | melanoma |

In a preferred embodiment according to the invention, antibodies encoded by the inventive RNA are directed against the following (protein) antigens (whereby the RNA molecules may be used for the preparation of a medicament, e.g. a pharmaceutical composition or more preferably a (passive) vaccine in the meaning of the present inventino), are selected from the group consisting of 5T4, 707-AP, 9D7, AFP, AlbZIP HPG1, alpha-5-beta-1-integrin, alpha-5-beta-6-integrin, alpha-actinin-4/m, alpha-methylacyl-coenzyme A racemase, ART-4, ARTC1/m, B7H4, BAGE-1, BCL-2, bcr/abl, beta-catenin/m, BING-4, BRCA1/m, BRCA2/m, CA 15-3/CA 27-29, CA 19-9, CA72-4, CAl25, calreticulin, CAMEL, CASP-8/m, cathepsin B, cathepsin L, CD19, CD20, CD22, CD25, CDE30, CD33, CD4, CD52, CD55, CD56, CD80, CDC27/m, CDK4/m, CDKN2A/m, CEA, CLCA2, CML28, CML66, COA-1/m, coactosin-like protein, collage XXIII, COX-2, CT-9/BRD6, Cten, cyclin B1, cyclin D1, cyp-B, CYPB1, DAM-10, DAM-6, DEK-CAN, EFTUD2/m, EGFR, ELF2/m, EMMPRIN, EpCam, EphA2, EphA3, ErbB3, ETV6-AML1, EZH2, FGF-5, FN, Frau-1, G250, GAGE-1, GAGE-2, GAGE-3, GAGE-4, GAGE-5, GAGE-6, GAGE7b, GAGE-8, GDEP, GnT-V, gp100, GPC3, GPNMB/m, HAGE, HAST-2, hepsin, Her2/neu, HERV-K-MEL, HLAA*0201-R17I, HLA-A11/m, HLA- A2/m, FINE, homeobox NKX3.1, HOM-TES-14/SCP-1, HOM-TES-85, HPV-E6, HPV-E7, HSP70-2M, HST-2, hTERT, iCE, IGF-1R, IL-13Ra2, IL-2R, IL-5, immature laminin receptor, kallikrein-2, kallikrein-4, Ki67, KIAA0205, KIAA0205/m, KK-LC-1, K-Ras/m, LAGEAl, LDLR-FUT, MAGE-A1, MAGE-A2, MAGE-A3, MAGE-A4, MAGE-A6, MAGE-A9, MAGE-A10, MAGE-A12, MAGE-B1, MAGE-B2, MAGE-B3, MAGE-B4, MAGE-B5, MAGE-B6, MAGE-B10, MAGE-B16, MAGE-B17, MAGE-C1, MAGE-C2, MAGE-C3, MAGE-D1, MAGE-D2, MAGE-D4, MAGE-E1, MAGE-E2, MAGE-F1, MAGE-H1, MAGEL2, mammaglobin A, MART-1/melan-A, MART-2, MART-2/m, matrix protein 22, MC$^1$R, M-CSF, MEl/m, mesothelin, MG50/PXDN, MMP11, MN/CA DC-antigen, MRP-3, MUC-1, MUC-2, MUM-1/m, MUM-2/m, MUM-3/m, myosin class Um, NA88-A, N-acetylglucosaminyltransferase-V, Neo-PAP, Neo-PAP/m, NFYC/m, NGEP, NMP22, NPM/ALK, NRas/m, NSE, NY-ESO-1, NY-ESO-B, OA1, OFA-iLRP, OGT, OGT/m, OS-9, OS-9/m, osteocalcin, osteopontin, p15, p190 minor bcr-abl, p53, p53/m, PAGE-4, PAI-1, PAI-2, PART-1, PATE, PDEF, Pim-1-Kinase, Pin-1, Pml/PARalpha, POTE, PRAME, PRDX5/m, prostein, proteinase-3, PSA, PSCA, PSGR, PSM, PSMA, PTPRK/m, RAGE-1, RBAF600/m, RHAMM/CD168, RU1, RU2, S-100, SAGE, SART-1, SART-2, SART-3, SCC, SIRT2/m, Sp17, SSX-1, SSX-2/HOM-MEL-40, SSX-4, STAMP-1, STEAP, survivin, survivin-2B, SYT-SSX-1, SYT-SSX-2, TA-90, TAG-72, TARP, TEL-AML1, TGFbeta, TGFbetaRII, TGM-4, TPI/m, TRAG-3, TRG, TRP-1, TRP-2/6b, TRP/INT2, TRP-p8, tyrosinase, UPA, VEGF, VEGFR-2/FLK-1, and WT1.

In a particularly preferred embodiment, the RNA codes for antibodies which are directed against protein antigens selected from the group consisting of MAGE-A1, MAGE-A6, melan-A, GP100, tyrosinase, survivin, CEA, Her-2/neu, WT1, PRAME, EGFR1 (epidermal growth factor receptor 1), mucin-1 and SEC61G, hTERT, 5T4, NY-Esol, and TRP-2, more preferably from sequences of group consisting of MAGE-A1 [accession number M77481], MAGE-A6 [accession number NM_005363], melan-A [accession number NM_005511], GP100 [accession number M77348], tyrosinase [accession number NM 000372], survivin [accession number AF077350], CEA [accession number NM 004363], Her-2/neu [accession number M11730], WT1 [accession number NM_000378], PRAME [accession number NM 006115], EGFR1 (epidermal growth factor receptor 1) [accession number AF288738], mucin-1 [accession number NM_002456] and SEC61G [accession number NM_014302], hTERT [accession number NM 198253], 5T4 [accession number NM 006670], NY-Eso1 [accession number NM_001327], and TRP-2 [accession number NM_001922].

Antibodies (and therefore also the RNAs according to the invention on which these antibodies are based) which bind the antigens described here and, possibly, other antigens or nucleic acids can be identified e.g. by means of the method of phage display developed by George P. Smith. In this context, antibodies or antibody fragments are typically expressed on the surface of filamentous phages (Smith, G. P., 1985, "Filamentous fusion phage: novel expression vectors that display cloned antigens on the virion surface", Science 228; 1315-1317). For this there are conventionally 3 to 5 copies of the surface protein gpIII on the proximal end of the phage, with the aid of which the phage infects bacteria cells via the F pilus thereof. In phage display, for example, the DNA for an antibody fragment which codes the antigen-binding variable domain is then cloned in-frame before the gpIII gene. In protein biosynthesis, a fusion protein is formed therefrom, which is expressed on the virus surface without the phage losing its infectiousness. With the aid of the phage display technique, it is possible to generate large antibody libraries, each phage expressing a different antibody fragment on the surface. To this extent, the underlying RNA is therefore also available. A particular antibody fragment can be isolated from such a library by a method called "phage panning". For this, the corresponding antigen is bound to a matrix and incubated with the phage suspension. The phages which present an appropriate antibody fragment interact with the fixed antigen, while the other phages are removed by a washing step. The phages isolated are multiplied, for example, in *E. coli*. The DNA is isolated accordingly and the gene sequence is determined. Expression constructs which contain the cDNA coding for the entire antibody or antibody fragments can then be developed with the aid of genetic engineering methods. An RNA (mRNA) which codes for the antibody can be generated from this cDNA by means of in vitro transcription (see below). Nucleic acids or, respectively, mRNA coding for monoclonal antibodies which are entirely of human origin are obtained in this manner.

In the context of the present invention, RNA according to the invention which codes for antibodies as described above is also suitable for coding so-called intrabodies or for rendering possible an expression of intrabodies. Intrabodies in the context of the present invention can include any of the antibodies or anti-body fragments described here. Intrabodies are intracellularly expressed antibodies, i.e. antibodies which are coded by nucleic acids localized in the cell and are expressed there. For this, an RNA according to the invention which encodes the antibodies or antibody fragments as described above is introduced into cells beforehand, for example with the aid of transfection methods according to the invention or other suitable transfection methods (see below) and, where appropriate, thereafter transplanted into an organism or being or introduced directly as nucleic acids into an organism or being. In this context (irrespective of whether an intrabody or a secreted antibody shall be introduce into the cell), the RNA according to the invention (or a corresponding nucleic acid) can be introduced in the naked form or as a complex with suitable carriers (e.g. liposomes) into the organism or the being or can have such modifications (of the RNA) which, where appropriate together with one of the transfection methods mentioned, lead to a better cell uptake, e.g. any of the RNA modifications mentioned here, such as, for example, lipid modifications of the RNA according to the invention. An organism or a being in connection with the present invention typically means mammals, i.e. animals, including cattle, pig, dog, cat, donkey, monkey, rodents, e.g. mouse, hamster, rabbit etc., and humans. Intrabodies can be localized and expressed at certain sites in the cell. For example, intrabodies can be expressed in the cytoplasm, the formation of disulfide bridges usually being decreased under the reducing conditions of the cytoplasm. It has been possible to demonstrate, however, that cytoplasmic intrabodies, and in particular scFv fragments, can be functional. Cytoplasmic expression by the RNA according to the invention opens up the possibility of also inhibiting cytoplasmic proteins. This is not possible with treatment with monoclonal antibodies from the prior art, since these antibodies can reach only secreted and membrane-located (extracellular) proteins due to their secretion from the cell after intracellular expression (which represents the major difference between antibodies and intrabodies). By expression of a signal peptide, intrabodies can be transported into the endoplasmic reticulum (ER) and then secreted as with regular antibodies. In this case, typically only secreted or membrane-located proteins are a target for these antibodies. By additional coding of a C-terminal ER retention signal (for example KDEL (SEQ ID NO: 18)) by the RNA according to the invention, the intrabody can remain in the ER (where it may bind to specific antigen located in the ER) and prevent secretion of its antigen and/or transport of its antigen or its target molecule to the plasma membrane. Depending on the requirement, intrabodies can include full length antibodies or antibody fragments as described above. Intrabodies in the context of the present invention preferably initially include full length antibodies, which are retained in the cell and not secreted from the cell (by whatever technique, e.g. retention signal sequences etc.). However, if e.g. intracellular expression of full length antibodies is technically not possible or not appropriate, antibody fragments as described above can also be employed as intrabodies.

Antibodies which are coded by the RNA according to the invention furthermore also include those anti-bodies or antibody fragments which have a sequence identity to one of the antibodies or antibody fragments described here of at least 70%, 80% or 85%, preferably at least 90%, more preferably at least 95% and most preferably at least 99% over the entire length of the coding nucleic acid or amino acid sequence of an antibody or antibody fragment as described here. Preferably, such antibodies or antibody fragments have the same biological function as or, respectively, the specific activity of the corresponding full length antibody, e.g. the specific binding of particular antigens or nucleic acids. Accordingly, it is preferred, if the hypervariable region(s) are conserved or are modified by merely conservative mutations.

The biological function of antibodies described here which are coded by the RNA according to the invention includes e.g. neutralization of antigens, complement activation or opsonization. In the case of neutralization of antigens, the antibody can bind to an antigen and thereby neutralize this. The antibody is conventionally blocked by the binding of the antigen, and can therefore display its action only against one antigen, or two antigens in the case of bispecific antibodies. scFv antibody fragments are suitable above all for this (neutralization) function of an antibody, since they do not include the functions of the constant domains of an antibody. In the case of complement activation, the complex system of complement proteins which are dependent upon the Fc part of the antibody can be activated via binding of antibodies. End products of the complement cascade typically lead to lysis of cells and to the creation of a phlogistic (inflammatory) milieu. In the case of opsonization, pathogens or foreign particles are rendered accessible to phagocytes by binding by an antibody via the constant domains of the antibody. Alternatively, the opsonized cells, which are recognized as foreign, can be lysed via an antibody-dependent, cell-mediated cytotoxicity (ADCC). In this context, NK cells in particular can perform lytic functions in this manner via activation of their Fc receptors.

In connection with the present invention, the term "identity" means that the sequences are compared with one another as follows. In order to determine the percentage identity of two nucleic acid sequences, the sequences can first be aligned with respect to one another in order subsequently to make a comparison of these sequences possible. For this e.g. gaps can be inserted into the sequence of the first nucleic acid sequence and the nucleotides can be compared with the corresponding position of the second nucleic acid sequence. If a position in the first nucleic acid sequence is occupied by the same nucleotide as is the case at a position in the second sequence, the two sequences are identical at this position. The percentage identity between two sequences is a function of the number of identical positions divided by the number of all the positions compared in the sequences investigated. If e.g. a specific sequence identity is assumed for a particular nucleic acid (e.g. a nucleic acid which codes for a protein, as described above) in comparison with a reference nucleic acid (e.g. a nucleic acid from the prior art) of defined length, this percentage identity is stated relatively with reference to this reference nucleic acid. Starting therefore, for example, from a nucleic acid which has a sequence identity of 50% to a reference nucleic acid 100 nucleotides long, this nucleic acid can be a nucleic acid 50 nucleotides long which is completely identical to a 50 nucleotides long section of the reference nucleic acid. Indeed, it can also be a nucleic acid 100 nucleotides long which has 50% identity, i.e. in this case 50% identical nucleic acids, with the reference nucleic acid over the entire length thereof. Alternatively, this nucleic acid can be a nucleic acid 200 nucleotides long which is completely identical in a 100 nucleotides long section of the nucleic acid to the reference nucleic acid 100 nucleotides long. Other nucleic acids of course equally meet these criteria. The identity statements described for nucleic acids apply equally to the antibodies and antibody fragments coded by the RNA according to the invention. The same holds for the determination of the sequence identity between two (poly)peptides, based on the comparison/alignment of the respective amino acid sequences.

The percentage identity of two sequences can be determined with the aid of a mathematical algorithm. A preferred, but not limiting, example of a mathematical algorithm which can be used for comparison of two sequences is the algorithm of Karlin et al. (1993), PNAS USA, 90:5873-5877. Such an algorithm is integrated in the NBLAST program, with which sequences which have a desired identity to the sequences of the present invention can be identified. In order to obtain a gapped alignment, as described here, the "Gapped BLAST" program can be used, as is described in Altschul et al. (1997), Nucleic Acids Res, 25:3389-3402. If BLAST and Gapped BLAST programs are used, the preset parameters of the particular program (e.g. NBLAST) can be used. The sequences can be aligned further using version 9 of GAP (global alignment program) of the "Genetic Computing Group" using the preset (BLOSUM62) matrix (values −4 to +11) with a gap open penalty of −12 (for the first zero of a gap) and a gap extension penalty of −4 (for each additional successive zero in the gap). After the alignment, the percentage identity is calculated by expressing the number of agreements as a percentage content of the nucleic acids in the sequence claimed. The methods described for determination of the percentage identity of two nucleic acid sequences can also be used correspondingly, if necessary, on the coded amino acid sequences, e.g. the anti-bodies described here.

According to a preferred embodiment, the antibody-coding RNA according to the invention contains acoding regions which codes for one of the anribodies listed in Table 3. The antibody encoding RNA may be used to treat (or, may be used to provide a pharmaceutical composition to treat) one of the diseases, disorders, pathologies listed in the right-hand column of Table 3.

TABLE 3

| Name | Target | Clinical application |
|---|---|---|
| Oregovomab (OvaRex) | CA125 (MUC-16) | Ovarian Cancer, Fallopian Tube Cancer, Peritoneal Cavity Cancer |
| Cantuzumab | CanAg (MUC-1) | Colon Cancer, Gastric Cancer, Pancreatic Cancer, NSCLC |
| HuC242-DM4 | CanAg (MUC-1) | Colon Cancer, Gastric Cancer, Pancreatic Cancer |
| PAM4 (IMMU-107) | CanAg (MUC-1) | Pancreatic Cancer |
| HuC242-DM4 | CanAg (MUC-1) | Colorectal Cancer; Pancreatic Cancer |
| HuHMFG1 | CanAg (MUC-1) | Breast Cancer |
| WX-G250 (Rencarex) | Carbonische Anhydrase IX (G250) | Renal Cell Carcinoma |
| MT103 | CD19 | Non-Hodgkin-Lymphoma |
| Ibritumomab (Zevalin) | CD20 | Non-Hodgkin-Lymphoma, Lymphoma |
| Rituximab (Rituxan, MabThera) | CD20 | Non-Hodgkin-Lymphoma, Lymphoma, Chronic Lymphocytic Leukemia |
| Tositumomab (Bexxar) | CD20 | Non-Hodgkin-Lymphoma, Lymphoma, Myeloma |
| Ofatumamab (HuMax-CD20) | CD20 | Lymphoma, B-Cell Chronic Lymphocytic Leukemia |
| Epratuzumab (Lympho-Cide) | CD22 | Non-Hodgkin-Lymphoma, Leukemia |
| MDX-060 | CD30 | Hodgkin-Lymphoma, Lymphoma |
| SGN-30 | CD30 | Hodgkin-Lymphoma, Lymphoma |
| Gemtuzumab (Mylotarg) | CD33 | Leukemia |
| Zanolimumab (HuMax-CD4) | CD4 | T-Cell-Lymphoma |
| SGN-40 | CD40 | Non-Hodgkin-Lymphoma, Myeloma, Leukemia, Chronic Lymphocytic Leukemia |
| Alemtuzumab (MabCampath) | CD52 | T-Cell-Lymphoma, Leukemia |
| HuN901-DM1 | CD56 | Myeloma |
| Galiximab | CD80 | Non-Hodgkin-Lymphoma |
| Labetuzumab | CEA | Colon Cancer, Pancreatic Cancer, Ovarian Cancer |
| Ipilimumab (MDX-010) | CTLA4 | Sarcoma, Melanoma, Lung cancer, Ovarian Cancer leucemia, Lymphoma, Brain and Central Nervous System Tumors, Testicular Cancer, Prostate Cancer, Pancreatic Cancer, Breast Cancer |
| Cetuximab (Erbitux) | EGFR | Colon Cancer, Head and Neck Cancer, Pancreatic Cancer, Non-Small Cell Lung Cancer, Cervical Cancer, Endometrial Cancer, Breast Cancer, Myeloma, Lung Cancer, Gastric Cancer, Esophageal Cancer, Pancreatic Cancer, Oropharyngeal Neoplasms, Hepatocellular Carcinoma, Squamous Cell Carcinoma, Sarcoma, Larynx Cancer; Hypopharynx Cancer |
| Panitumumab (Vectibix) | EGFR | Colon Cancer, Lung Cancer, Breast Cancer; Bladder Cancer; Ovarian Cancer |
| Nimotuzumab (TheraCim) | EGFR | Solid Tumors, Lung Cancer |
| Matuzumab | EGFR | Lung Cancer, Cervical Cancer, Esophageal Cancer |
| Zalutumumab | EGFR | Head and Neck Cancer, Squamous Cell Cancer |
| Pertuzumab (Omnitarg) | EGFR und HER2/neu | Breast Cancer, Ovarian Cancer, Lung Cancer, Prostate Cancer |
| Catumaxomab (Removab) | EpCam | Ovarian Cancer, Fallopian Tube Neoplasms, Peritoneal Neoplasms |
| MORab-003 | GP-3 | Ovarian Cancer, Fallopian Tube Cancer, Peritoneal Cancer |
| MORab-009 | GP-9 | Pancreatic Cancer, Mesothelioma, Ovarian Cancer, Non-Small Cell Lung Cancer, Fallopian Tube Cancer, Peritoneal Cavity Cancer |
| Ertumaxomab | HER2/neu | Breast Cancer |
| Trastuzumab (Herceptin) | HER2/neu | Breast Cancer, Endometrial Cancer, Solid Tumors |
| AMG 102 | HGF | Advanced Renal Cell Carcinoma |
| Apolizumab (Remitogen) | HLA-DR-Antigen | Solid Tumors, Leukemia, Non-Hodgkin-Lymphoma, Lymphoma |
| CNTO 95 | Integrin-Rezeptor | Melanoma |
| ID09C3 | MHCII | Non-Hodgkin-Lymphoma |
| Denosumab (AMG-102) | RANKL | Myeloma, Giant Cell Tumor of Bone, Breast Cancer, Prostate Cancer |
| GC1008 | TGFbeta | Advanced Renal Cell Carcinoma; Malignant Melanoma |
| Mapatumumab | TRAIL-R1 | Colon Cancer, Myeloma |
| Bevacizumab (Avastin) | VEGF | Colon Cancer, Breast Cancer, Brain and Central Nervous System Tumors, Lung Cancer, Hepatocellular Carcinoma, Kidney Cancer, Breast Cancer, Pancreatic Cancer, Bladder Cancer, Sarcoma, Melanoma, Esophageal Cancer; Stomach Cancer, Metastatic Renal Cell Carcinoma; Kidney Cancer, Glioblastoma, Liver Cancer |
| MEDI 522 | VLA3 (alpha5beta3-Integrin) | Solid Tumors, Leukemia, Lymphoma, Small Intestine Cancer, Melanoma |
| Volociximab | VLA5 (alpha5beta1-Integrin) | Renal Cell Carcinoma, Pancreatic Cancer, Melanoma |

TABLE 3-continued

| Name | Target | Application |
|---|---|---|
| Hematology: | | |
| Eculizumab (Alexion) | C5 Komplementfaktor | Paroxysmale nächtliche Hämoglobinurie (PNH) |
| Mepolizumab | Interleukin-5 | Hypereosinophilie-Syndrom |
| Dentology: | | |
| CaroRx (CaroRx) | *Streptococcus mutans* | Zahnkaries |
| Autoimmune Diseases und allergic Diseases: | | |
| Efalizumab (Raptiva) | CD11a | Psoriasis (Schuppenflechte) |
| Epratuzumab (LymphoCide) | CD22 | Autoimmune Diseases, Non-Hodgkin-Lymphom |
| Lumiliximab | CD23 | Allergies |
| Daclizumab | CD25 | Schubförmige Multiple Sclerosis |
| Natalizumab (Tysabri) | CD49d | Multiple Sclerosis |
| Omalizumab (Xolair) | IgE (Fc-Teil) | Schweres Asthma bronchiale |
| Mepolizumab | Interleukin-5 | Asthma, Hypereosinophilic Syndrome, Eosinophilic Gastroenteritis, Churg-Strauss Syndrome, Eosinophilic Esophagitis |
| Tocilizumab (Actemra) | Interleukin-6 | Rheumatoid Arthritis |
| Adalimumab (Humira) | TNFα | Rheumatoid Arthritis, Psoriasis-Arthritis, Morbus Bechterew |
| Infliximab (Remicade) | TNFα | Morbus Crohn, Rheumatoide Arthritis, Morbus Bechterew, Psoriasis-Arthritis, Colitis ulcerosa, Psoriasis (Schuppenflechte) |
| Golimumab (CNTO 148) | TNFα | Rheumatoid Arthritis |
| Mapatumumab | TRAIL-R1 | Myeloma |
| Rituximab (Rituxan, MabThera) | CD20 | Urticaria, Rheumatoid Arthritis, Ulcerative Colitis, Chronic Focal Encephalitis |
| Epratuzumab (LymphoCide) | CD22 | Autoimmune diseases, Systemic Lupus Erythematosus |
| Neurodegenerative Diseases: | | |
| R1450 | Amyloid-beta | Alzheimer |
| Ophthalmology: | | |
| Ranibizumab (Lucentis) | VEGF-A | Feuchte Macular Degeneration |
| Bevacizumab (Avastin) | VEGF | Macular Degeneration |
| Infectious Diseases: | | |
| Palivizumab (Synagis) | Component of RSV (Respiratory Syncytial Virus) | Prevention of RSV-Pneumonia bei Frühgeborenen |
| Cardiovascular Diseases: | | |
| Abciximab (ReoPro) | GPIIb/IIa | Verhinderung eines Gefäßverschlusses nach PTCA |
| Other Diseases: | | |
| Denosumab (AMG-102) | RANKL | Osteoporosis |
| GC1008 | TGFbeta | Pulmonary Fibrosis |
| Bevacizumab (Avastin) | VEGF | Proliferative Diabetic Retinopathy |

According to a preferred embodiment, the antibody-coding RNA according to the invention contains or has a sequence which codes for the heavy chains according to SEQ ID NO: 2 and the light chains according to SEQ ID NO: 4. According to an even more preferred embodiment, the antibody-coding RNA according to the invention contains or has a coding sequence according to SEQ ID NO: 5 or SEQ ID NO: 51, respectively.

According to another preferred embodiment, the antibody-coding RNA according to the invention contains or has a sequence which codes for the heavy chains according to SEQ ID NO: 7 and the light chains according to SEQ ID NO: 9. According to an even more preferred embodiment, the antibody-coding RNA according to the invention contains or has a coding sequence according to SEQ ID NO: 10 or SEQ ID NO: 52, respectively.

According to a further preferred embodiment, the antibody-coding RNA according to the invention contains or has a sequence which codes for the heavy chains according to SEQ ID NO: 12 and the light chains according to SEQ ID NO: 14. According to an even more preferred embodiment, the antibody-coding RNA according to the invention contains or has a coding sequence according to SEQ ID NO: 15 or SEQ ID NO: 53, respectively.

Antibodies which are coded by the RNA according to the invention can furthermore also encode such antibodies which have a sequence identity to one of the coding sequences of the antibodies described here, e.g. as described by Table 3 or by SEQ ID NO: 5 (51), 10 (52) or 15 (53), of at least 70%, 80% or 85%, preferably at least 90%, more preferably at least 95% and most preferably at least 99% over the entire length of the nucleic acid sequence or amino acid sequence of an antibody as described here, e.g. as described by Table 3 or by SEQ ID NO: 5 (51), 10 (52) or 15 (53).

Such antibodies which are coded by the RNA according to the invention likewise include antibodies according to SEQ ID NO: 5 (51), 10 (52) or 15 (53) or according to Table 3 which contain or have, in one of the heavy chains described here according to SEQ ID NO: 2, 7 or 12 and/or in one of the light chains described here according to SEQ ID NO: 4, 9 or 14, a nucleic acid or amino acid sequence identity of at least 70%, 80% or 85%, preferably at least 90%, more preferably at least 95% and most preferably at least 99% over the entire length of the coding sequence for the particular light and/or heavy chain, with an otherwise unchanged coding antibody sequence of SEQ ID NO: 5 (51), 10 (52) or 15 (53) or e.g. antibodies of Table 3.

Overall, a novel route for carrying out antibody therapies on the basis of RNA, in particular mRNA, is thus provided with the aid of the present invention. In such a manner, clinically tested antibodies, for example angiogenesis inhibitors based on antibodies, for example bevacizumab (monoclonal immunoglobulin $G_1$ antibody which binds to the vascular growth factor VEGF (vascular endothelial growth factor); or trastuzumab (Herceptin), an indirect inhibitor which inhibits the action of tumour proteins on receptors, or for example rituximab or cetuximab (directed against the epidermal growth factor receptor (EGFR)), based on RNA, can be provided, so that the inventive RNA contains at least one coding region which codes for at least one of these antibodies.

In a preferred embodiment, the antibody-coding RNA according to the invention typically additionally has at least one of the following modifications, which are preferably suitable for increasing the stability of the coding RNA, improving the expression of the antibody thereby coded, increasing the cell permeability, rendering possible localization of the antibody on or in certain cell compartments etc. Each of these modifications of the RNA according to the invention described here (modified RNA) which are mentioned in the following can be combined with one another in a suitable manner, such modifications which do not interfere with one another or adversely influence the stability or cell permeability of the antibody-coding, modified RNA according to the invention or the expression of the antibody thereby coded preferably being combined with one another. For the entire present invention, the nomenclature "modified" is equated with the content of "optionally modified".

Modifications of the RNA according to the invention described here (modified RNA) can include, for example, modifications of the nucleotides of the RNA. An RNA (modified RNA) according to the invention can thus include, for example, backbone modifications, sugar modifications or base modifications. In this context, the antibody-coding RNA according to the invention typically first contains nucleotides which can be chosen from all naturally occurring nucleotides and analogues thereof (modified nucleotides), such as e.g. ribonucleotides and/or deoxyribonucleotides. Nucleotides in the context of the present invention therefore include, without being limited thereto, for example purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, β-D-mannosyl-queosine, wybutoxosine, and phosphoramidates, phosphorothioates, peptide nucleotides, methylphosphonates, 7-deazaguanosine, 5-methylcytosine and inosine. The preparation of such analogues is known to a person skilled in the art e.g. from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosure of which is included here in its full scope by reference.

In particular, an antibody-coding RNA according to the invention can contain RNA backbone modifications. In connection with the present invention, a backbone modification is a modification in which the phosphates of the backbone of the nucleotides contained in the RNA are modified chemically. In this context, such backbone modifications typically include, without being limited thereto, modifications from the group consisting of methylphosphonates, methylphosphoramidates, phosphoramidates, phosphorothioates (e.g. cytidine 5'-O-(1-thiophosphate)), boranophosphates, positively charged guanidinium groups etc., which means by replacing the phosphodiester linkage by other anionic, cationic or neutral groups.

An antibody-coding RNA according to the invention can likewise also contain sugar modifications. A sugar modification in connection with the present invention is a chemical modification of the sugar of the nucleotides it contains and typically includes, without being limited thereto, sugar modifications chosen from the group consisting of 2'-deoxy-2'-fluoro-oligoribonucleotide (2'-fluoro-2'-deoxycytidine 5'-triphosphate, 2'-fluoro-2'-deoxyuridine 5'-triphosphate), 2'-deoxy-2'-deamine-oligoribonucleotide (2'-amino-2'-deoxycytidine 5'-triphosphate, 2'-amino-2'-deoxyuridine 5'-triphosphate), 2'-O-alkyloligoribonucleotide, 2'-deoxy-2'-C-alkyloligoribonucleotide (2'-O-methylcytidine 5'-triphosphate, 2'-methyluridine 5'-triphosphate), 2'-C-alkyloligoribonucleotide, and isomers thereof (2'-aracytidine 5'-triphosphate, 2'-arauridine 5'-triphosphate), or azidotriphosphates (2'-azido-2'-deoxycytidine 5'-triphosphate, 2'-azido-2'-deoxyuridine 5'-triphosphate).

Preferably, however, the modified RNA sequence according to the invention contains no sugar modifications or backbone modifications if e.g. an in vitro transcription is necessary. The reason for this preferred exclusion lies in the problem that certain backbone modifications and sugar modifications of RNA sequences on the one hand can prevent or at least greatly reduce in vitro transcription thereof. Thus, an in vitro transcription of eGFP carried out by way of example functions, for example, only with the sugar modifications 2'-amino-2'-deoxyuridine 5'-phosphate, 2'-fluoro-2'-deoxyuridine 5'-phosphate and 2'-azido-2'-deoxyuridine 5'-phosphate. In addition, the translation of the protein, i.e. the protein expression, in vitro or in vivo typically can be reduced considerably by backbone modifications and, independently thereof, by sugar modifications of RNA sequences. It was possible to demonstrate this, for example, for eGFP in connection with the backbone modifications and sugar modifications selected above.

An antibody-coding RNA according to the invention can likewise also contain modifications of the bases of the nucleotides it contains (base modifications). Thus, for example, the antibody-coding RNA according to the invention can be modified such that only one or several of the nucleotides of the modified RNA are exchanged for nucleotides having base modifications, which are preferably suitable for increasing the expression of the antibody coded by the RNA significantly compared with the non-modified, i.e. native RNA sequence. In this case, significant means an increase in the expression of the antibody on the basis of the modified RNA sequence compared with the native RNA sequence by at least 20%, preferably at least 30%, 40%, 50% or 60%, even more preferably by at least 70%, 80%, 90% or even 100% and most preferably by at least 150%, 200% or even 300%. In connection with the present invention, a modified nucleotide which contains a base modification is called a base-modified nucleotide and, without being limited thereto, is preferably chosen from the group consisting of 2-amino-6-chloropurine riboside 5'-triphosphate, 2-aminoadenosine 5'-triphosphate, 2-thiocytidine 5'-triphosphate, 2-thiouridine 5'-triphosphate, 4-thiouridine 5'-triphosphate, 5-aminoallylcytidine 5'-triphosphate, 5-aminoallyluridine 5'-triphosphate, 5-bromocytidine 5'-triphosphate, 5-bromouridine 5'-triphosphate, 5-iodocytidine 5'-triphosphate, 5-iodouridine 5'-triphosphate, 5-methylcytidine 5'-triphosphate, 5-methyluridine 5'-triphosphate, 6-azacytidine 5'-triphosphate, 6-azauridine 5'-triphosphate, 6-chloropurine riboside 5'-triphosphate, 7-deazaadenosine 5'-triphosphate, 7-deazaguanosine 5'-triphosphate, 8-azaadenosine 5'-triphosphate, 8-azidoadenosine 5'-triphosphate, benzimidazole riboside 5'-triphosphate, N1-methyladenosine 5'-triphosphate, N1-methylguanosine 5'-triphosphate, N6-methyladenosine 5'-triphosphate, O6-methylguanosine 5'-triphosphate, pseudouridine 5'-triphosphate, puromycin 5'-triphosphate or xanthosine 5'-triphosphate. Nucleotides for base modifications are particularly preferably chosen from the group of base-modified nucleotides consisting of 5-methylcytidine 5'-triphosphate and pseudouridine 5'-triphosphate.

Without being restricted thereto, in this connections the inventors attribute an increase in the expression of the antibody coded by the (base)-modified RNA according to the invention to, inter alia, the improvement in the stabilizing of secondary structures and, where appropriate, to the "more rigid" structure formed in the RNA and the increased base stacking. Thus, for example, it is known of pseudouridine 5'-triphosphate that this occurs naturally in structural RNAs (tRNA, rRNA and snRNA) in eukaryotes as well as in prokaryotes. In this connection, it is assumed that pseudouridine is necessary in rRNA for stabilizing secondary structures. In the course of evolution, the content of pseudouridine in RNA has increased, and it has been possible to demonstrate, surprisingly, that the translation depends on the presence of pseudouridine in the tRNA and rRNA, the interaction between tRNA and mRNA presumably being intensified in this context. The conversion of undine into pseudouridine takes place posttranscriptionally by pseudouridine synthase. A posttranscriptional modification of RNA likewise takes place in the case of 5-methylcytidine 5'-triphosphate, and is catalysed by methyltransferases. A further increase in the content of pseudouridine and the base modification of other nucleotides is assumed to lead to similar effects, which, in contrast to the naturally occurring increased contents of pseudouridine in the sequence, can be carried out in a targeted manner and with a considerably wider variability. For 5-methylcytidine 5'-triphosphate and the further base modifications mentioned here, a similar mechanism to that for pseudouridine 5'-triphosphate is therefore assumed, i.e. an improved stabilizing of secondary structures, and on the basis of this an improved translation efficiency. In addition to this structurally based increase in expression, however, a positive effect on the translation is presumed, independently of the stabilizing of secondary structures and a "more rigid" structure of the RNA. Further causes of the increase in expression are also to be found, possibly, in the lower degradation rate of the RNA sequences by RNAses in vitro or in vivo.

The modifications of the antibody-coding RNA according to the invention which are described above can be introduced into the RNA with the aid of methods known to a person skilled in the art. Possible methods for this are, for example, synthesis methods using (automatic or semi-automatic) oligonucleotide synthesis apparatuses, biochemical methods, such as e.g. in vitro transcription methods, etc. Preferably, in this connection, for (shorter) sequences which in general do not exceed a length of 50-100 nucleotides, synthesis methods using (automatic or semi-automatic) oligonucleotide synthesis apparatuses and also in vitro transcription methods can be employed. For (longer) sequences, e.g. sequences which have a length of more than 50 to 100 nucleotides, biochemical methods are preferred, such as, for example, in vitro transcription methods, preferably an in vitro transcription method as described here, optionally using the modified RNA according to the invention.

Modifications with nucleotides as described here in an antibody-coding RNA according to the invention can occur on at least one (modifiable) nucleotide of the RNA sequence according to the invention, preferably on at least 2, 3, 4, 5, 6, 7, 8, 9 or 10 (modifiable) nucleotides, more preferably on at least 10-20 (modifiable) nucleotides, even more preferably on at least 10-100 (modifiable) nucleotides and most preferably on at least 10-200, 10 to 1,000 or 10 to 10,000 or more (modifiable), e.g. all, nucleotides. Worded alternatively, modifications in an antibody-coding RNA according to the invention can occur on at least one (modifiable) nucleotide of the RNA sequence according to the invention, preferably on at least 10% of all the (modifiable) nucleotides, more preferably on at least 25% of all the (modifiable) nucleotides, even more preferably on at least 50% of all the (modifiable) nucleotides, even more preferably on at least 75% of all the (modifiable) nucleotides and most preferably on 100% of the (modifiable) nucleotides contained in the RNA sequence according to the invention. In this connection, a "modifiable nucleotide" is any (preferably naturally occurring (native) and therefore non-modified) nucleotide which is to be exchanged for a nucleotide modified as described here. In this context, all the nucleotides of the RNA sequence can be modified, or only certain selected nucleotides of the RNA sequence. If all the nucleotides of the RNA sequence are to be modified, 100% of the "modifiable nucleotides" of the RNA sequence are all the nucleotides of the RNA sequence used. On the other hand, if only certain selected nucleotides of the RNA sequence are to be modified, the selected nucleotides are, for example, adenosine, cytidine, guanosine or uridine. Thus, for example, an adenosine of the native sequence can be exchanged for a modified adenosine, a cytidine for a modified cytidine, a uridine for a modified uridine and a guanosine for a modified guanosine. In this case, 100% of the "modifiable nucleotides" of the RNA sequence are 100% of the adenosines, cytidines, guanosines and/or uridines in the RNA sequence used.

According to another very preferred embodiment of the present invention, the antibody-coding RNA according to the invention can contain, for example, a GC content which has been modified compared with the native, i.e. non-modified (precursor) RNA sequence. According to a first alternative of the antibody-coding RNA according to the invention, the G/C content for the coding region of the RNA according to the invention is greater than the G/C content for the coding region of the native RNA sequence, the coded amino acid sequence of the antibody or antibody fragment being unchanged compared with the wild-type, i.e. the antibody or antibody fragment amino acid sequence coded by the native RNA sequence. In this context, the composition and the sequence of the various nucleotides plays a major role. In particular, sequences having an increased G (guanine)/C (cytosine) content are more stable than sequences having an increased A (adenine)/U (uracil) content. According to the invention, the codons are therefore varied compared with the wild-type RNA, while retaining the translated amino acid sequence, such that they include an increased amount of G/C nucleotides. Since several codons code for one and the same amino acid (degeneration of the genetic code), the most favourable codons for the stability can be determined (alternative codon usage).

Depending on the amino acid to be coded by the antibody-coding RNA according to the invention, there are various possibilities for modification of the native sequence of the RNA according to the invention. In the case of amino acids which are coded by codons which contain exclusively G or C nucleotides, no modification of the codon is necessary. Thus, the codons for Pro (CCC or CCG), Arg (CGC or CGG), Ala (GCC or GCG) and Gly (GGC or GGG) require no modification, since no A or U is present.

In the following cases, the codons which contain A and/or U nucleotides are modified by substitution of other codons which encode the same amino acids but contain no A and/or U. Examples are:
  the codons for Pro can be modified from CCU or CCA to CCC or CCG;
  the codons for Arg can be modified from CGU or CGA or AGA or AGG to CGC or CGG;
  the codons for Ala can be modified from GCU or GCA to GCC or GCG;
  the codons for Gly can be modified from GGU or GGA to GGC or GGG.

In other cases, although A or U nucleotides cannot be eliminated from the codons, it is however possible to decrease the A and U content by using codons which contain fewer A and/or U nucleotides. For example:
  the codons for Phe can be modified from UUU to UUC;
  the codons for Leu can be modified from UUA, CUU or CUA to CUC or CUG;
  the codons for Ser can be modified from UCU or UCA or AGU to UCC, UCG or AGC;
  the codon for Tyr can be modified from UAU to UAC;
  the stop codon UAA can be modified to UAG or UGA;
  the codon for Cys can be modified from UGU to UGC;
  the codon for H is can be modified from CAU to CAC;
  the codon for Gln can be modified from CAA to CAG;
  the codons for Ile can be modified from AUU or AUA to AUC;
  the codons for Thr can be modified from ACU or ACA to ACC or ACG;
  the codon for Asn can be modified from AAU to AAC;
  the codon for Lys can be modified from AAA to AAG;
  the codons for Val can be modified from GUU or GUA to GUC or GUG;
  the codon for Asp can be modified from GAU to GAC;
  the codon for Glu can be modified from GAA to GAG.

In the case of the codons for Met (AUG) and Trp (UGG), on the other hand, there is no possibility of sequence modification.

The substitutions listed above can of course be used individually or also in all possible combinations to increase the G/C content of the antibody-coding RNA according to the invention compared with the native RNA sequence (and nucleic acid sequence, respectively). Thus, for example, all the codons for Thr occurring in the native RNA sequence can be modified to ACC (or ACG). Preferably, however, combinations of the above substitution possibilities are used, e.g.:
  substitution of all codons coding for Thr in the native RNA sequence by ACC (or ACG) and substitution of all codons originally coding for Ser by UCC (or UCG or AGC);
  substitution of all codons coding for Ile in the native RNA sequence by AUC and substitution of all codons originally coding for Lys by AAG and substitution of all codons originally coding for Tyr by UAC;
  substitution of all codons coding for Val in the native RNA sequence by GUC (or GUG) and substitution of all codons originally coding for Glu by GAG and substitution of all codons originally coding for Ala by GCC (or GCG) and substitution of all codons originally coding for Arg by CGC (or CGG);
  substitution of all codons coding for Val in the native RNA sequence by GUC (or GUG) and substitution of all codons originally coding for Glu by GAG and substitution of all codons originally coding for Ala by GCC (or GCG) and substitution of all codons originally coding for Gly by GGC (or GGG) and substitution of all codons originally coding for Asn by AAC;
  substitution of all codons coding for Val in the native RNA sequence by GUC (or GUG) and substitution of all codons originally coding for Phe by UUC and substitution of all codons originally coding for Cys by UGC and substitution of all codons originally coding for Leu by CUG (or CUC) and substitution of all codons originally coding for Gln by CAG and substitution of all codons originally coding for Pro by CCC (or CCG); etc.

Preferably, the G/C content of the coding region of the antibody-coding RNA according to the invention is increased compared with the G/C content of the coding region of the native RNA such that at least 5%, at least 10%, at least 15%, at least 20%, at least 25% or more preferably at least 30%, at least 35%, at least 40%, at least 45%, at least 50% or at least 55%, even more preferably at least 60%, at least 65%, at least 70% or at least 75% and most preferably at least 80%, at least 85%, at least 90%, at least 95% or at least 100% of the possible modifiable codons of the coding region of the native RNA (and nucleic acid, respectively) are modified.

In this connection, it is particularly preferable to increase to the maximum the G/C content of the antibody-coding RNA according to the invention, in particular in the coding region, compared with the native RNA sequence.

A second alternative of the antibody-coding RNA according to the invention with modifications is based on the knowledge that the translation efficiency of the RNA is also determined by a different frequency in the occurrence of tRNAs in cells. Thus, if so-called "rare" codons are present in an RNA sequence to an increased extent, the corresponding RNA is translated to a significantly poorer degree than in the case where codons which code for relatively "frequent" tRNAs are present.

According to this second alternative of the antibody-coding RNA according to the invention, the coding region of the RNA according to the invention is therefore modified compared with the coding region of the native RNA such that at least one codon of the native RNA which codes for a tRNA which is relatively rare in the cell is exchanged for a codon which codes for a tRNA which is relatively frequent in the cell and which carries the same amino acid as the relatively rare tRNA.

By this modification, the sequence of the antibody-coding RNA according to the invention is modified such that codons for which frequently occurring tRNAs are available are inserted. Which tRNAs occur relatively frequently in the cell and which, in contrast, are relatively rare is known to a person skilled in the art; cf. e.g. Akashi, Curr. Opin. Genet. Dev. 2001, 11(6): 660-666.

According to the invention, by this modification all codons of the sequence of the antibody-coding RNA according to the invention which code for a tRNA which is relatively rare in the cell can be exchanged for a codon which codes for a tRNA which is relatively frequent in the cell and which carries the same amino acid as the relatively rare tRNA.

It is particularly preferable to link the increased, in particular maximum, sequential G/C content in the antibody-coding RNA according to the invention with the "frequent" codons without modifying the amino acid sequence coded by the RNA according to the invention. This preferred embodiment provides a particularly efficiently translated and stabilized RNA sequence according to the invention which encodes an antibody (for example for a pharmaceutical composition according to the invention).

In the sequences of eukaryotic RNAs, there are typically destabilizing sequence elements (DSE) to which signal proteins bind and regulate the enzymatic degradation of the RNA in vivo. For further stabilization of the antibody-coding RNA according to the invention, one or more modifications compared with the corresponding region of the native RNA are therefore optionally carried out in the region coding for the protein, so that no destabilizing sequence elements are present. According to the invention, it is of course also preferable, where appropriate, to eliminate from the RNA DSEs present in the untranslated regions (3' and/or 5' UTR).

Such destabilizing sequences are, for example, AU-rich sequences ("AURES"), which occur in 3' UTR sections of numerous unstable RNAs (Caput et al., Proc. Natl. Acad. Sci. USA 1986, 83: 1670 to 1674). The antibody-coding RNA according to the invention is therefore preferably modified compared with the native RNA such that this no longer contains such destabilizing sequences. This also applies to those sequence motifs which are recognized by possible endonucleases, for example the sequence GAACAAG, which is contained in the 3' UTR segment of the gene which codes for the transferrin receptor (Binder et al., EMBO J. 1994, 13: 1969 to 1980). These sequence motifs are also preferably eliminated in the antibody-coding RNA according to the invention.

A person skilled in the art is familiar with various methods which are suitable in the present case for substitution of codons in RNAs, i.e. substitution of codons in the antibody-coding RNA according to the invention. In the case of relatively short coding regions (which code for antibodies or antibody fragments as described here), for example, the total antibody-coding RNA according to the invention can be synthesized chemically using standard techniques such as are familiar to a person skilled in the art.

Nevertheless, base substitutions are preferably introduced using a DNA template for the preparation of the antibody-coding RNA according to the invention with the aid of techniques of the usual targeted mutagenesis (see, for example, Maniatis et al., Molecular Cloning: A Laboratory Manual, Cold Spring Harbor Laboratory Press, 3rd ed., Cold Spring Harbor, N.Y., 2001). In this method, for the preparation of the antibody-coding RNA according to the invention, a corresponding DNA molecule is therefore transcribed in vitro (see below). This DNA template optionally has a suitable promoter, for example a T3, T7 or SP6 promoter, for the in vitro transcription, which is followed by the desired nucleotide sequence for the antibody-coding RNA according to the invention to be prepared and a termination signal for the in vitro transcription. The DNA molecule which forms the template of the antibody-coding RNA construct to be prepared can be prepared by fermentative proliferation and subsequent isolation as part of a plasmid which can be replicated in bacteria. Plasmids which may be mentioned as suitable for this are, for example, the plasmids pT7Ts (GenBank accession number U26404; Lai et al., Development 1995, 121: 2349 to 2360), pGEM® series, for example pGEM®-1 (GenBank accession number X65300; from Promega) and pSP64 (GenBank accession number X65327); cf. also Mezei and Storts, Purification of PCR Products, in: Griffin and Griffin (ed.), PCR Technology: Current Innovation, CRC Press, Boca Raton, Fla., 2001.

Using short synthetic RNA or DNA oligonucleotides which contain short single-stranded transitions at the cleavage sites formed, or genes prepared by chemical synthesis, the desired nucleotide sequence can thus be cloned into a suitable plasmid by molecular biology methods with which a person skilled in the art is familiar (cf. Maniatis et al., (2001) supra). The RNA or DNA molecule is then cut out of the plasmid, in which it can be present in one or several copies, by digestion with restriction endonucleases.

According to a particular embodiment of the present invention, the antibody-coding (modified) RNA according to the invention described above, especially if the RNA is in the form of mRNA, can moreover have a 5' cap structure (a modified guanosine nucleotide). Examples of cap structures which may be mentioned, without being restricted thereto, are m7G(5')ppp (5'(A,G(5')ppp(5')A and G(5')ppp(5')G.

According to a further preferred embodiment of the present invention, the antibody-coding (modified) RNA according to the invention contains, especially if the RNA is in the form of mRNA, a poly-A tail on the 3' terminus of typically about 10 to 200 adenosine nucleotides, preferably about 10 to 100 adenosine nucleotides, more preferably about 20 to 70 adenosine nucleotides or even more preferably about 20 to 60 adenosine nucleotides.

According to another preferred embodiment of the present invention, the antibody-coding (modified) RNA according to the invention contains, especially if the RNA is in the form of mRNA, a poly-C tail on the 3' terminus of typically about 10 to 200 cytosine nucleotides (SEQ ID NO: 54), preferably about 10 to 100 cytosine nucleotides (SEQ ID NO: 55), more preferably about 20 to 70 cytosine nucleotides (SEQ ID NO: 56) or even more preferably about 20 to 60 (SEQ ID NO: 57) or even 10 to 40 cytosine nucleotides (SEQ ID NO: 58). The poly-C tail may be added to the poly-A tail or may substitute the poly-A tail.

According to a further embodiment, the antibody-coding (modified) RNA according to the invention can additionally contain a nucleic acid section which codes a tag for purification. Such tags include, but with-out being limited thereto, e.g. a hexahistidine tag (SEQ ID NO: 59) (His tag, polyhistidine tag), a streptavidin tag (Strep tag), an SBP tag (streptavidin-binding tag) a GST (glutathione S transferase) tag etc. The antibody-coding (modified) RNA according to the invention can furthermore encode a tag for purification via an antibody epitope (antibody-binding tag), e.g. a Myc tag, an Swal 1 epitope, a FLAG tag, an HA tag etc., i.e. via recognition of the epitope via the (immobilized) antibody.

For efficient translation of RNA, in particular mRNA, effective binding of the ribosomes to the ribosome binding site (Kozak sequence: GCCGCCACCAUGG (SEQ ID NO: 16), the AUG forms the start codon) is necessary. In this respect, it has been found that an increased A/U content around this site renders possible a more efficient ribosome binding to the RNA. According to another preferred embodiment of the present invention, the antibody-coding (modified) RNA according to the invention can therefore have an increased A/U content around the ribosome binding site, preferably an A/U content which is increased by 5 to 50%, more preferably one increased by 25 to 50% or more, compared with the native RNA.

According to one embodiment of the antibody-coding (modified) RNA according to the invention, it is furthermore possible to insert one or more so-called IRES (internal ribosomal entry site) into the RNA. An IRES can thus function as the sole ribosome binding site, but it can also serve to provide an antibody-coding (modified) RNA according to the invention which codes for several antibodies or antibody fragments or for at least one antibody or antibody fragment which are to be translated by the ribosomes independently of one another ("multicistronic RNA"). Such an RNA can code, for example, a complete sequence of an antibody, the corresponding coding regions of the heavy and light chain being linked (functionally) with one another by an IRES sequence. However, the heavy and light chain to be encoded by the inventive RNA may also be located in one single "cistron". According to the invention, the IRES sequences described are employed in particular for (virtually) simultaneous and uniform expression of the light and the heavy chains of the antibody coded by the RNA according to the invention. Examples of IRES sequences which can be used according to the invention are those from picornaviruses (e.g. FMDV), pestiviruses (CFFV), polioviruses (PV), encephalomyocarditis viruses (ECMV), foot and mouth disease viruses (FMDV), hepatitis C viruses (HCV), classical swine fever viruses (CSFV), murine leukoma virus (MLV), simian immunodeficiency viruses (SIV), cricket paralysis viruses (CrPV) or an SIRES sequence.

According to a further preferred embodiment of the present invention, the antibody-coding (modified) RNA according to the invention has, in the 5' and/or 3' untranslated regions, stabilizing sequences which are capable of increasing the half-life of the RNA in the cytosol. These stabilizing sequences can have a 100% sequence homology to naturally occurring sequences which occur in viruses, bacteria and eukaryotes, but can also be partly or completely synthetic in nature. The untranslated sequences (UTR) of the (3-globin gene, for example from Homo sapiens or Xenopus laevis, may be mentioned as an example of stabilizing sequences which can be used in the present invention. Another example of a stabilizing sequence has the general formula (C/U)CCAN$_x$CCC(U/A)Py$_x$UC(C/U)CC (SEQ ID NO: 17), which is contained in the 3' UTR of the very stable RNA which codes for α-globin, α-(I)-collagen, 15-lipoxygenase or for tyrosine hydroxylase (cf. Holcik et al., Proc. Natl. Acad. Sci. USA 1997, 94: 2410 to 2414). Such stabilizing sequences can of course be used individually or in combination with one another and also in combination with other stabilizing sequences known to a person skilled in the art.

In a further preferred embodiment, the antibody-coding (modified) RNA according to the invention can encode a secretory signal peptide, in addition to the antibodies as described here. Such signal peptides are (signal) sequences which conventionally comprise a length of from 15 to 30 amino acids and are preferably localized on the N-terminus of the coded antibody. Signal peptides typically render possible transport of a protein or peptide fused therewith (here e.g. an antibody) to or into a defined cell compartment, preferably the cell surface, the endoplasmic reticulum or the endosomal-lysosomal compartment. Examples of signal sequences which can be used according to the invention are e.g. signal sequences of conventional and non-conventional MHC molecules, cytokines, immunoglobulins, the invariant chain, Lamp1, tapasin, Erp57, calreticulin and calnexin, and all further membrane-located, endosomally-lysosomally or endoplasmic reticulum-associated proteins. The signal peptide of the human MHC class I molecule HLAA*0201 is preferably used.

Sequences which render possible transport of a protein or peptide fused therewith (here e.g. an antibody) to or into a defined cell compartment, preferably the cell surface, the nucleus, the nucleus region, the plasma membrane, the cytosol, the endoplasmic reticulum, the organelles, the mitochondria, the Golgi apparatus or the endosomal-lysosomal compartment, also include, without being limited thereto, so-called routing signals, sorting signals, retention signals or salvage signals and membrane topology-stop transfer signals (cf. Pugsley, A. P., Protein Targeting, Academic Press, Inc. (1989)) at the level of the RNA according to the invention. In this connection, localization sequences include nucleic acid sequences which encode e.g. signals, i.e. amino acid sequences, such as, for example, KDEL (SEQ ID NO: 18) (Munro, et al., Cell 48:899-907 (1987)) DDEL (SEQ ID NO: 19), DEEL (SEQ ID NO: 20), QEDL (SEQ ID NO: 21) and RDEL (SEQ ID NO: 22) (Hangejorden, et al., J. Biol. Chem. 266:6015 (1991)) for the endoplasmic reticulum; PKKKRKV (SEQ ID NO: 23) (Lanford, et al. Cell 46:575 (1986)) PQKKIKS (SEQ ID NO: 24) (Stanton, L. W., et al., Proc. Natl. Acad. Sci. USA 83:1772 (1986); QPKKP (SEQ ID NO: 25) (Harlow, et al., Mol. Cell. Biol. 5:1605 1985), and RKKR (SEQ ID NO:26) for the nucleus; and RKKRRQRRRAHQ (SEQ ID NO: 27) (Seomi, et al., J. Virology 64:1803 (1990)), RQARRNRRRRWRERQR (SEQ ID NO: 28) (Kubota, et al., Biochem. and Biophy, Res. Comm. 162:963 (1989)), and MPLTRRRPAASQALAPPTP (SEQ ID NO: 29) (Siomi, et al., Cell 55:197 (1988)) for the nucleus region; MDDQRDLISNNEQLP (SEQ ID. NO: 30) (Bakke, et al., Cell 63:707-716 (1990)) for the endosomal compartment (see, for example, Letourneur, et al., Cell 69:1183 (1992) for the targeting of liposomes). Myristoylation sequences can furthermore be used in order to lead the expressed protein or peptide (here e.g. an antibody) to the plasma membrane, or to certain various sub-cell compartments, such as the nucleus region, the organelles, the mitochondria and the Golgi apparatus. Corresponding amino acid sequences which are coded by a corresponding codon sequence of the RNA according to the invention are given below. The sequence MLFNLRXXLNNAAF-RHGHNFMVRNFRCGQPLX (SEQ ID NO: 31) can be used to lead the antibody to the mitochondrial matrix (Pugsley, supra). See Tang, et al., J. Bio. Chem. 207:10122, in respect of the localization of proteins (antibodies) to the Golgi apparatus; for the localization of proteins to the plasma membrane: GCVCSSNP (SEQ ID NO: 32), GQTVTTPL (SEQ ID NO: 33), GQELSQHE (SEQ ID NO: 34), GNSPSYNP (SEQ ID NO: 35), GVSGSKGQ (SEQ ID NO: 36), GQTITTPL (SEQ ID NO: 37), GQTLTTPL (SEQ ID NO: 38), GQIFSRSA (SEQ ID NO: 39), GQIHGLSP (SEQ ID NO: 40), GARASVLS (SEQ ID NO: 41), and GCTLSAEE (SEQ ID NO: 42); to the endoplasmic reticulum GQNLSTSN (SEQ ID NO: 43); to the nucleus GAALTILV (SEQ ID NO: 44) and GAALTLLG (SEQ ID NO: 45); to the endoplasmic reticulum and to the cytoplasm GAQVSSQK (SEQ ID NO: 46) and GAQLSRNT (SEQ ID NO: 47); to the Golgi apparatus, to the nucleus, to the cytoplasm and to the cytoskeleton: GNAAAAKK (SEQ ID NO: 48); to the cytoplasm and to the cytoskeleton GNEASYPL (SEQ ID NO: 49); and to the plasma membrane and to the cytoskeleton GSSKSKPK (SEQ ID NO: 50). Such sequences as described above are preferably used for RNAs which code for intrabodies, i.e. antibodies which are retained in the cell and are not secreted.

The modifications described here can be introduced into the antibody-coding RNA sequence according to the invention in a suitable manner by a person skilled in the art. For example, the optimum modified RNA according to the invention can be determined by methods known to the person skilled in the art, e.g. the G/C content can be adapted manually and/or by means of an automated method as disclosed in WO 02/098443. In this context, the RNA sequences can be adapted with the various additional optimization aims described here: On the one hand, the adaptation can be carried out with the highest possible G/C content, and on the other hand taking into the best possible account the frequency of the tRNAs according to codon usage. In this context, in the first step of the method a virtual translation of any desired RNA (or DNA) sequence is carried out in order to generate the corresponding amino acid sequence. Starting from the amino acid sequence, a virtual reverse translation is carried out, which on the basis of the degenerated genetic code provides selection possibilities for the corresponding codons. Depending on the optimization or modification required, corresponding selection lists and optimization algorithms are used for selection of the suitable codons. The algorithm is typically implemented on a computer with the aid of suitable software. The optimized RNA sequence is established in this way and can be displayed, for example, with the aid of an appropriate display device and compared with the original (wild-type) sequence. The same also applies to the frequency of the individual nucleotides. In this context, the changes compared with the original nucleotide sequence are preferably highlighted. According to a preferred embodiment, stable sequences which are known in nature and can provide the basis for an RNA stabilized in accordance with natural sequence motifs are furthermore read in. A secondary structure analysis which can analyse stabilizing and destabilizing properties or, respectively, regions of the RNA with the aid of structure calculations can likewise be envisaged.

Furthermore, according to a preferred embodiment effective transfer of the antibody-coding (modified) RNA according to the invention into the cells to be treated or the organism to be treated can be improved by complexing the antibody-coding (modified) RNA according to the invention with a cationic peptide or protein or binding it thereto. Such a complexing/condensing of the RNA, in particular mRNA, includes, for example, complexing (or binding) of the RNA according to the invention with a (poly)cationic polymer, polyplexes, protein(s), in particular polycationic protein(s), or peptide(s). Preferably, an RNA (mRNA) according to the invention is complexed or condensed with at least one cationic or polycationic agent. Preferably, such a cationic or polycationic agent is an agent which is chosen from the group consisting of protamine, poly-L-lysine, poly-L-arginine, nucleolin, spermin and histones, nucleolin or derivatives thereof. The use of protamine as a polycationic, nucleic acid-binding protein is particularly preferred. This procedure for stabilizing RNA is described, for example, in EP-A-1083232, the disclosure content of which in this respect is included in its full scope in the present invention.

According to a particular embodiment, the antibody-coding (modified) RNA according to the invention can contain a lipid modification. Such an RNA modified with a lipid typically comprises an antibody-coding RNA, as defined here, according to the invention, at least one linker covalently linked with this RNA and at least one lipid covalently linked with the particular linker. Alternatively, the (modified) RNA according to the invention modified with a lipid comprises (at least) one (modified) RNA, as defined here, according to the invention and at least one (bifunctional) lipid covalently linked with this RNA. According to a third alternative the (modified) RNA according to the invention modified with a lipid comprises a (modified) RNA, as defined here, according to the invention, at least one linker covalently linked with this RNA and at least one lipid linked covalently with the particular linker and at least one (bifunctional) lipid covalently linked (without a linker) with this (modified) RNA according to the invention.

The lipid employed for lipid modification of the antibody-coding (modified) RNA according to the invention is typically a lipid or a lipophilic residue, which is preferably biologically active per se. Such lipids preferably include natural substances, or compounds, such as e.g. vitamins, e.g. α-tocopherol (vitamin E), including RRR-α-tocopherol (formerly D-α-tocopherol), L-α-tocopherol, the racemate D,L-α-tocopherol, vitamin E succinate (VES) or vitamin A and derivatives thereof, e.g. retinic acid, retinol, vitamin D and derivatives thereof, e.g. vitamin D and ergosterol precursors thereof, vitamin E and derivatives thereof, vitamin K and derivatives thereof, e.g. vitamin K and related quinone or phytol compounds, or steroids, such as bile acids, for example cholic acid, deoxycholic acid, dehydrocholic acid, cortisone, digoxygenin, testosterone, cholesterol or thiocholesterol. Further lipids or lipophilic residues in the context of the present invention include, without being limited thereto, polyalkylene glycols, (Oberhauser et al., Nucl. Acids Res., 1992, 20, 533), aliphatic groups, such as e.g. $C_1$-$C_{20}$-alkanes, $C_1$-$C_{20}$-alkenes, or $C_1$-$C_{20}$-alkanol compounds etc., such as, for example, dodecanediol, hexadecanol or undecyl residues (Saison-Behmoaras et al., EMBO J, 1991, 10, 111; Kabanov et al., FEBS Lett., 1990, 259, 327; Svinarchuk et al., Biochimie, 1993, 75, 49), phospholipids, such as e.g. phosphatidylglycerol, diacylphosphatidylglycerol, phosphatidylcholine, dipalmitoylphosphatidylcholine, distearoylphosphatidylcholine, phosphatidylserine, phosphatidylethanolamine, dihexadecyl-rac-glycerol, sphingolipids, cerebrosides, gangliosides, or triethylammonium 1,2-di-O-hexadecyl-rac-glycero-3-H-phosphonate (Manoharan et al., Tetrahedron Lett., 1995, 36, 3651; Shea et al., Nucl. Acids Res., 1990, 18, 3777), polyamines or polyalkylene glycols, such as e.g. polyethylene glycol (PEG) (Manoharan et al., Nucleosides & Nucleotides, 1995, 14, 969), hexaethylene glycol (HEG), palmitin, or palmityl residues (Mishra et al., Biochim. Biophys. Acta, 1995, 1264, 229), octadecylamines, or hexylaminocarbonyloxycholesterol residues (Crooke et al., J. Pharmacol. Exp. Ther., 1996, 277, 923), and waxes, terpenes, alicyclic hydrocarbons, saturated or mono- or polyunsaturated fatty acid residues etc.

The linking between the lipid and the antibody-coding (modified) RNA according to the invention can in principle take place on any nucleotide, on the base or the sugar residue of any nucleotide, on the 3' and/or 5' end, and/or on the phosphate backbone of the antibody-coding (modified) RNA according to the invention. According to the invention, a terminal lipid modification of the (modified) RNA according to the invention on the 3' and/or 5' end thereof is particularly preferred. A terminal modification has several advantages over modifications within the sequence. On the one hand, modifications within the sequence can influence the hybridization properties, which may have an adverse effect in the case of sterically demanding residues. (Sterically demanding) modifications within the sequence very often also interfere in translation, which can frequently lead to an interruption in the protein synthesis. On the other hand, in the case of preparation by synthesis of a lipid-modified (modified) RNA according to the invention which is modified exclusively terminally, synthesis of this antibody-coding (modified) RNA according to the invention is carried out with monomers which are commercially available in large amounts, and synthesis protocols known in the prior art are used.

According to a first preferred embodiment, the linking takes place between the antibody-coding (modified) RNA according to the invention and at least one lipid via a linker (linked covalently with the (modified) RNA). Linkers in the context of the present invention typically contain at least two and optionally 3, 4, 5, 6, 7, 8, 9, 10, 10-20, 20-30 or more reactive groups, chosen from e.g. a hydroxyl group, an amino group, an alkoxy group etc. One reactive group preferably serves to bond the antibody-coding (modified) RNA according to the invention described here. This reactive group can be in a protected form, e.g. as a DMT (dimethoxytrityl chloride) group, as an Fmoc group, as an MMT (monomethoxytrityl) group, as a TFA (trifluoroacetic acid) group etc. Sulfur groups can furthermore be protected by disulfides, e.g. alkylthiols, such as, for example, 3-thiopropanol, or with activated components, such as 2-thiopyridine. According to the invention, one or more further reactive groups serve for covalent bonding of one or more lipids. According to the first embodiment, an antibody-coding (modified) RNA according to the invention can therefore bond at least one lipid via the covalently bonded linker, e.g. 1, 2, 3, 4, 5, 5-10, 10-20, 20-30 or more lipid(s), particularly preferably at least 3-8 or more lipids per (modified) RNA. In this context, the bonded lipids can be bonded separately from one another at various positions of the antibody-coding (modified) RNA according to the invention, but can also be in the form of a complex at one or more positions of the (modified) RNA. An additional reactive group of the linker can be used for direct or indirect (cleavable) bonding to a carrier material, e.g. a solid phase. Preferred linkers according to the present invention are e.g. glycol, glycerol and glycerol derivatives, 2-aminobutyl-1,3-propanediol and 2-aminobutyl-1,3-propanediol derivatives/matrix, pyrrolidine linkers or pyrrolidine-containing organic molecules (in particular for a modification on the 3' end) etc. According to the invention, glycerol or glycerol derivatives ($C_3$ anchor) or a 2-aminobutyl-1,3-propanediol derivative/matrix ($C_7$ anchor) are particularly preferably used as linkers. A glycerol derivative ($C_3$ anchor) as a linker is particularly preferred if the lipid modification can be introduced via an ether bond. If the lipid modification is to be introduced e.g. via an amide or an urethane bond, e.g. a 2-aminobutyl-1,3-propanediol matrix ($C_7$ anchor) is preferred. In this connection, the bond formed between the linker and the antibody-coding (modified) RNA according to the invention is preferably such that it is compatible with the conditions and chemicals of amidite chemistry, that is to say it is preferably neither acid- nor base-labile. In particular, those bonds which are readily accessible synthetically and are not hydrolysed by the ammoniacal cleavage procedure of a nucleic acid synthesis process are preferred. Possible bonds are in principle all appropriately suitable bonds, preferably ester bonds, amide bonds, urethane bonds and ether bonds. In addition to the good accessibility of the educts (few synthesis stages), the ether bond is particularly preferred in this context because of its relatively high biological stability to enzymatic hydrolysis.

According to a second preferred embodiment, for the lipid modification of the (modified) RNA according to the invention the linking of (at least one) (modified) RNA according to the invention takes place directly with at least one (bifunctional) lipid as described here, i.e. without using a linker as described here. In this case, the (bifunctional) lipid according to the invention preferably contains at least two reactive groups, or optionally 3, 4, 5, 6, 7, 8, 9, 10 or more reactive groups, a first reactive group serving for direct or indirect bonding of the lipid to a carrier material described here and at least one further reactive group serving for bonding of the (modified) RNA. According to the second embodiment, an antibody-coding (modified) RNA according to the invention can therefore preferably bond at least one lipid (directly without a linker), e.g. 1, 2, 3, 4, 5, 5-10, 10-20, 20-30 or more lipid(s), particularly preferably at least 3-8 or more lipids per (modified) RNA. In this context, the bonded lipids can be bonded separately from one another at various positions of the antibody-coding (modified) RNA according to the invention, but can also be in the form of a complex at one or more positions of the (modified) RNA. Alternatively, according to the second embodiment, at least one antibody-coding (modified) RNA, e.g. optionally 3, 4, 5, 6, 7, 8, 9, 10, 10-20, 20-30 or more (modified) RNAs, according to the invention can be bonded to a lipid as described above via reactive groups thereof. Lipids which can be used for this second embodiment particularly preferably include such (bifunctional) lipids which render possible a coupling (preferably on their termini or optionally intramolecularly), such as e.g. polyethylene glycol (PEG) and derivatives thereof, hexaethylene glycol (HEG) and derivatives thereof, alkanediols, aminoalkanes, thioalkanols etc. The bond between a (bifunctional) lipid and an antibody-coding (modified) RNA according to the invention as described above is preferably such as is described for the first preferred embodiment.

According to a third embodiment, for the lipid modification of the (modified) RNA according to the invention the linking between the antibody-coding (modified) RNA according to the invention and at least one lipid as described here takes place via both of the abovementioned embodiments simultaneously. Thus e.g. the antibody-coding (modified) RNA according to the invention can be linked at one position of the RNA with at least one lipid via a linker (analogously to the 1st embodiment) and at another position of the (modified) RNA directly with at least one lipid without using a linker (analogously to the 2nd embodiment). For example, at least one lipid as described here can be linked covalently with the RNA at the 3' end of the (modified) RNA via a linker, and a lipid as described here can be linked covalently with the RNA at the 5' end of the (modified) RNA without a linker. Alternatively, at least one lipid as described here can be linked covalently with the (modified) RNA at the 5' end of an antibody-coding (modified) RNA according to the invention via a linker, and a lipid as described here can be linked covalently with the (modified) RNA at the 3' end of the (modified) RNA without a linker. Covalent linkings can likewise take place not only on the termini of the antibody-coding (modified) RNA according to the invention, but also intramolecularly, as described above, e.g. on the 3' end and intramolecularly, on the 5' end and intramolecularly, on the 3' and 5' end and intramolecularly, exclusively intramolecularly etc.

The (modified) RNA according to the invention described here can be prepared by preparation processes known in the prior art, e.g. automatically or manually via known nucleic acid syntheses (see, for example, Maniatis et al. (2001) supra) or also via molecular biology methods, for example with subsequent purification, for example via chromatography methods.

According to further subject matter of the present invention, the antibody-coding (modified) RNA according to the invention can be used for the preparation of a pharmaceutical composition for treatment of tumours and cancer diseases, cardiovascular diseases, infectious diseases, autoimmune diseases or optionally monogenetic diseases, e.g. in gene therapy.

A pharmaceutical composition in the context of the present invention comprises an antibody-coding (modified) RNA as described here and optionally a pharmaceutically suitable carrier and/or further auxiliary substances and additives. The pharmaceutical composition employed according to the present invention typically comprises a safe and effective amount of a (modified) RNA as described here. As used here, "safe and effective amount" means an amount of the antibody-coding (modified) RNA according to the invention such as is sufficient to induce significantly, by expression of the coded antibody, a positive change of a state to be treated, e.g. a tumour disease or cancer disease, a cardiovascular disease or an infectious disease, as described in the following. At the same time, however, a "safe and effective amount" is low enough to avoid serious side effects in the therapy of these diseases, that is to say to render possible a reasonable ratio of advantage and risk. Determination of these limits typically lies within the range of reasonable medical judgement. The concentration of the antibody-coding (modified) RNA according to the invention in such pharmaceutical compositions can therefore vary, for example, without being limited thereto, within a wide range of from e.g. 0.1 ng to 1,000 mg/ml. Such a "safe and effective amount" of an antibody-coding (modified) RNA according to the invention can vary in connection with the particular state to be treated and the age and the physical state of the patient to be treated, the severity of the state, the duration of the treatment, the nature of the concomitant therapy, of the particular pharmaceutically suitable carrier used and similar factors within the knowledge and experience of the treating doctor. The pharmaceutical composition described here can be employed for human and also for veterinary medicine purposes.

The pharmaceutical composition according to the invention described here can optionally comprise a pharmaceutically suitable carrier (and/or vehicle). The term "pharmaceutically suitable carrier (and/or vehicle)" used here preferably includes one or more compatible solid or liquid carriers or vehicles, (e.g. fillers, or diluents or encapsulating compounds) which are suitable for administration to a person. The term "compatible" as used here means that the constituents of the composition are capable of being mixed together with the antibody-coding (modified) RNA according to the invention and the auxiliary substance optionally contained in the composition, as such and with one another in a manner such that no interaction occurs which would substantially reduce the pharmaceutical effectiveness of the composition under usual condition of use, such as e.g. would reduce the pharmaceutical activity of the coded antibody or even suppress or impair expression of the coded antibody. Pharmaceutically suitable carrier must of course have a sufficiently high purity and a sufficiently low toxicity to render them suitable for administration to a person to be treated.

Pharmaceutically suitable carriers or vehicles, that may be used in the inventive pharmaceutical composition, may be typically distinguished into solid or liquid carriers or vehicles, wherein a specific determination may depend on the viscosity of the respective carrier or vehicle to be used.

In this context, solid carriers and vehicles typically include e.g., but are not limited to, ion exchangers, alumina, aluminum stearate, lecithin, and salts, if provided in solid form, such as protamine sulfate, disodium hydrogen phosphate, potassium hydrogen phosphate, sodium chloride, zinc salts, colloidal silica, magnesium trisilicate, or polyvinyl pyrrolidone, waxes, polyethylene-polyoxypropylene-block polymers, wool fat, sugars, such as, for example, lactose, glucose and sucrose; starches, such as, for example, corn starch or potato starch; or cellulose-based substances, e.g. cellulose and its derivatives, such as, for example, sodium carboxymethylcellulose, ethylcellulose, cellulose acetate; pulverized tragacanth; malt; gelatine; tallow; solid lubricants, such as, for example, stearic acid, magnesium stearate; calcium sulfate; wetting agents, such as, for example, sodium lauryl sulfate; colouring agents; flavouring agents; drug (active agent) carriers; tablet-forming agents; stabilizers; antioxidants; preservatives; etc.

Liquid carriers or vehicles, e.g. for aqueous or oleaginous suspensions, typically include, but are not limited to, e.g., water; pyrogen-free water; solutions of ion exchangers, alumina, aluminum stearate, lecithin, or serum proteins, such as human serum albumin; alginic acid; isotonic saline solutions or phosphate-buffered solutions, Ringer's solution, isotonic sodium chloride solution, etc. or salts or electrolytes, if provided in solubilized form, such as protamine sulfate, phosphates, e.g. disodium hydrogen phosphate, potassium hydrogen phosphate, sodium chloride, zinc salts, or (other) buffer substances including e.g. glycine, sorbic acid, potassium sorbate; liquid solutions of polyols, such as, for example, polyethylene glycol, polypropylene glycol, glycerol, 1,3-butanediol, sorbitol, Mannitol; sterile, fixed oils, any suitable bland fixed oil, e.g. including synthetic mono- or di-glycerides, partial glyceride mixtures of saturated vegetable fatty acids, fatty acids, such as oleic acid and its glyceride derivatives, natural pharmaceuticallyacceptable oils, e.g. plant oils, such as, for example, groundnut oil, cottonseed oil, sesame oil, corn oil and oil from *Theobroma*; olive oil or castor oil, especially in their polyoxyethylated versions. These liquid carriers or vehicles may also contain or comprise a long-chain alcohol diluent or dispersant, such as carboxymethyl cellulose or similar dispersing agents, or commonly used surfactants or emulsifiers, such as Tween®, Spans and other emulsifying agents or bioavailability enhancers, etc., if provided in a liquid form.

The choice of a pharmaceutically suitable carrier as described above is determined in particular by the mode in which the pharmaceutical composition according to the invention is administered. The pharmaceutical composition according to the invention can be administered, for example, systemically. Administration routes include e.g. transdermal, oral, parenteral, including subcutaneous or intravenous injections, topical and/or intranasal routes. The suitable amount of the pharmaceutical composition according to the invention which is to be used can be determined by routine experiments using animal models. Such models include, but without being limited thereto, models of the rabbit, sheep, mouse, rat, dog and non-human primate models. Preferred unit dose forms for injection include sterile solutions of water, physiological saline solution or mixtures thereof. The pH of such solutions should be adjusted to about 7.4. Suitable carriers for injection include hydrogels, devices for controlled or delayed release, polylactic acid and collagen matrices. Pharmaceutically suitable carriers which can be used here include those which are suitable for use in lotions, creams, gels and the like. If the compound is to be administered perorally, tablets, capsules and the like are the preferred unit dose form. The pharmaceutically suitable carriers for the preparation of unit dose forms which can be used for oral administration are well-known in the prior art. Their choice will depend on secondary considerations, such as flavour, cost and storage stability, which are not critical for the purposes of the present invention and can be implemented without difficulties by a person skilled in the art.

The pharmaceutical composition according to the invention can furthermore comprise an injection buffer, which preferably improves the transfection and also the translation of the antibody-coding RNA according to the invention in cells or an organism. The pharmaceutical composition according to the invention can comprise, for example, an aqueous injection buffer which contains, with respect to the total pharmaceutical composition, if this is in liquid form, a sodium salt, preferably at least 50 mM sodium salt, a calcium salt, preferably at least 0.01 mM calcium salt, and optionally a potassium salt, preferably at least 3 mM potassium salt. According to a preferred embodiment, the sodium salts, calcium salts and optionally potassium salts contained in such an injection buffer are in the form of halides, e.g. chlorides, iodides or bromides, or in the form of their hydroxides, carbonates, bicarbonates or sulfates. Examples which are to be mentioned here are, for the sodium salt NaCl, NaI, NaBr, $Na_2CO_3$, $NaHCO_3$, $Na_2SO_4$, for the potassium salt optionally present KCl, KI, KBr, $K_2CO_3$, $KHCO_3$, $K_2SO_4$, and for the calcium salt $CaCl_2$, $CaI_2$, $CaBr_2$, $CaCO_3$, $CaSO_4$, $Ca(OH)_2$. The injection buffer can also contain organic anions of the above-mentioned cations. In a particularly preferred embodiment, such an injection buffer contains as salts sodium chloride (NaCl), calcium chloride ($CaCl_2$) and optionally potassium chloride (KCl), it also being possible for other anions to be present in addition to the chlorides.

These salts are typically present in the injection buffer optionally used in the pharmaceutical composition according to the invention, with respect to the total pharmaceutical composition (if this is in liquid form), in a concentration of at least 50 mM sodium chloride (NaCl), at least 3 mM potassium chloride (KCl) and at least 0.01 mM calcium chloride ($CaCl_2$). The injection buffer can be in the form of both hypertonic and isotonic or hypotonic injection buffers. In connection with the present invention, in this context the injection buffer is hypertonic, isotonic or hypotonic with respect to the particular reference medium, i.e. the injection buffer has either a higher, the same or a lower salt content compared with the particular reference medium, such concentrations of the abovementioned salts which do not lead to damage to the cells caused by osmosis or other concentration effects preferably being employed. Reference media here are, for example, liquids which occur in "in vivo" methods, such as, for example, blood, lymph fluid, cytosol fluids or other fluids which occur in the body, or liquids or buffers conventionally employed in "in vitro" methods. Such liquids and buffers are known to a person skilled in the art.

The injection buffer optionally contained in the pharmaceutical composition according to the invention can also contain further components, for example sugars (mono-, di-, tri- or polysaccharides), in particular glucose or mannitol. In a preferred embodiment, however, no sugars are present in the injection buffer used. It is also preferable for the injection buffer precisely to contain no non-charged components, such as, for example, sugars. The injection buffer typically contains exclusively metal cations, in particular from the group consisting of the alkali or alkaline earth metals, and anions, in particular the anions described above. The pH of the injection buffer used, with respect to the total pharmaceutical composition, if this is in liquid form, is preferably between 1 and 8.5, preferably between 3 and 5, more preferably between 5.5 and 7.5, in particular between 5.5 and 6.5. If appropriate, the injection buffer can also contain a buffer system which fixes the injection buffer at a buffered pH. This can be, for example, a phosphate buffer system, HEPES or $Na_2HPO_4/NaH_2PO_4$. However, the injection buffer used very particularly preferably contains none of the abovementioned buffer systems or contains no buffer system at all.

The injection buffer optionally contained in the pharmaceutical composition according to the invention can contain, in addition to or as an alternative to the monovalent and divalent cations described, divalent cations, in particular from the group consisting of alkaline earth metals, such as, for example, magnesium ($Mg^{2+}$), or also iron ($Fe^{2+}$), and monovalent cations, in particular from the groups consisting of alkali metals, such as, for example, lithium ($Li^+$). These monovalent cations are preferably in the form of their salts, e.g. in the form of halides, e.g. chlorides, iodides or bromides, or in the form of their hydroxides, carbonates, bicarbonates or sulfates. Examples which are to be mentioned here are, for the lithium salt LiCl, LiI, LiBr, $Li_2CO_3$, $LiHCO_3$, $Li_2SO_4$, for the magnesium salt $MgCl_2$, $MgI_2$, $MgBr_2$, $MgCO_3$, $MgSO_4$, and $Mg(OH)_2$, and for the iron salt $FeCl_2$, $FeBr_2$, $FeI_2$, $FeF_2$, $Fe_2O_3$, $FeCO_3$, $FeSO_4$, $Fe(OH)_2$. All the combinations of di- and/or monovalent cations, as described above, are likewise included. Such injection buffers which contain only divalent, only monovalent or di- and monovalent cations can thus be used in the pharmaceutical composition according to the invention. Such injection buffers which contain only one type of di- or monovalent cations, particularly preferably e.g. only $Ca^{2+}$ cations, or a salt thereof, e.g. $CaCl_2$, can likewise be used. The molarities given above for $Ca^{2+}$ (as a divalent cation) and $Na^{1+}$ (as a monovalent cation) (that is to say typically concentrations of at least 50 mM $Na^+$, at least 0.01 mM $Ca^{2+}$ and optionally at least 3 mM $K^+$) in the injection buffer can also be taken into consideration if another di- or monovalent cation, in particular other cations from the group consisting of the alkaline earth metals and alkali metals, are employed instead of some or all the $Ca^{2+}$ or, respectively, $Na^{1+}$ in the injection buffer used according to the invention for the preparation of the injection solution. All the $Ca^{2+}$ or $Na^{1+}$, as mentioned above, can indeed be replaced by other di- or, respectively, monovalent cations in the injection buffer used, for example also by a combination of other divalent cations (instead of $Ca^{2+}$) and/or a combination of other monovalent cations (instead of $Na^{1+}$) (in particular a combination of other divalent cations from the group consisting of the alkaline earth metals or, respectively, of other monovalent cations from the group consisting of the alkali metals), but it is preferable to replace at most some of the $Ca^{2+}$ or $Na^{1+}$, i.e. for at least 20%, preferably at least 40%, even more preferably at least 60% and still more preferably at least 80% of the particular total molarities of the mono- and divalent cations in the injection buffer to be occupied by $Ca^{2+}$ and, respectively, $Na^{1+}$. However, it is very particularly preferable if the injection buffer optionally contained in the pharmaceutical composition according to the invention contains exclusively $Ca^{2+}$ as a divalent cation and $Na^{1+}$ as a monovalent cation, that is to say, with respect to the total pharmaceutical composition, $Ca^{2+}$ represents 100% of the total molarity of divalent cations, just as $Na^{2+}$ represents 100% of the total molarity of monovalent cations. The aqueous solution of the injection buffer can contain, with respect to the total pharmaceutical composition, up to 30 mol % of the salts contained in the solution, preferably up to 25 mol %, preferably up to 20 mol %, furthermore preferably up to 15 mol %, more preferably up to 10 mol %, even more preferably up to 5 mol %, likewise more preferably up to 2 mol % of insoluble or sparingly soluble salts. Salts which are sparingly soluble in the context of the present invention are those of which the solubility product is $<10^4$. Salts which are readily soluble are those of which the solubility product is $>10^4$. Preferably, the injection buffer optionally contained in the pharmaceutical composition according to the invention is from 50 mM to 800 mM, preferably from 60 mM to 500 mM, more preferably from 70 mM to 250 mM, particularly preferably 60 mM to 110 mM in sodium chloride (NaCl), from 0.01 mM to 100 mM, preferably from 0.5 mM to 80 mM, more preferably from 1.5 mM to 40 mM in calcium chloride ($CaCl_2$) and optionally from 3 mM to 500 mM, preferably from 4 mM to 300 mM, more preferably from 5 mM to 200 mM in potassium chloride (KCl). Organic anions can also occur as further anions in addition to the abovementioned inorganic anions, for example halides, sulfates or carbonates. Among these there may be mentioned succinate, lactobionate, lactate, malate, maleate etc., which can also be present in combination.

An injection buffer optionally contained in the pharmaceutical composition according to the invention preferably contains lactate. If it contains an organic anion, such an injection buffer particularly preferably contains exclusively lactate as the organic anion. Lactate in the context of the invention can be any desired lactate, for example L-lactate and D-lactate. Lactate salts which occur in connection with the present invention are typically sodium lactate and/or calcium lactate, especially if the injection buffer contains only $Na^+$ as a monovalent cation and $Ca^{2+}$ as a divalent cation. An injection buffer optionally used in the pharmaceutical composition according to the invention and as described above preferably contains, with respect to the total pharmaceutical composition, from 15 mM to 500 mM, more preferably from 15 mM to 200 mM, and even more preferably from 15 mM to 100 mM lactate. In this context, it has been found that the use of an injection buffer with the components described above, optionally with or without lactate (in the following: "RL injection buffer" if it does not contain the component lactate, or "RL injection buffer with lactate" if it does contain the component lactate) for RNA injection solutions (i.e. injection solutions which contain RNA and are suitable for injection of this RNA) significantly increases both the transfer and the translation of the RNA into/in the cells/tissue of a host organism (mammal) compared with other injection buffers conventionally used in the prior art.

According to a particular embodiment, the pharmaceutical composition used here can also be provided as a passive vaccine (for passive immunization). In the present invention, without being restricted to a theory, passive immunization is based on the introduction of an antibody-coding (modified) RNA as described here into an organism, in particular into a cell, the coded antibody then being expressed, i.e. translated. As a result, binding of such molecules, e.g. nucleic acids or antigens, for which the coded antibody is specific can take place. Passive vaccines in connection with the present invention typically comprise a composition as described above for a pharmaceutical composition, the composition of such passive vaccines used being determined in particular by the mode in which they are administered. Preferably, the passive vaccines according to the invention are administered systemically or in some cases nonsystemically. Administration routes of such passive vaccines according to the invention typically include transdermal, oral, parenteral, including subcutaneous, intravenous, or intraarterial injections, topical and/or intranasal routes. Passive vaccines according to the invention are therefore preferably formulated in a liquid or solid form.

According to further preferred subject matter of the present invention, the antibody-coding (modified) RNA according to the invention or a pharmaceutical composition according to the invention is used for treatment of indications mentioned by way of example in the following. Without being limited thereto, diseases or states, for example, such as e.g. cancer or tumour diseases chosen from melanomas, malignant melanomas, colon carcinomas, lymphomas, sarcomas, blastomas, kidney carcinomas, gastrointestinal tumours, gliomas, prostate tumours, bladder cancer, rectal tumours, stomach cancer, oesophageal cancer, pancreatic cancer, liver cancer, mammary carcinomas (=breast cancer), uterine cancer, cervical cancer, acute myeloid leukaemia (AML), acute lymphoid leukaemia (ALL), chronic myeloid leukaemia (CML), chronic lymphocytic leukaemia (CLL), hepatomas, diverse virus-induced tumours, such as e.g. papilloma virus-induced carcinomas (e.g. cervix carcinoma=cervical cancer), adenocarcinomas, herpes virus-induced tumours (e.g. Burkitt's lymphoma, EBV-induced B cell lymphoma), hepatitis B-induced tumours (hepatocell carcinomas), HTLV-1- and HTLV-2-induced lymphomas, acusticus neurinoma, lung carcinomas (=lung cancer=bronchial carcinoma), small cell lung carcinomas, throat cancer, anal carcinoma, glioblastoma, rectum carcinoma, astrocytoma, brain tumours, retinoblastoma, basalioma, brain metastases, medulloblastomas, vaginal cancer, testicular cancer, thyroid carcinoma, Hodgkin's syndrome, meningeomas, Schneeberger's disease, pituitary tumour, mycosis fungoides, carcinoids, neurinoma, spinalioma, Burkitt's lymphoma, laryngeal cancer, kidney cancer, thymoma, corpus carcinoma, bone cancer, non-Hodgkin's lymphomas, urethral cancer, CUP syndrome, head/neck tumours, oligodendroglioma, vulval cancer, intestinal cancer, colon carcinoma, oesophageal carcinoma (=Oesophageal cancer), wart conditions, small intestine tumours, craniopharyngeomas, ovarian carcinoma, soft tissue tumours (sarcomas), ovarian cancer (=Ovarian carcinoma), pancreatic carcinoma (=pancreatic cancer), endometrium carcinoma, liver metastases, penis cancer, tongue cancer, gallbladder cancer, leukaemia, plasmocytoma, lid tumour, prostate cancer (=prostate tumours) etc., or infectious diseases such as, for example, influenza, malaria, SARS, yellow fever, AIDS, Lyme borreliosis, leishmaniasis, anthrax, meningitis, can be treated with the pharmaceutical composition described.

The antibody-coding (modified) RNA according to the invention or a pharmaceutical composition according to the invention can likewise be used for treatment of, for example, viral infectious diseases chosen from, without being limited thereto, AIDS, condyloma acuminata, molluscum contagiosum, dengue fever, three-day fever, Ebola virus, colds, early summer meningoencephalitis (ESME), influenza, shingles, hepatitis, herpes simplex type I, herpes simplex type II, herpes zoster, influenza, Japanese encephalitis, Lassa fever, Marburg virus, measles, foot and mouth disease, mononucleosis, mumps, Norwalk virus infection, Pfeiffer's glandular fever, smallpox, polio (poliomyelitis), pseuodcroup, infectious erythema, rabies, warts, West Nile fever, chickenpox, cytomegalovirus (CMV), caused by viruses chosen from, without being limited thereto, e.g. HIV, *orthopox variola* virus, *orthopox alastrim* virus, *parapox ovis* virus, *molluscum contagiosum* virus, herpes simplex virus 1, herpes simplex virus 2, herpes B virus, varicella zoster virus, pseudorabies virus, human cytomegaly virus, human herpes virus 6, human herpes virus 7, Epstein-Barr virus, human herpes virus 8, hepatitis B virus, chikungunya virus, O'nyong'nyong virus, rubivirus, hepatitis C virus, GB virus C, West Nile virus, dengue virus, yellow fever virus, louping ill virus, St. Louis encephalitis virus, Japan B encephalitis virus, Powassan virus, FSME virus, SARS-associated corona virus, human corona virus 229E, human corona virus Oc43, Torovirus, human T cell lymphotropic virus type I, human T cell lymphotropic virus type II, human immunodeficiency virus type 1, human immunodeficiency virus type 2, Lassa virus, lymphocytic choriomeningitis virus, Tacaribe virus, Junin virus, Machupo virus, Borna disease virus, Bunyamwera virus, California encephalitis virus, Rift Valley fever virus, sand fly fever virus, Toscana virus, Crimean-Congo haemorrhagic fever virus, Hazara virus, Khasan virus, Hantaan virus, Seoul virus, Prospect Hill virus, Puumala virus, Dobrava Belgrade virus, Tula virus, sin nombre virus, Lake Victoria Marburg virus, Zaire Ebola virus, Sudan Ebola virus, Ivory Coast Ebola virus, influenza virus A, influenza virus B, influenza viruses C, parainfluenza virus, measles virus, mumps virus, respiratory syncytial virus, human metapneumovirus, vesicular stomatitis Indiana virus, rabies virus, Mokola virus, Duvenhage virus, European bat lyssavirus 1+2, Australian bat lyssavirus, adenoviruses AF, human papilloma viruses, condyloma virus 6, condyloma virus 11, polyoma viruses, adeno-associated virus 2, rotaviruses, or orbiviruses etc.,
or bacterial infectious diseases, such as abortion (infectious, septic), prostatitis (prostate inflammation), anthrax, appendicitis (inflammation of the caecum), borreliosis, botulism, *Campylobacter, Chlamydia trachomatis* (inflammation of the urethra, conjunctiva), cholera, diphtheria, donavonosis, epiglottitis, louse-borne typhus, typhoid fever, gas gangrene, gonorrhoea, hare plague, *Helicobacter pylori*, whooping-cough, climatic bubo, osteomyelitis, legionnaires' disease, leprosy, listeriosis, pneumonia, meningitis, bacterial meningitis, anthrax, inflammation of the middle ear, *Mycoplasma hominis*, neonatal sepsis (chorioamnionitis), noma, paratyphoid fever, plague, Reiter's syndrome, Rocky Mountain spotted fever, *Salmonella* paratyphoid fever, *Salmonella* typhoid fever, scarlet fever, syphilis, tetanus, gonorrhoea, tsutsugamushi fever, tuberculosis, typhus, vaginitis (colpitis), soft chancre and infectious diseases caused by parasites, protozoa or fungi, such as amoebic dysentery, bilharziosis, Chagas' disease, *Echinococcus*, fish tapeworm, ichthyotoxism (ciguatera), fox tapeworm, mycosis pedis, dog tapeworm, candiosis, ptyriasis, the itch (scabies), cutaneous leishmaniasis, lamblian dysentery (giadiasis), lice, malaria, onchocercosis (river blindness), fungal diseases, beef tapeworm, schistosomiasis, sleeping sickness, pork tapeworm, toxoplasmosis, trichomoniasis, trypanosomiasis (sleeping sickness), visceral leishmaniasis, nappy dermatitis or dwarf tapeworm.

The antibody-coding (modified) RNA according to the invention or a pharmaceutical composition according to the invention can also be used for treatment of cardiovascular diseases chosen from, without being limited thereto, coronary heart disease, arteriosclerosis, apoplexy and hypertension, and neuronal diseases chosen from Alzheimer's disease, amyotrophic lateral sclerosis, dystonia, epilepsy, multiple sclerosis and Parkinson's disease etc.

The antibody-coding (modified) RNA according to the invention or a pharmaceutical composition according to the invention can furthermore be used for treatment of autoimmune diseases chosen from, without being limited thereto, autoimmune type I diseases or autoimmune type II diseases or autoimmune type III diseases or autoimmune type IV diseases, such as, for example, multiple sclerosis (MS), rheumatoid arthritis, diabetes, diabetes type I (diabetes mellitus), systemic lupus erythematosus (SLE), chronic polyarthritis, Basedow's disease, autoimmune forms of chronic hepatitis, colitis ulcerosa, allergy type I diseases, allergy type II diseases, allergy type III diseases, allergy type IV diseases, fibromyalgia, hair loss, Bechterew's disease, Crohn's disease, myasthenia gravis, neurodermatitis, polymyalgia rheumatica, progressive systemic sclerosis (PSS), psoriasis, Reiter's syndrome, rheumatic arthritis, psoriasis, vasculitis etc., or diabetes type II.

Diseases in the context of the present invention likewise include monogenetic diseases, i.e. (hereditary) diseases which are caused by an individual gene defect and are inherited according to Mendel's rules. Monogenetic diseases in the context of the present invention are preferably chosen from the group consisting of autosomally recessive hereditary diseases, such as, for example, adenosine deaminase deficiency, familial hypercholesterolaemia, Canavan's syndrome, Gaucher's disease, Fanconi's anaemia, neuronal ceroid lipofuscinoses, mucoviscidosis (cystic fibrosis), sickle cell anaemia, phenylketonuria, alcaptonuria, albinism, hypothyroidism, galactosaemia, alpha-1 antitrypsin deficiency, xeroderma pigmentosum, Ribbing's syndrome, mucopolysaccharidoses, cleft lip, jaw, palate, Laurence-Moon-Biedl-Bardet syndrome, short rib polydactyly syndrome, cretinism, Joubert's syndrome, progeria type II, brachydactyl), adrenogenital syndrome, and X chromosomal hereditary diseases, such as, for example, colour blindness, e.g. red-green blindness, fragile X syndrome, muscular dystrophy (Duchenne and Becker-Kiener type), haemophilia A and B, G6PD deficiency, Fabry's disease, mucopolysaccharidosis, Norrie's syndrome, retinitis pigmentosa, septic granulomatosis, X-SCID, ornithine transcarbamylase deficiency, Lesch-Nyhan syndrome, or from autosomally dominant hereditary diseases, such as, for example, hereditary angioedema, Marfan's syndrome, neurofibromatosis, progeria type I, osteogenesis imperfecta, Klippel-Trenaunay syndrome, Sturge-Weber syndrome, Hippel-Lindau syndrome and tuberous sclerosis. RNA according to the invention which encodes an antibody as described here can be used on monogenetic diseases in the context of the present invention, the coded antibody being able to intervene in a regulatory manner, and also as a therapy, for example by regulation of undesirable metabolism products, trapping of specific gene products, interference with undesired certain interactions of proteins, e.g. inhibiting certain undesired ligand/receptor interactions etc.

A (modified) RNA according to the invention which encodes an antibody can be employed in various ways for treatment of the abovementioned indications. Thus, cancer diseases, for example, can be treated by immunotherapy in addition or as an alternative to known therapies. For this, for example, an RNA according to the invention which codes for a bispecific antibody can be employed, the antibody recognizing on the one hand a surface antigen, such as e.g. CD3, on T cells and on the other hand a tumour antigen, such as e.g. Her2/neu, C20, EGFR or CA-125. As a result, T cells which are positive in respect of certain surface antigens and tumour cells which express the tumour antigen are brought spatially close, which improves the recognition of the tumour cells by the immune system and therefore increases the destruction of the tumour cells.

Furthermore, e.g. in cardiac infarction cases, for example, it is possible to employ an RNA according to the invention which codes for a bispecific antibody which recognizes on the one hand a stem cell antigen, such as e.g. CD45, and on the other hand an antigen of the target tissue, such as e.g. myosin light chain, in order to increase the concentration of stem cells in the heart muscle (see also Reusch et al. Anti-CD3×anti-epidermal growth factor receptor (EGFR) bispecific antibody redirects T-cell cytolytic activity to EGFR-positive cancers in vitro and in an animal model. Clin Cancer Res. 2006).

Furthermore, by using RNA according to the invention which codes bispecific antibodies, e.g. two different cell types can be brought into contact or spatially close by the coded antibodies. This is advantageous, for example, in order to concentrate a cell in a tissue or to bring two proteins, e.g. antigens, into contact with or spatially close to one another, e.g. ligand and receptor or proteins which must dimerize/oligomerize in order to become activated.

RNAs according to the invention as described here which code for intrabodies can also be employed for use on the abovementioned diseases, in particular infectious diseases, autoimmune diseases and neuronal diseases and also on monogenetic diseases. Thus, intrabodies can be used in order to inhibit, as e.g. bispecific intracellularly expressed antibodies, cytoplasmic proteins (be it proteins originating from the pathogenic organism or be it proteins from the host organism), as described above. For example, RNAs according to the invention which code for intrabodies can be employed in order to inhibit IL-2R (receptor of IL-2) or ErbB2 (Her2/neu) by the coded antibodies. RNAs according to the invention which code for intrabodies are also suitable for use on virus diseases, such as e.g. HIV-I. It has furthermore been possible to demonstrate e.g. that infection of mice with scrapie, a prion disease, can be prevented by expression of an scFv fragment against the prion protein (Vertrugno et al., KDEL-tagged ("KDEL" disclosed as SEQ ID NO: 18) anti-prion intrabodies impair PrP lysosomal degradation and inhibit scrapie infectivity. Biochem Biophys Res Commun. 2005; Marasco Wash., Intrabodies: turning the humoral immune system outside in for intracellular immunization, Gene Therapy (1997) 4: 11-15). RNAs according to the invention which code for intrabodies can furthermore be employed in order to bind and preferably to neutralize, by the coded antibodies, intracellularly expressed factors as described here, such as e.g. antigens, nucleic acids etc. (see above).

In this connection, the invention therefore also provides the use of an antibody-coding (modified) RNA according to the invention or of a pharmaceutical composition according to the invention, e.g. a passive vaccine according to the invention, for treatment of indications and diseases described here. This also includes, in particular, the use of the antibody-coding (modified) RNA according to the invention for passive immunization and, respectively, the use of the pharmaceutical composition described according to the invention as a passive vaccine. The use of the antibody-coding (modified) RNA according to the invention for the preparation of a pharmaceutical composition or a passive vaccine, as described here, for treatment of the indications described here is likewise included. The use of the antibody-coding (modified) RNA according to the invention for the preparation of a passive vaccine, as described here, for passive immunization against the abovementioned indications is also included.

In this connection, the invention therefore likewise provides the use of an antibody-coding (modified) RNA according to the invention, of the antibody thereby coded, of the pharmaceutical composition described here or of the passive vaccine according to the invention for therapeutic use or for inhibition/neutralization of a protein function in one of the indications described here. In this context, a protein function is preferably suppressed (neutralizing antibodies). In principle, any of the antibodies coded by the RNA according to the invention and described here simultaneously also has a neutralizing action by binding of its specific substrate. Examples include e.g. anti-CD4 antibodies for prevention of rejection of transplants, Avastin (see above), Herceptin (see above) etc.

In this connection, the invention therefore also furthermore provides the use of an antibody-coding (modified) RNA according to the invention, of the antibody thereby coded or of the pharmaceutical composition described here for therapeutic use for passive immunization by triggering an immunological effector function in the sense of a monoclonal antibody. In this context, e.g. therapy of tumour cells or pathogens, such as viruses or bacteria, in the indications as described here is rendered possible by expression and secretion of the antibody or antibody fragment. Hereby, the immune defense of the host is supported by the inventive RNA by triggering the innate, cellular or humoral immune system. Antibodies may be directed against immune suppressing factors or they may simulate the function of certain immunologically active cytokines by e.g. activating cytokine receptors.

Furthermore, in this connection an antibody-coding (modified) RNA according to the invention or the pharmaceutical composition according to the invention described here or the passive vaccine according to the invention can also be used as an immunosuppressant in the indications described above. For example, it has been possible to demonstrate that it was possible for antibodies against the CD40 ligand (CD154) or against CD3 to prevent or reduce the rejection of transplants. Such (modified) RNAs according to the invention which encode an antibody, the coded antibodies of which can bind to surface antigens or generally to surface factors of cells, such as e.g. MHC class I molecules, MHC class II molecules, T cell receptors, LMP2 molecules, LMP7 molecules, CD1, CD2, CD3, CD4, CD8, CD11, CD28, CD30, CD31, CD40, CD50, CD54, CD56, CD58, CD80, CD86, CD95, CD153, CD154, CD178, CD3=TCR (T cell receptor) etc. are therefore preferably employed for use as immunosuppressants.

In this connection, the invention also additionally provides the use of an antibody-coding (modified) RNA according to the invention or of the pharmaceutical composition described here for therapeutic use for expansion of (certain) cells in vitro or in vivo. For example, CD4- and CD25-positive cells and regulatory T cells can be stimulated to expansion by expression of the superantagonistic CD28 antibody. Regulatory T cells which can be multiplied by expression of the superantagonistic CD28 antibody play a role above all in autoimmune diseases (Beyersdorf N, Hanke T, Kerkau T, Hunig T. Superagonistic anti-CD28 antibodies:

potent activators of regulatory T cells for the therapy of autoimmune diseases. Ann Rheum Dis. 2005 November; 64).

An antibody-coding (modified) RNA according to the invention or the pharmaceutical composition described here can likewise be used on rheumatoid arthritis for prevention of inflammation reactions by antibodies against e.g. TNFα or other factors exacerbating the undesired immune response against e.g. the patients' proteins, as for the treatment of autoimmune diseases.

A (modified) RNA according to the invention which encodes anti-CD18 antibodies or the pharmaceutical composition described here or the passive vaccine according to the invention can furthermore also be used for reduction of inflammations by inhibition of leukocytes, e.g. in the above-mentioned indications.

The present invention furthermore also provides a method for treatment and/or prevention of the above-mentioned diseases and, respectively, for (preventive) passive immunization against the above-mentioned diseases, which comprises administration of the pharmaceutical composition according to the invention described, the passive vaccine according to the invention or, respectively, the RNA according to the invention to a patient, in particular a human. Such methods also relate to treatment of indications which are connected with the intra- and extracellular processes described above, with neutralization functions of antibodies, the abovementioned inhibition of certain (cell) functions by antibodies etc.

The present invention also provides an in vitro transcription method for the preparation of an antibody-coding (modified) RNA, comprising the following steps:
a) provision of a nucleic acid, in particular a cDNA, which codes for an antibody as described above;
b) addition of the nucleic acid, in particular a cDNA, which codes for an antibody to an in vitro transcription medium comprising an RNA polymerase, a suitable buffer, a nucleic acid mix comprising one or more optionally modified nucleotides as described above in exchange for one or more of the naturally occurring nucleotides A, G, C or U, and optionally one or more naturally occurring nucleotides A, G, C or U, if not all the naturally occurring nucleotides A, G, C or U are to be exchanged, and optionally an RNase inhibitor;
c) incubation of the nucleic acid, in particular a cDNA, which codes for an antibody in the in vitro transcription medium and in vitro transcription of the nucleic acid to give an antibody-coding optionally modified RNA according to the invention;
d) optionally purification of the antibody-coding (modified) RNA according to the invention and removal of the non-incorporated nucleotides from the in vitro transcription medium.

A nucleic acid as described in step a) of the in vitro transcription method according to the invention can be any nucleic acid as described here (for example single- or double-stranded DNA, cDNA etc.) which encodes an antibody as described here. DNA sequences, e.g. genomic DNA or fragments thereof, or plasmids which encode an antibody as described here, preferably in linearized form, are typically employed for this. The in vitro transcription can conventionally be carried out using a vector which has an RNA polymerase binding site. Any (expression) vectors known in the prior art, e.g. commercially obtainable (expression) vectors, can be used for this. Preferred (expression) vectors are, for example, those which have an SP6 or a T7 or T3 binding site upstream and/or downstream of the cloning site.

The nucleic acid sequences used can thus be transcribed later as desired, depending on the RNA polymerase chosen. A nucleic acid sequence which is used for the in vitro transcription and codes for an antibody as described here is typically cloned into the (expression) vector, e.g. via a multiple cloning site of the vector used. Before the transcription, the (expression) vector is typically cleaved with restriction enzymes at the site at which the future 3' end of the RNA is to be found, using a suitable restriction enzyme, and the fragment is purified. This excludes the transcribed RNA from containing vector sequences, and an RNA transcript of defined length is obtained. In this context, preferably no restriction enzymes which generate overhanging ends (such as e.g. Aat II, Apa I, Ban H, Bgl I, Bsp 1286, BstX I, Cfo I, Hae II, HgiA I, Hha I, Kpn I, Pst I, Pvu I, Sac I, Sac II, Sfi I, Sph I etc.) are used. Should such restriction enzymes nevertheless be used, the overhanging 3' end is preferably filled up, e.g. with Kienow or T4 DNA polymerase.

As an alternative for step a) the nucleic acid can also be prepared as a transcription template by a polymerase chain reaction (PCR). For this, one of the primers used typically contains the sequence of an RNA polymerase binding site. Furthermore, the 5' end of the primer used preferably contains an extension of about 10-50 further nucleotides, more preferably of from 15 to 30 further nucleotides and most preferably of about 20 nucleotides.

Before the in vitro transcription, the nucleic acid, e.g. the DNA or cDNA, template is typically purified and freed from RNase in order to ensure a high yield. Purification can be carried out with the aid of any method known in the prior art, for example using a caesium chloride gradient, ion exchange methods or by purification via agarose gel electrophoresis.

According to method step b), the nucleic acid (used as the transcription template) is added to an in vitro transcription medium. A suitable in vitro transcription medium initially comprises a nucleic acid as provided under step a), for example about 0.1-10 μg, preferably about 1-5 μg, more preferably 2.5 μg and most preferably about 1 μg of such a nucleic acid. A suitable in vitro transcription medium furthermore optionally comprises a reducing agent, e.g. DTT, more preferably about 1-20 μl 50 mM DTT, even more preferably about 5 μl 50 mM DTT. The in vitro transcription medium furthermore comprises nucleotides, e.g. a nucleotide mix, in the case of the present invention comprising a mixture of (modified) nucleotides as defined here (typically about 0.1-10 mM per nucleotide, preferably 0.1 to 1 mM per nucleotide (preferably about 4 mM in total)) and optionally non-modified nucleotides. If modified nucleotides as defined here (about 1 mM per nucleotide, preferably about 4 mM in total), e.g. pseudouridine 5'-triphosphate, 5-methylcytidine 5'-triphosphate etc., are employed, they are typically added in an amount such that the modified or base-modified nucleotides is completely replaced by the natural nucleotide. However, it is also possible to employ mixtures of one or more modified or base-modified nucleotides and one or more naturally occurring nucleotides instead of a particular nucleotide, i.e. it is thus possible to employ one or more modified nucleotides as described above in exchange for one or more of the naturally occurring nucleotides A, G, C or U, and optionally additionally one or more naturally occurring nucleotides A, G, C or U, if not all the naturally occurring nucleotides A, G, C or U are to be exchanged. Conversely, it is also possible to use only natural nucleotides. By selective addition of the desired nucleotide to the in vitro transcription medium the content, i.e. the occurrence and the amount, of the desired modification of nucleotides in the transcribed antibody-coding (modified) RNA sequence can therefore be controlled. A suitable in vitro transcription medium likewise comprises an RNA polymerase, e.g. 17 RNA polymerase (for example T7-Opti mRNA Kit, CureVac, Tubingen, Germany), T3 RNA polymerase or SP6, typically about 10 to 500 U, preferably about 25 to 250 U, more preferably about 50 to 150 U, and most preferably about 100 U of RNA polymerase. The in vitro transcription medium is furthermore preferably kept free from RNase in order to avoid degradation of the transcribed RNA. A suitable in vitro transcription medium therefore optionally additionally comprises an RNase inhibitor.

The nucleic acid is incubated in the in vitro transcription medium in a step c) and is transcribed to an antibody-coding (modified) RNA. The incubation times are typically about 30 to 240 minutes, preferably about 40 to 120 minutes and most preferably about 90 minutes. The incubation temperatures are typically about 30-45° C., preferably 37-42° C. The incubation temperature depends on the RNA polymerase used, e.g. for T7 RNA polymerase it is about 37° C. The RNA obtained by the transcription is preferably an mRNA. The yields obtained in the in vitro transcription are, for the stated starting amounts employed in step b), typically in the region of about 30 µg of RNA per µg of template DNA used. In the context of the present invention, the yields obtained in the in vitro transcription can be increased by linear up scaling. For this, the stated starting amounts employed in step b) are preferably increased according to the yields required, e.g. by a multiplication factor of 5, 10, 50, 100, 500, 1,000, 5,000, 10,000, 50,000, 100,000 etc.

After the incubation, a purification of the transcribed antibody-coding (modified) RNA can optionally take place in step d) of the in vitro transcription method according to the invention. Any suitable method known in the prior art, e.g. chromatographic purification methods, e.g. affinity chromatography, gel filtration etc., can be used for this. By the purification, non-incorporated, i.e. excess nucleotides and template DNA can be removed from the in vitro transcription medium and a clean (modified) RNA can be obtained. For example, after the transcription the reaction mixture containing the transcribed RNA can typically be digested with DNase in order to remove the DNA template still contained in the reaction mixture. The transcribed RNA can be subsequently or alternatively precipitated with LiCl. Purification of the transcribed RNA can then take place via IP RP-HPLC. This renders it possible in particular to separate longer and shorter fragments from one another effectively.

Preferably, in this context the purification takes place via a method for purification of RNA on a preparative scale, which is distinguished in that the RNA is purified by means of HPLC using a porous reverse phase as the stationary phase (PURE Messenger). For example, for the purification in step d) of the in vitro method according to the invention, a reverse phase can be employed as the stationary phase for the HPLC purification. For the chromatography with reverse phases, a non-polar compound typically serves as stationary phase, and a polar solvent, such as mixtures of water, which is usually employed in the form of buffers, with acetonitrile and/or methanol, serves as the mobile phase for the elution. Preferably, the porous reverse phase has a particle size of 8.0±2 µm, preferably ±1 µm, more preferably +/−0.5 µm. The reverse phase material can be in the form of beads. The purification can be carried out in a particularly favourable manner with a porous reverse phase having this particle size, optionally in the form of beads, particularly good separation results being obtained. The reverse phase employed is preferably porous since with stationary reverse phases which are not porous, such as are described e.g. by Azarani A. and Hecker K. H., pressures which are too high are built up, so that preparative purification of the RNA is possible, if at all, only with great difficulty. The reverse phase preferably has a pore size of from 200 Å to 5,000 Å, in particular a pore size of from 300 Å to 4,000 Å. Particularly preferred pore sizes for the reverse phases are 200-400 Å, 800-1,200 Å and 3,500-4,500 Å. With a reverse phase having these pore sizes, particularly good results are achieved in respect of the purification of the RNA in process step d). The material for the reverse phase is preferably a polystyrene-divinylbenzene, and non-alkylated polystyrene-divinylbenzenes can be employed in particular. Stationary phases with polystyrene-divinylbenzene are known per se. For the purification in method step d), the polystyrene-divinylbenzenes which are known per se and already employed for HPLC methods and are commercially obtainable can be used. A non-alkylated porous polystyrene-divinylbenzene which in particular has a particle size of 8.0±0.5 µm and a pore size of 250-300 Å, 900-1,100 Å or 3,500-4,500 Å is very particularly preferably used for the purification in method step d). The advantages described above can be achieved in a particularly favourable manner with this material for the reverse phases. The HPLC purification can be carried out by the ion pair method, an ion having a positive charge being added to the mobile phase as a counter-ion to the negatively charged RNA. An ion pair having a lipophilic character, which is slowed down by the non-polar stationary phase of the reverse phase system, is formed in this manner. In practices, the precise conditions for the ion pair method must be worked out empirically for each concrete separation problem. The size of the counter-ion, its concentration and the pH of the solution contribute greatly towards the result of the separation. In a favourable manner, alkylammonium salts, such as triethylammonium acetate and/or tetraalkylammonium compounds, such as tetrabutylammonium, are added to the mobile phase. Preferably, 0.1 M triethylammonium acetate is added and the pH is adjusted to about 7. The choice of mobile phase depends on the nature of the desired separation. This means that the mobile phase found for a specific separation, such as can be known, for example, from the prior art, cannot be transferred readily to another separation problem with adequate prospect of success. The ideal elution conditions, in particular the mobile phase used, must be determined for each separation problem by empirical experiments. A mixture of an aqueous solvent and an organic solvent can be employed as the mobile phase for elution of the RNA by the HPLC method. In this context, it is favourable if a buffer which has, in particular, a pH of about 7, for example 6.5-7.5, e.g. 7.0, is used as the aqueous solvent; preferably, the buffer triethylammonium acetate is used, particularly preferably a 0.1 M triethylammonium acetate buffer which, as described above, also acts as a counter-ion to the RNA in the ion pair method. The organic solvent employed in the mobile phase can be acetonitrile, methanol or a mixture of these two, very particularly preferably acetonitrile. The purification of the RNA in method step d) using an HPLC method as described is carried out in a particularly favourable manner with these organic solvents. The mobile phase is particularly preferably a mixture of 0.1 M triethylammonium acetate, pH 7, and acetonitrile. It has emerged to be likewise particularly favourable if the mobile phase contains 5.0 vol. % to 20.0 vol. % of organic solvent, based on the mobile phase, and the remainder to make up 100 vol. % is the aqueous solvent. It is very particularly favourable for the method according to the invention if the mobile phase contains 9.5 vol. % to 14.5 vol. % of organic solvent, based on the mobile phase, and the remainder to make up 100 vol. % is the aqueous solvent. Elution of the RNA can subsequently be carried out isocratically or by means of a gradient separation. In the case of an isocratic separation, elution of the RNA is carried out with a single eluting agent or a mixture of several eluting agents which remains constant, it being possible for the solvents described above in detail to be employed as the eluting agent.

The present invention also provides an in vitro transcription and translation method for expression of an antibody, comprising the following steps:
a) provision of a nucleic acid, in particular a cDNA, which encodes an antibody as described above;
b) addition of the nucleic acid to an in vitro transcription medium comprising an RNA polymerase, a suitable buffer, a nucleic acid mix comprising one or more (modified) nucleotides as described above in exchange for one or more of the naturally occurring nucleotides A, G, C or U, and optionally one or more naturally occurring nucleotides A, G, C or U, if not all the naturally occurring nucleotides A, G, C or U are to be exchanged, and optionally an RNase inhibitor;
c) incubation of the nucleic acid, in particular a cDNA, in the in vitro transcription medium and in vitro transcription of the nucleic acid to give an antibody-coding (modified) RNA according to the invention;
d) optionally purification of the antibody-coding (modified) RNA according to the invention and removal of the non-incorporated nucleotides from the in vitro transcription medium;
e) addition of the (modified) RNA obtained in step c) (and optionally in step d) to an in vitro translation medium; incubation of the (modified) RNA in the in vitro translation medium and in vitro translation of the antibody coded by the (modified) RNA;
g) optionally purification of the antibody translated in step f).

Steps a), b), c) and d) of the in vitro transcription and translation method according to the invention for expression of an antibody are identical to steps a), b), c) and d) of the in vitro transcription method according to the invention described here.

In step e) of the in vitro transcription and translation method according to the invention for expression of an antibody, the (modified) RNA transcribed in step c) (and optionally purified in step d) is added to a suitable in vitro translation medium. A suitable in vitro translation medium comprises, for example, reticulocyte lysate, wheat germ extract etc. Such a medium conventionally furthermore comprises an amino acid mix. The amino acid mix typically comprises (all) naturally occurring amino acids and optionally modified amino acids, e.g. $^{35}$S-methionine (for example for monitoring the translation efficiency via autoradiography). A suitable in vitro translation medium furthermore comprises a reaction buffer. In vitro translation media are described, for example, in Krieg and Melton (1987) (P. A. Krieg and D. A. Melton (1987) In vitro RNA synthesis with SP6 RNA polymerase; Methods Enzymol 155:397-415), the disclosure content of which in this respect is included in its full scope in the present invention.

In a step f) of the in vitro transcription and translation method according to the invention for expression of an antibody, the (modified) nucleic acid is incubated in the in vitro translation medium and the antibody coded by the (modified) nucleic acid is translated in vitro. The incubation typically lasts about 30 to 240 minutes, preferably about 40 to 120 minutes and most preferably about 90 minutes. The incubation temperature is typically in a range of about 20-40° C., preferably about 25 to 35° C. and most preferably about 30° C.

Steps b) to f) of the in vitro transcription and translation method according to the invention for expression of an anti-body or individual steps of steps b) to f) can be combined with one another, i.e. can be carried out together. In this context, all the necessary components are preferably added to the reaction medium together at the start or successively during the reaction in accordance with the sequence of the steps b) to f) described.

The translated antibody obtained in step f) can be purified in an optional step g). A purification can be carried out with methods which are known to a person skilled in the art from the prior art, e.g. chromatography, such as, for example, affinity chromatography (HPLC, FPLC, etc.), ion exchange chromatography, gel chromatography, size exclusion chromatography, gas chromatography, or antibody detection, or biophysical methods, such as e.g. NMR analyses, etc. (see e.g. Maniatis et al. (2001) supra). Chromatography methods, including affinity chromatography methods, can employ tags in a suitable manner for the purification, as described above, e.g. a hexahistidine tag (SEQ ID NO: 59) (His tag, polyhistidine tag), a streptavidin tag (Strep tag), an SBP tag (streptavidin-binding tag), a GST (glutathione S transferase) tag etc. The purification can furthermore be carried out via an antibody epitope (antibody-binding tag), e.g. a Myc tag, an Swal 1 epitope, a FLAG tag, an HA tag etc., i.e. via recognition of the epitope via a corresponding (immobilized) antibody. The purification can likewise be carried out via the immobilized substrate of the specific antibody, i.e. by binding of the antibody to an immobilized antigen which is recognized and, respectively, bound specifically by the translated antibody.

The present invention also provides an in vitro transcription and translation method for expression of an antibody in a host cell, comprising the following steps:
a) provision of a nucleic acid, in particular a cDNA, which encodes an antibody as described above;
b) addition of the nucleic acid to an in vitro transcription medium comprising an RNA polymerase, a suitable buffer, one or more (modified) nucleotides as described above in exchange for one or more of the naturally occurring nucleotides A, G, C or U and optionally one or more naturally occurring nucleotides A, G, C or U, if not all the naturally occurring nucleotides A, G, C or U are to be exchanged;
c) incubation of the nucleic acid, in particular a cDNA, in the in vitro transcription medium and in vitro transcription of the nucleic acid to give an antibody-coding (modified) RNA according to the invention;
d) optionally purification of the antibody-coding (modified) RNA according to the invention and removal of the non-incorporated nucleotides from the in vitro transcription medium;
e') transfection of the (modified) RNA obtained in step c) (and optionally d)) into a host cell;
f') incubation of the (modified) nucleic acid in the host cell and translation of the antibody coded by the (modified) RNA in the host cell;
g') optionally isolation and/or purification of the antibody translated in step f').

Steps a), b), c) and d) of the in vitro transcription and translation method according to the invention for expression of an antibody in a host cell are identical to steps a), b), c) and d) of the in vitro transcription method according to the invention described here and of the in vitro transcription and translation method according to the invention described here for expression of an antibody.

According to step e') of the in vitro transcription and translation method according to the invention, transfection of the (modified) RNA obtained in step c) (and optionally in step d)) into a host cell is carried out. The transfection is in general carried out via transfection methods known in the prior art (see, for example, Maniatis et al. (2001) Molecular Cloning: A laboratory manual, Cold Spring Harbor Laboratory Press, Cold Spring Harbor, N.Y.). Suitable transfection methods in the context of the present invention include, without being limited thereto, e.g. electroporation methods, including modified electroporation methods (e.g. nucleofection), calcium phosphate methods, e.g. the calcium coprecipitation method, the DEAE-dextran method, the lipofection method, e.g. the transferrin-mediated lipofection method, polyprene transfection, particle bombardment, nanoplexes, e.g. PLGA, polyplexes, e.g. PEI, protoplast fusion and the microinjection method, the lipofection method having emerged in particular as a suitable method. In this context, the (modified) RNA according to the invention can be in the naked or complexed form, as described above for the (modified) RNA according to the invention.

In connection with the present invention and with step e') of the in vitro transcription and translation method according to the invention for expression of an antibody in a host cell, a (suitable) host cell includes any cell which allows expression of the antibody coded by the (modified) RNA according to the invention, preferably any cultured eukaryotic cell (e.g. yeast cells, plant cells, animal cells and human cells) or prokaryotic cell (e.g. bacteria cells etc.). Cells of multicellular organisms are preferably chosen for expression of the antibody coded by the (modified) RNA according to the invention if posttranslational modifications, e.g. glycosylation of the coded protein, are necessary (N- and/or O-coupled). In contrast to prokaryotic cells, such (higher) eukaryotic cells render possible posttranslational modification of the protein synthesized. The person skilled in the art knows a large number of such higher eukaryotic cells or cell lines, e.g. 293T (embryonal kidney cell line), HeLa (human cervix carcinoma cells), CHO (cells from the ovaries of the Chinese hamster) and further cell lines, including such cells and cell lines developed for laboratory purposes, such as, for example, hTERT-MSC, HEK293, Sf9 or COS cells. Suitable eukaryotic cells furthermore include cells or cell lines which are impaired by diseases or infections, e.g. cancer cells, in particular cancer cells of any of the types of cancer mentioned here in the description, cells impaired by HIV, and/or cells of the immune system or of the central nervous system (CNS). Human cells or animal cells, e.g. of animals as mentioned here, are particularly preferred as eukaryotic cells. Suitable host cells can likewise be derived from eukaryotic microorganisms, such as yeast, e.g. *Saccharomyces cerevisiae* (Stinchcomb et al., Nature, 282:39, (1997)), *Schizosaccharomyces pombe, Candida, Pichia*, and filamentous fungi of the genera *Aspergillus, Penicillium*, etc. Suitable host cells likewise include prokaryotic cells, such as e.g. bacteria cells, e.g. from *Escherichia coli* or from bacteria of the genera *Bacillus, Lactococcus, Lactobacillus, Pseudomonas, Streptomyces, Streptococcus, Staphylococcus*, preferably *E. coli*, etc.

In step f') of the in vitro transcription and translation method according to the invention for expression of an antibody in a host cell, incubation of the (modified) RNA in the host cell and translation of the antibody coded by the (modified) RNA in the host cell are carried out. Expression mechanisms intrinsic to the host cell are preferably used for this, e.g. by translation of the RNA in the host cell via ribosomes and tRNAs. The incubation temperatures used in this context depend on the particular host cell systems used.

In an optional step g'), the translated antibody obtained in step f') can be isolated and/or purified. In this context, an isolation of the translated (expressed) antibody typically comprises separating off the antibody from reaction constituents, and can be carried out by methods which are known to a person skilled in the art, for example by cell lysis, breakdown by ultrasound, or similar methods, including the abovementioned methods. A purification can therefore also be carried out by methods as described for step e) of the in vitro transcription and translation method according to the invention for expression of an antibody.

For purification of (recombinant) antibodies from a host cell in step g') of the method described above, a different choice of the host cells described above is necessary, depending on the use. Thus, the production of recombinant antibodies in *E. coli* typically is possible to only a limited extent, since the antibodies coded by a (modified) RNA according to the invention are very complex, require complicated folding mechanisms and are conventionally modified posttranslationally for use in multicellular organisms or beings. These mechanisms conventionally cannot be implemented in the cytoplasm of *E. coli*. Periplasmic production in *E. coli*, in which correct folding and modification of the antibody fragments is possible, can therefore be used. In this context, the purification usually requires an involved breakdown of the bacteria and a difficult separating off of all the bacterial constituents which can act as endotoxins during a therapeutic use. To bypass these purification problems, expression systems for yeasts, insect cells, mammalian cells and plants can be employed according to the invention in such cases, the production preferably being carried out in suitable mammalian cells, such as e.g. hamster cells (CHO), as described here.

Regardless of steps (a) to (d), the antibody coded by the (modified) RNA according to the invention can also be expressed by an in vitro translation method of steps (e') to (g'), which is also subject matter of the present invention as such.

The present invention also provides an in vitro transcription and in vivo translation method for expression of an anti-body in an organism, comprising the following steps:
a) provision of a nucleic acid, in particular a cDNA, which encodes an antibody as described above;
b) addition of the nucleic acid to an in vitro transcription medium comprising an RNA polymerase, a suitable buffer, a nucleic acid mix comprising one or more (modified) nucleotides as described above in exchange for one or more of the naturally occurring nucleotides A, G, C or U, and optionally one or more naturally occurring nucleotides A, G, C or U, if not all the naturally occurring nucleotides A, G, C or U are to be exchanged, and optionally an RNase inhibitor;
c) incubation of the nucleic acid, in particular a cDNA, in the in vitro transcription medium and in vitro transcription of the nucleic acid to give a (modified) RNA according to the invention as described here;
d) optionally purification and removal of the non-incorporated nucleotides from the in vitro transcription medium;
e") transfection of the (modified) RNA obtained in step c) (and optionally in step d)) into a host cell and transplanting of the transfected host cell into an organism;
f") translation of the antibody coded by the (modified) RNA in the organism.

Steps a), b), c) and d) of the in vitro transcription and in vivo translation method according to the invention for expression of an antibody in an organism are identical to steps a), b), c) and d) of the in vitro transcription method according to the invention described here, of the in vitro transcription and translation method according to the invention described here for expression of an antibody and of the in vitro transcription and translation method according to the invention described here for expression of an antibody in a host cell.

Host cells in the context of the present invention, and in particular in step e″), can also include autologous cells, i.e. cells which are taken from a patient and returned again (endogenous cells). Such autologous cells reduce the risk of rejection by the immune system in the case of in vivo uses. In the case of autologous cells, (healthy or diseased) cells from the affected body regions/organs of the patient are preferably employed. Transfection methods are preferably those as described above for step e). In step e″), transplanting of the host cell into an organism is carried out, additionally to step e). An organism or a being in connection with the present invention typically means mammals, i.e. animals, including cattle, pig, dog, cat, donkey, monkey, including rodents, e.g. mouse, hamster, rabbit etc., and humans. As an alternative to step e″) and f'), the isolation and/or purification can be carried out according to steps f)/f″) and/or g)/g') and the translated (therapeutically active) protein can be administered subsequently to the being. The administration can be carried out as described for pharmaceutical compositions.

In step f″), translation of the antibody coded by the (modified) RNA is carried out in the organism. In this context, the translation is preferably carried out by means of systems specific to the host cell, depending on the host cell used.

Regardless of steps (a) to (d), the transcribed (modified) RNA according to the invention can also be expressed by an in vitro translation method of steps (e″) to (g″), which is also subject matter of the present invention as such.

As an alternative to the methods described above, according to a particularly preferred embodiment in a further step e‴) a (modified) RNA according to the invention transcribed according to steps a) to d) can be administered directly into the organism, e.g. human, e.g. by administration of the naked or complexed RNA according to the invention, for example using the transfection methods described above, optionally using certain stabilizing factors described here. In this context, after uptake the RNA is preferably transported into the cells, e.g. with localization or signal sequences as described here, and preferably translated into the coded antibody in the cells.

Advantages of the Invention

The present invention describes in particular an antibody-coding RNA according to the invention. This can be modified or non-modified, where the definition of "modification" is to be understood in the broadest sense. A native RNA covalently bonded to another group, for example a lipid or a sugar residue, is modified in the context of this invention. An RNA which contains non-natively occurring constituents, for example non-native nucleotides, or an RNA which is modified with respect to its precursor by exchange of nucleotides, regardless of whether these are native or non-native, is also modified in the context of the invention. The great advantage of such RNAs is that these do not have the negative actions of DNA transfections (with stable incorporation into the genome). In the case of modified antibody-coding RNAs, the limited stability of the RNA coding for the antibodies or antibody fragments is moreover improved. According to the invention, after administration to patients, in particular mammals, above all humans, the antibodies are therefore thus expressed in vivo for only an estimatable time beyond the treatment and therefore do not lead to harmful effects. In contrast, the conventional intrabody DNAs can be integrated into the genome in a stable manner or at least expressed persistently, which can lead to uncontrollable events. The great advantage compared with administration of monoclonal antibodies in vivo is furthermore that with the use of an antibody-coding (modified) RNA as described here, no antibodies have to be prepared and purified in an involved manner and they are therefore considerably less expensive to prepare. The most essential advantage of the present invention is, however, that intracellularly expressed proteins can also be achieved with the antibodies coded by (modified) RNAs according to the invention, which is not possible with monoclonal antibodies known hitherto from the prior art.

The following figures and examples are intended to explain in more detail and illustrate the above description, without being limited thereto.

FIGURES

FIG. 1 illustrates the structure of an IgG antibody. IgG antibodies are built up from in each case two identical light and two heavy protein chains which are bonded to one another via disulfide bridges. The light chain comprises the N-terminal variable domain $V_L$ and the C-terminal constant domain $C_L$. The heavy chain of an IgG antibody can be divided into an N-terminal variable domain $V_H$ and three constant domains $C_H1$, $C_H2$ and $C_H3$.

FIG. 2 shows the gene cluster for the light and the heavy chains of an antibody:
(A): Gene cluster for the light chain κ.
(B): Gene cluster for the light chain λ.
(C): and (D): Gene cluster for the heavy chain.
In this context, the variable region of a heavy chain is composed of three different gene segments. In addition to the V and J segments, additional D segments are also found here. The $V_H$, $D_H$ and $J_H$ segments can likewise be combined with one another virtually as desired to form the variable region of the heavy chain.

Figure 1:
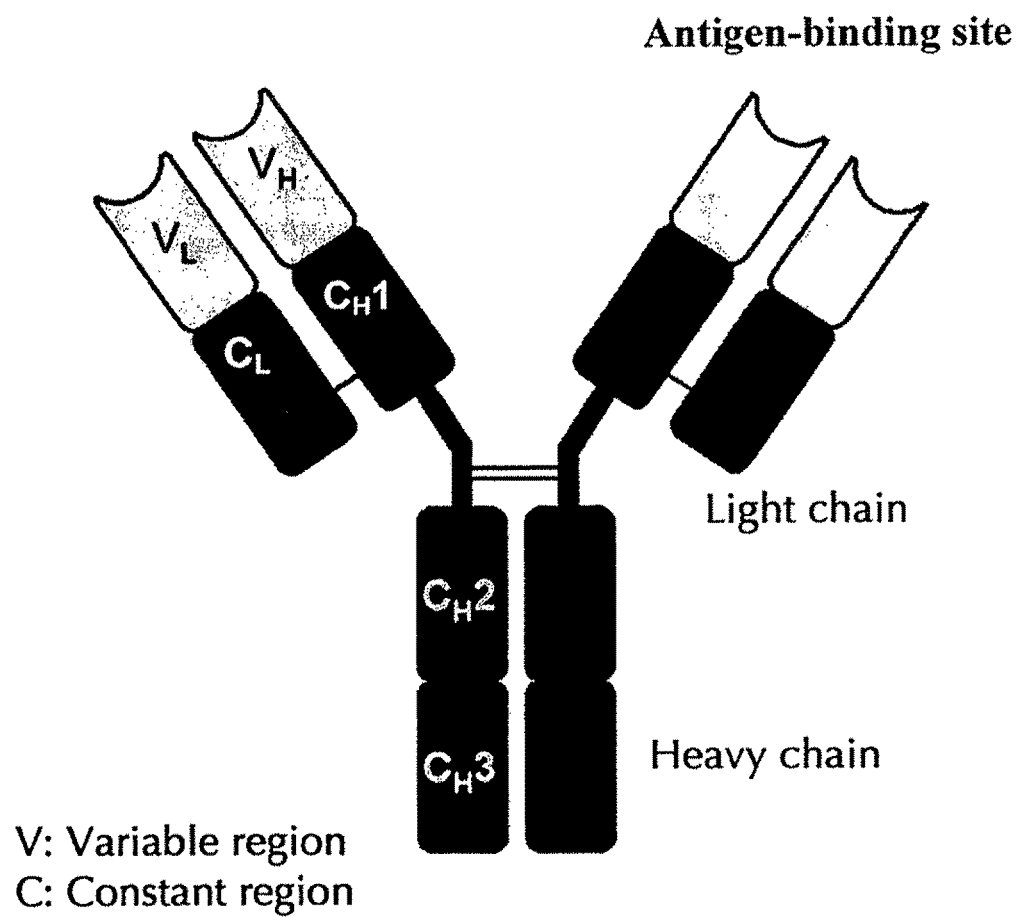
Figure 2:
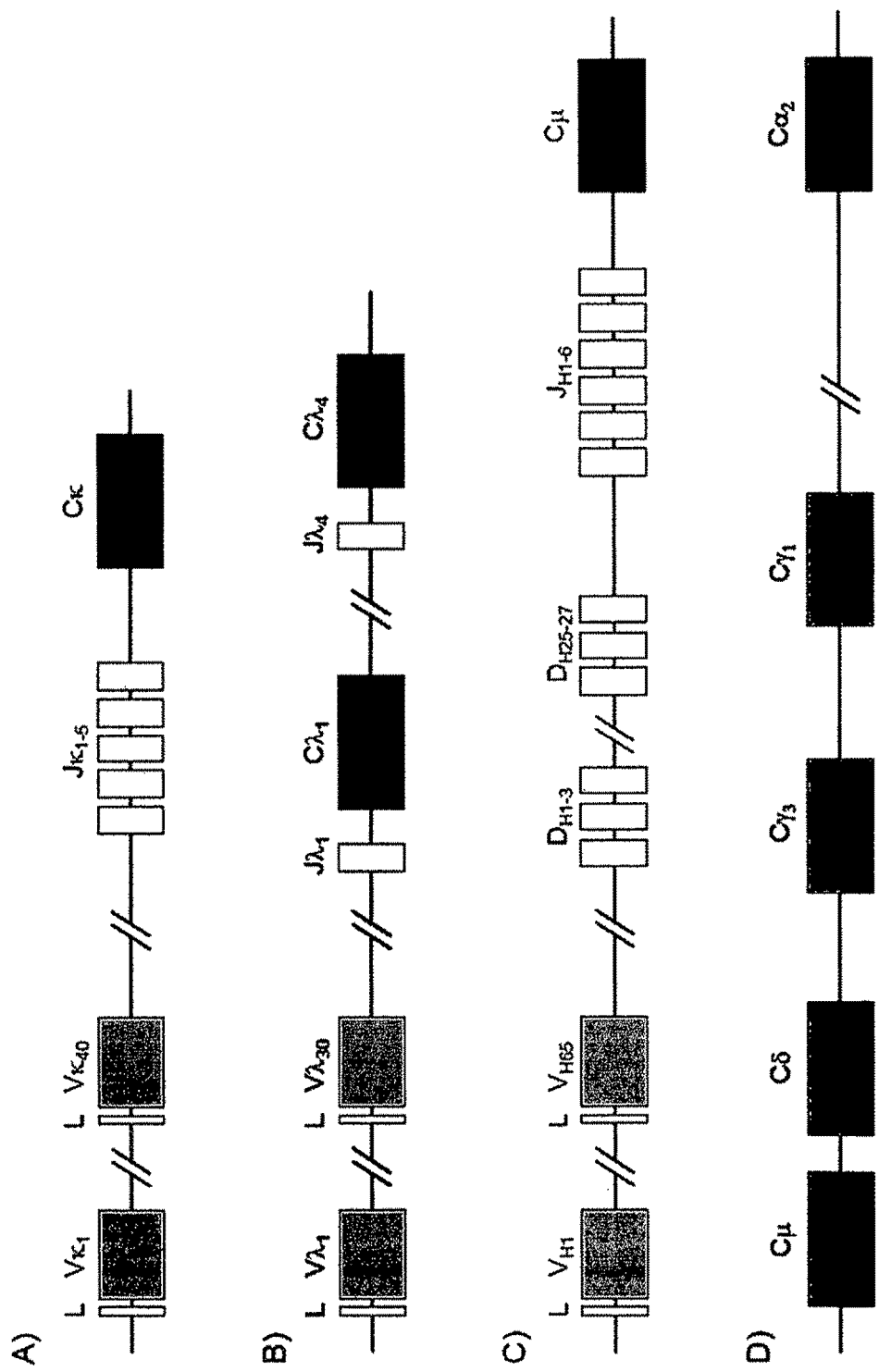
Figure 3:
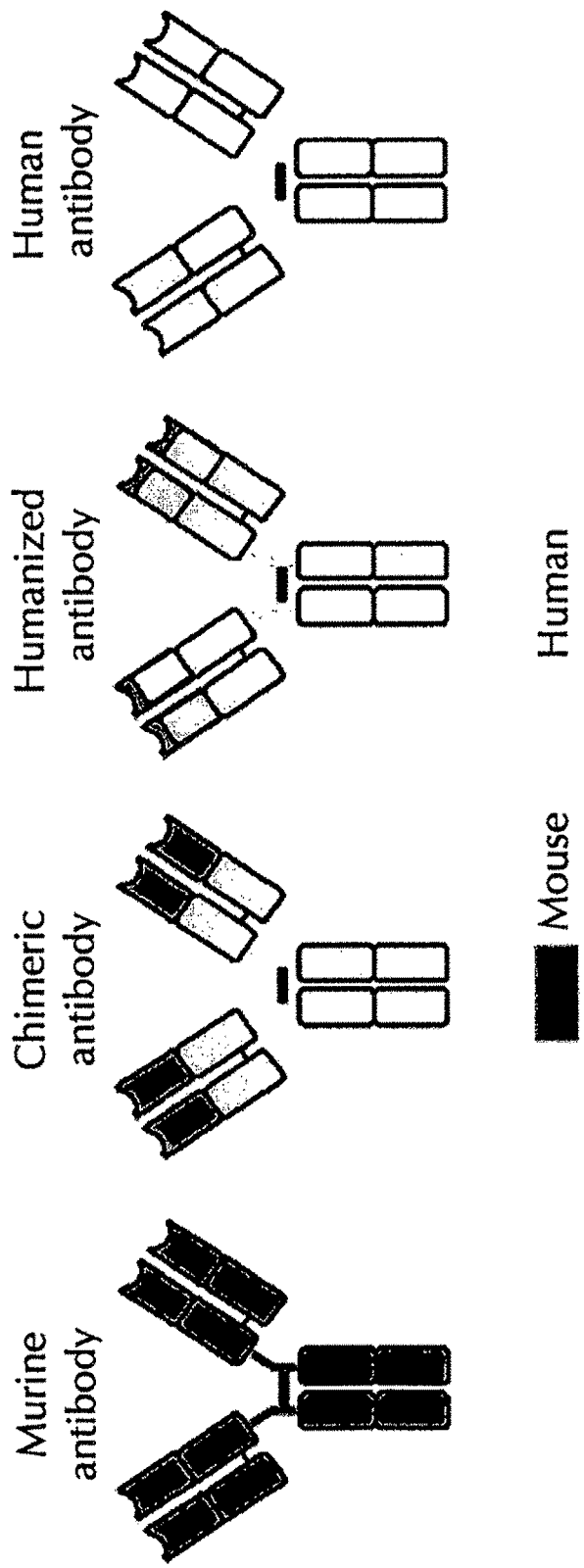
FIG. 3 illustrates in the form of a diagram the differences in the light and heavy chains of murine (i.e. obtained in the mouse host organism), chimeric, humanized and human antibodies.
Figure 4:
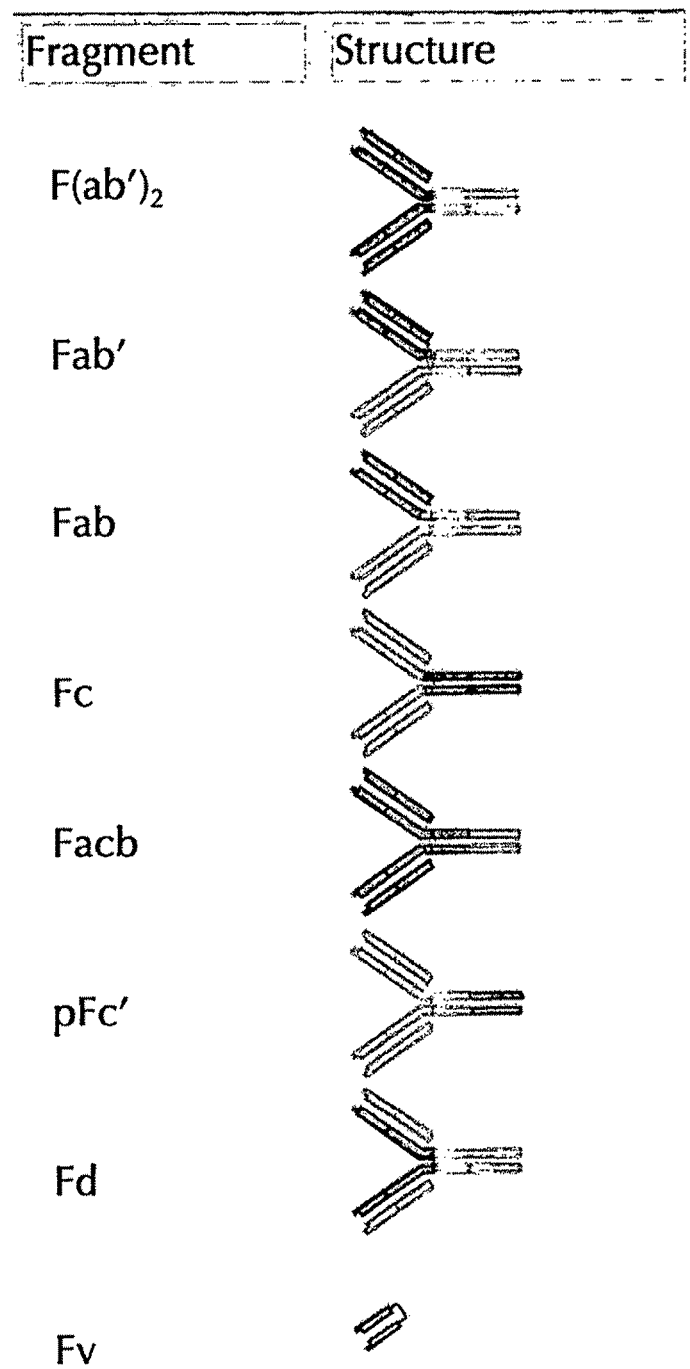
FIG. 4 shows an overview of the structure of various antibody fragments. The constituents of the antibody fragments are shown on a dark grey background.
Figure 5:
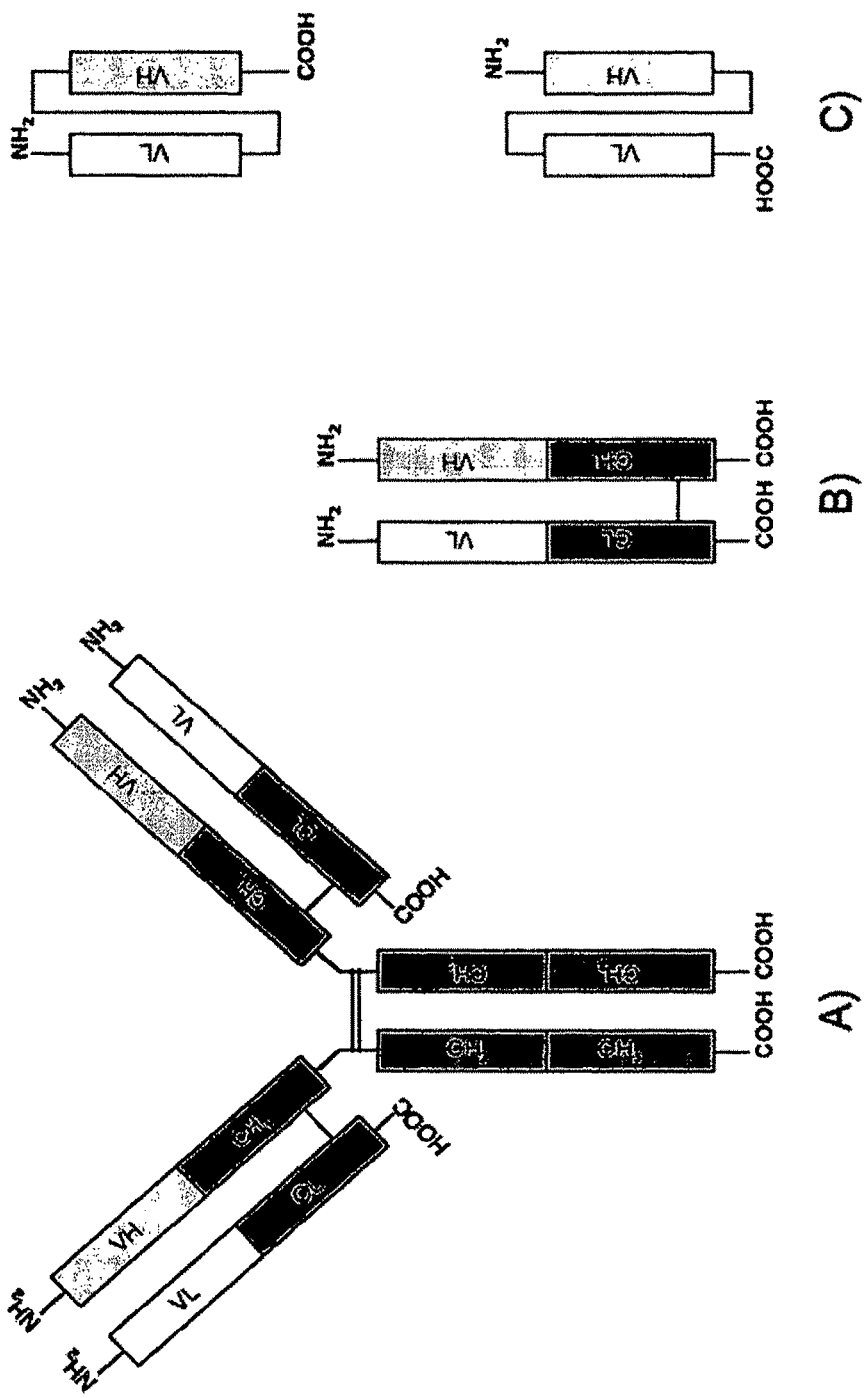

FIG. 5 shows various variants of antibodies and antibody fragments in FIGS. 5A, 5B and 5C:
(A) shows a diagram of an IgG antibody of two light and two heavy chains.
(B) shows an Fab fragments from the variable and a constant domain in each case of a light and a heavy chain. The two chains are bonded to one another via a disulfide bridge.
(C) shows an scFv fragment from the variable domain of the light and the heavy chain, which are bonded to one another via an artificial polypeptide linker.

Figure 6:
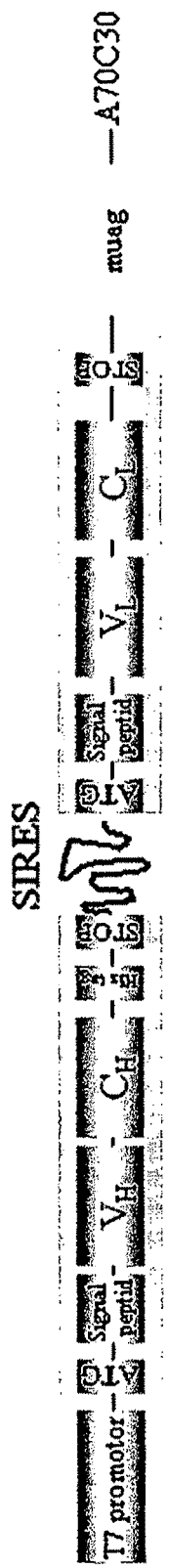

FIG. 6 shows a presentation of an antibody-coding (modified) RNA according to the invention as an expression construct. In this:

$V_H$=variable domain of the heavy chain;
$C_H$=constant domain of the heavy chain;
$V_L$=variable domain of the light chain;
$C_L$=constant domain of the light chain;
SIRES=internal ribosomal entry site (IRES, superIRES)
muag=mutated form of the 3' UTR of the alpha-globin gene; and
A70C30=polyA-polyC tail.

Figure 7:
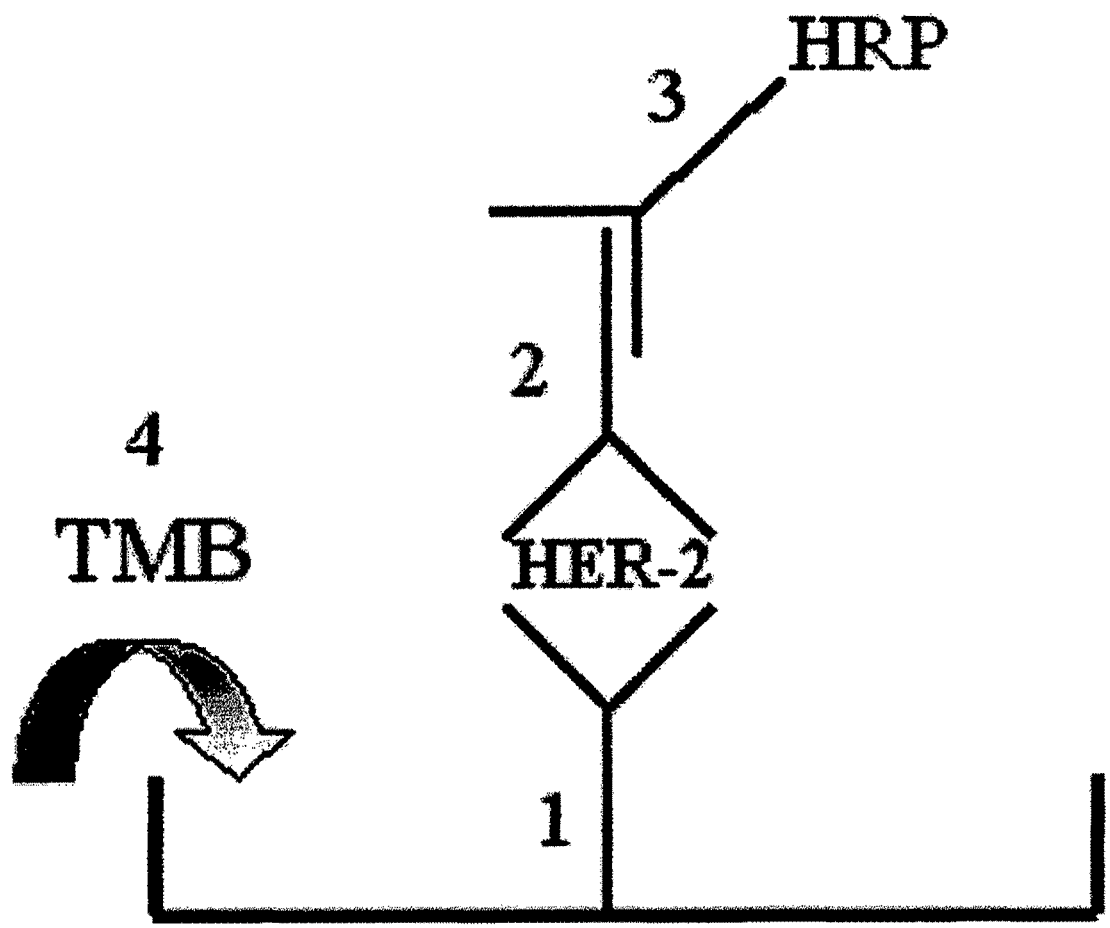

FIG. 7 shows a diagram of the detection of an antibody coded by an RNA according to the invention by means of ELISA on the example of the antigen Her2.

FIG. 8 shows the wild-type DNA sequence of the heavy chain of the antibody rituximab (=Rituxan, MabThera) (wild-type: GC content: 56.5%, length: 1,344) (SEQ ID NO: 1).

FIG. 9 shows the GC-optimized DNA sequence of the heavy chain of the antibody rituximab (=Rituxan, MabThera) (GC content: 65.9%, length: 1,344) (SEQ ID NO: 2).

FIG. 10 shows the wild-type DNA sequence of the light chain of the antibody rituximab (=Rituxan, MabThera) (wild-type: GC content: 58.5%, length: 633) (SEQ ID NO: 3).

FIG. 11 shows the GC-optimized DNA sequence of the light chain of the antibody rituximab (=Rituxan, MabThera) (GC content: 67.2%, length: 633) (SEQ ID NO: 4).

FIG. 12 shows the total construct of the GC-optimized DNA sequence of the antibody rituximab (=Rituxan, MabThera) with the light and heavy chains (SEQ ID NO: 5). The total construct contains the following sequences and cleavage sites (see also alternative cleavage sites of FIG. 25, SEQ ID No. 51):

```
ACC linker for an optimum Kozak sequence
AAGCTT HindIII
TGA stop codon
ACTAGT SpeI
AGATCT BglII
ATGCAT NsiI
CATCATCATCATCATCAT (SEQ ID NO: 60) His tag Signal peptide, HLA-A*0201: GC-rich
ATGGCCGTGATGGCGCCGCGGACCCTGGTCCTCCTGCTGAGCGGCGCCCT

CGCCCTGACGCAGACCTGGGCCGGG (SEQ ID NO: 61).
```

The coding region of the heavy chain sequence starts with the signal peptide as given above (italic). This region is G/C enriched as well. The subsequent sequence starting with CAG represents the actual antibody coding sequence (see FIG. 9) for the heavy chain, which ends with AAG and is followed by the above described His tag sequence. Finally, the open reading frame for the heavy chain ends with the stop codon TGA ( ___ ) The coding region for the light chain sequence starts 3' upstream with the signal peptide's ATG as given above followed by the light chain's coding region for the light chain starting with CAG running to the stop codon TGA ( ___ ) (see FIG. 11). Both coding regions for the light and the heavy chain are separated by an IRES element (......) The inventive RNA coded by the construct given in FIG. 12 may or may not contain a (His) tag sequence and may contain a signal peptide sequence different from the above peptide sequence or may even have no signal peptide sequence. Accordingly, the inventive RNA molecule contains preferably the coding region (with or without a signal peptide sequence at its beginning) of the heavy and/or the light chain (e.g. as shown in FIG. 12), preferably in combination with at least one ribosomal entry site.

FIG. 13 shows the wild-type DNA sequence of the heavy chain of the antibody cetuximab (=Erbitux) (wild-type: GC content: 56.8%, length: 1,359) (SEQ ID NO: 6).

FIG. 14 shows the GC-optimized DNA sequence of the heavy chain of the antibody cetuximab (=Erbitux) (GC content: 65.9%, length: 1,359) (SEQ ID NO: 7).

FIG. 15 shows the wild-type DNA sequence of the light chain of the antibody cetuximab (=Erbitux) (wild-type: GC content: 58.2%, length: 642) (SEQ ID NO: 8).

FIG. 16 shows the GC-optimized DNA sequence of the light chain of the antibody cetuximab (=Erbitux) (GC content: 65.7%, length: 642) (SEQ ID NO: 9).

FIG. 17 shows the total construct of the GC-optimized DNA sequence of the antibody cetuximab (=Erbitux) with the light and heavy chains (SEQ ID NO: 10). The total construct contains the following sequences and cleavage sites (see also alternative cleavage sites of FIG. 26, SEQ ID No 52):

```
ACC linker for an optimum Kozak sequence
AAGCTT HindIII
TGA stop codon
ACTAGT SpeI
AGATCT BglII
ATGCAT NsiI
CATCATCATCATCATCAT (SEQ ID NO: 60) His tag Signal peptide, HLA-A*0201: GC-rich
ATGGCCGTGATGGCGCCGCGGACCCTGGTCCTCCTGCTGAGCGGCGCCCT

CGCCCTGACGCAGACCTGGGCCGGG (SEQ ID NO: 61).
```

The coding region of the heavy chain sequence starts with the signal peptide as given above (italic). This region is G/C enriched as well. The subsequent sequence starting with CAG represents the actual antibody coding sequence (see FIG. 14) for the heavy chain, which ends with AAG and is followed by the above described His tag sequence. Finally, the open reading frame for the heavy chain ends with the stop codon TGA ( ___ ) The coding region for the light chain sequence starts 3' upstream with the signal peptide's ATG as given above followed by the light chain's coding region for the light chain starting with GAC running to the stop codon TGA ( ___ ) (see FIG. 16). Both coding regions for the light and the heavy chain are separated by an IRES element (......) The inventive RNA coded by the construct given in FIG. 17 may or may not contain a (His) tag sequence and may contain a signal peptide sequence different from the above peptide sequence or may even have no signal peptide sequence. Accordingly, the inventive RNA molecule contains preferably the coding region (with or without a signal peptide sequence at its beginning) of the heavy and/or the light chain (e.g. as shown in FIG. 17), preferably in combination with at least one ribosomal entry site.

FIG. 18 shows the wild-type DNA sequence of the heavy chain of the antibody trastuzumab (=Herceptin) (wild-type: GC content: 57.8%, length: 1,356) (SEQ ID NO: 11).

FIG. 19 shows the GC-optimized DNA sequence of the heavy chain of the antibody trastuzumab (=Herceptin) (GC content: 67.0%, length: 1,356) (SEQ ID NO: 12).

FIG. 20 shows the wild-type DNA sequence of the light chain of the antibody trastuzumab (=Herceptin) (wild-type: GC content: 56.9%, length: 645) (SEQ ID NO: 13).

FIG. 21 shows the GC-optimized DNA sequence of the light chain of the antibody trastuzumab (=Herceptin) (GC content: 66.4%, length: 645) (SEQ ID NO: 14).

FIG. 22 shows the total construct of the GC-optimized DNA sequence of the antibody trastuzumab (=Herceptin) with the light and heavy chains (SEQ ID NO: 15). The total construct contains the following sequences and cleavage sites (see also alternative cleavage sites of FIG. 27, SEQ ID No. 53):

ACC linker for an optimum Kozak sequence
AAGCTT HindIII
TGA stop codon
ACTAGT SpeI
AGATCT BglII
ATGCAT NsiI
CATCATCATCATCATCAT (SEQ ID NO: 60) His tag Signal peptide, HLA-A*0201: GC-rich
ATGGCCGTGATGGCGCCGCGGACCCTGGTCCTCCTGCTGAGCGGCGCCC
TCGCCCTGACGCAGACCTGGGCCGGG (SEQ ID NO: 61).

The coding region of the heavy chain sequence starts with the signal peptide as given above (italic). This region is G/C enriched as well. The subsequent sequence starting with GAG represents the actual antibody coding sequence (see FIG. 19) for the heavy chain, which ends with AAG and is followed by the above described His tag sequence. Finally, the open reading frame for the heavy chain ends with the stop codon TGA (_) The coding region for the light chain sequence starts 3' upstream with the signal peptide's ATG as given above followed by the light chain's coding region for the light chain starting with GAC running to the stop codon TGA (_) (see FIG. 21). Both coding regions for the light and the heavy chain are separated by an IRES element ( . . . ) The inventive RNA coded by the construct given in FIG. 22 may or may not contain a (His) tag sequence and may contain a signal peptide sequence different from the above peptide sequence or may even have no signal peptide sequence. Accordingly, the inventive RNA molecule contains preferably the coding region (with or without a signal peptide sequence at its beginning) of the heavy and/or the light chain (e.g. as shown in FIG. 22), preferably in combination with at least one ribosomal entry site.

Figure 23:
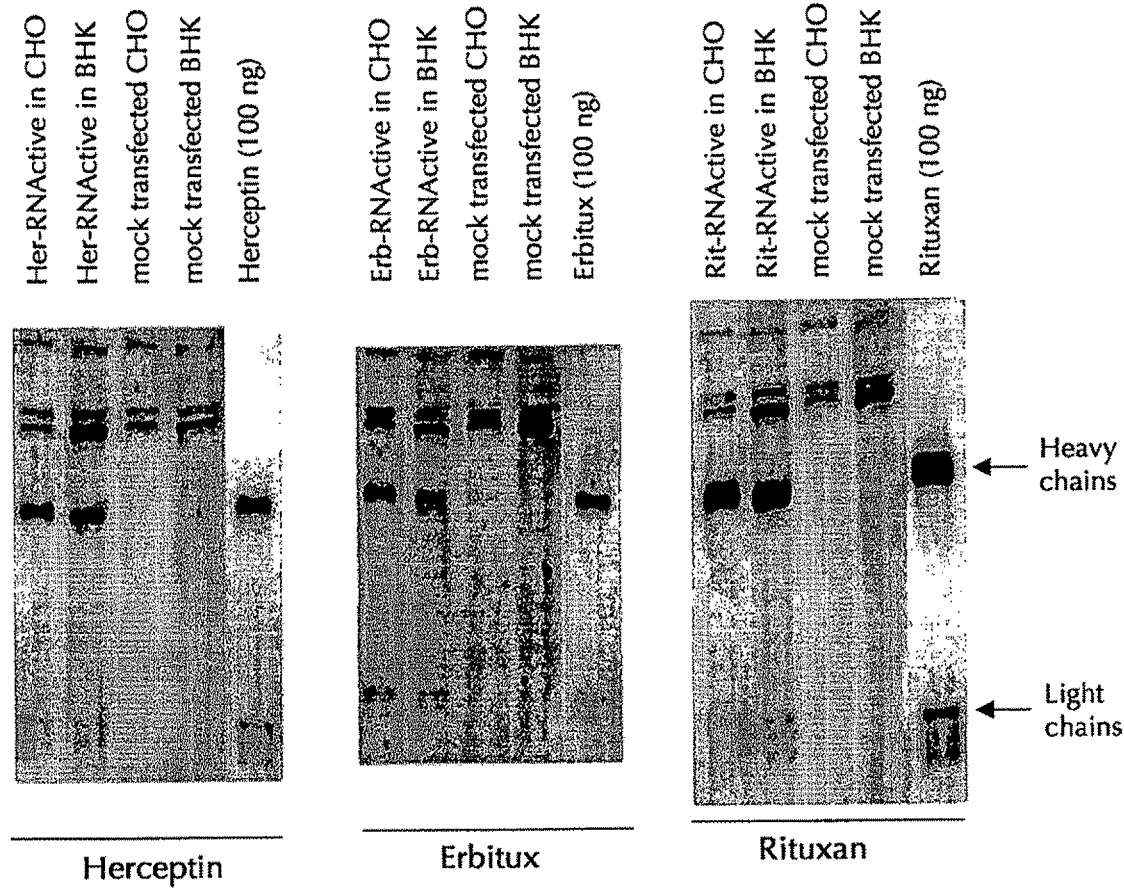

FIG. 23 shows RNA-mediated antibody expression in cell culture. CHO or BHK cells were transfected with 20 µg of antibody-encoding mRNA according to the invention which was produced (RNA, G/C enriched, see above) or mock-transfected. 24 hours after transfection protein synthesis was analysed by Western blotting of cell lysates. Cells harboured about 0.5 µg of protein as assessed by Western Blot analysis. Each lane represents 10% of total lysate. Humanised antibodies served as control and for a rough estimate of protein levels. The detection antibody recognises both heavy and light chains; moreover, it shows some unspecific staining with cell lysates (three distinct bands migrating much slower than those of the antibodies). A comparison with control antibodies clearly demonstrates that heavy and light chains were produced in equal amounts.

Figure 24:
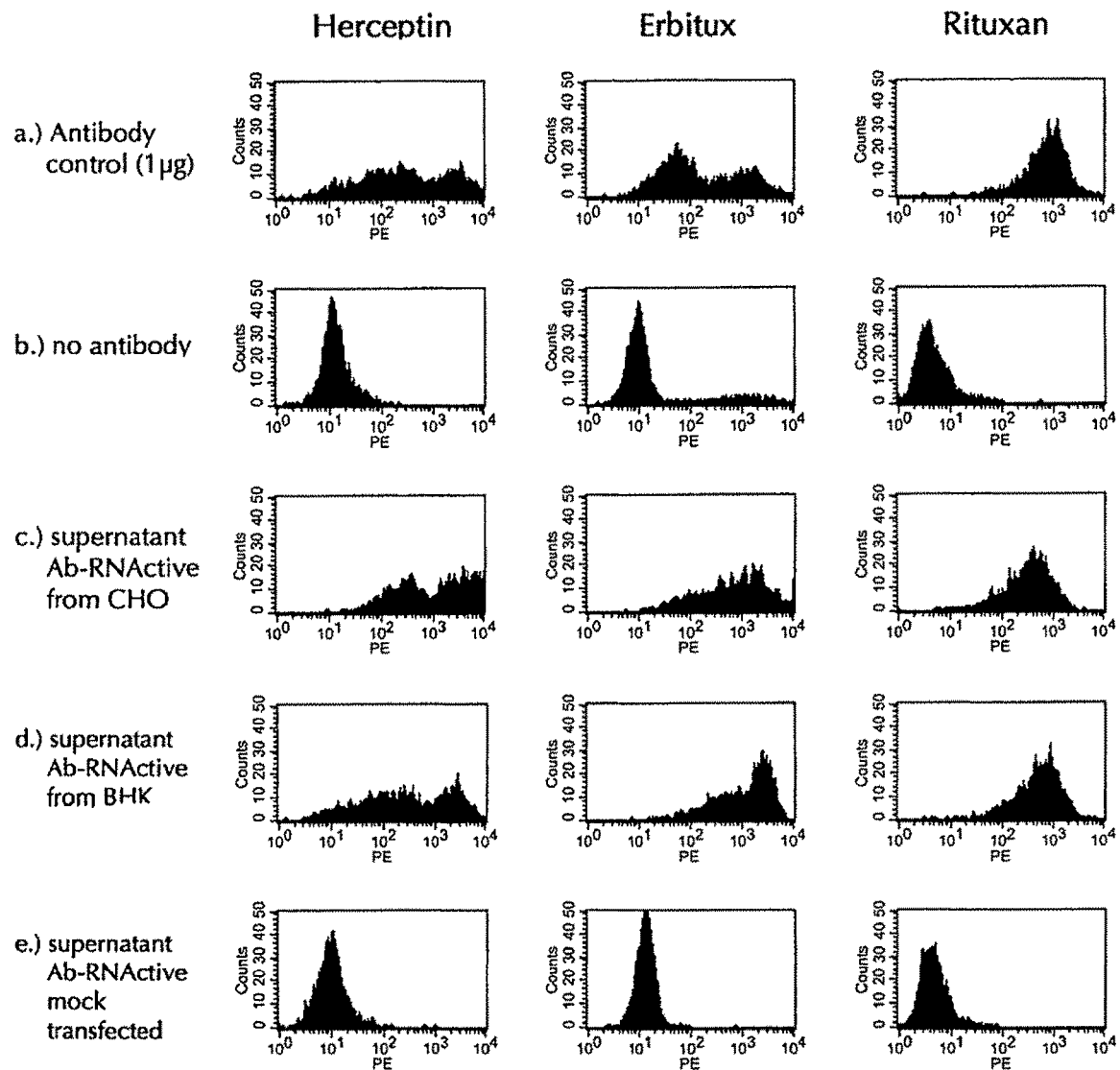

FIG. 24 shows that RNA-mediated antibody expression gives rise to a functional protein (antibody). Functional antibody formation was addressed by FACS staining of antigen-expressing target cells. In order to examine the production of functional antibodies, cell culture supernatants of RNA-transfected (20 µg of Ab-RNA as defined above in Example 1) cells were collected after 48 to 96 hours. About 8% of total supernatant was used to stain target cells expressing the respective antigen. Humanised antibodies served as control and for a rough estimate of protein levels. Primary antibody used for cell staining: a) humanised antibody; b) none; c,d) supernatant from RNA-transfected cells expressing the respective antibody; e) supernatant from mock-transfected CHO cells. Calculations on the basis of the analysis shown in FIG. 24 reveal that cells secreted more than 12-15 µg of functional antibody within 48-96 hours. Accordingly, the present invention proves that RNA encoding antibodies may enter into cell, may be expressed within the cell and considerable amounts of RNA encoded antibodies are then secreted by the cell into the surrounding medium/extracellular space. Cell transfection in vivo or in vitro by the inventive RNA may therefore be used to provide antibodies acting e.g. therapeutically in the extracellular space.

FIG. 25 shows an alternative sequence of the construct of FIG. 12 (antibody rituximab), wherein the restriction sites have been modified as compared to SEQ ID No. 5 of FIG. 12 (SEQ ID No.: 51). For closer information with regard to the description of various sequence elements it is referred to FIG. 12.

FIG. 26 shows an alternative sequence of the construct of FIG. 17 (antibody cetuximab), wherein the restriction sites have been modified as compared to SEQ ID No. 10 of FIG. 17 (SEQ ID No.: 52). For closer information with regard to the description of various sequence elements it is referred to FIG. 17.

FIG. 27 shows an alternative sequence of the construct of FIG. 22 (antibody trastuzumab), wherein the restriction sites have been modified as compared to SEQ ID No. 15 of FIG. 22 (SEQ ID No.: 53). For closer information with regard to the description of various sequence elements it is referred to FIG. 22.

The following examples explain the present invention in more detail, without limiting it.

EXAMPLES

1. Example 1.1 Cell Lines and Cell Culture Conditions Used:

The cell lines HeLa (human cervix carcinoma cell line; Her2-positive), HEK293 (human embryonal kidney; Her2-negative) and BHK21 (Syrian hamster kidney; Her2-negative) were obtained from the DMSZ (Deutsche Sammlung von Mikroorganismen and Zellkulturen GmbH) in Braunschweig and cultured in RPMI medium enriched with 2 mM L-glutamine (Bio Whittaker) and 10 µg/ml streptomycin and 10 µml of penicillin at 37° C. under 5% $CO_2$.

1.2 Preparation of Expression Vectors for Modified RNA Sequences According to the Invention:

For the production of modified RNA sequences according to the invention, the GC-enriched and translation-optimized DNA sequences which code for a heavy chain and a light chain of an antibody (e.g. cetuximab (ERBITUX®), trastuzumab (HERCEPTIN®) and rituximab (RITUXAN®), cf. SEQ ID NO: 1-15, where SEQ ID NO: 1, 3, 6, 8, 11 and 13 represent the particular coding sequences which are not GC-optimized of the heavy and the light chains of these antibodies and SEQ ID NO: 2, 4, 5, 7, 9, 10, 12, 14 and 15 represent the coding GC-enriched sequences (see above)) were cloned into the pCV19 vector (Cure Vac GmbH) by standard molecular biology methods. To ensure equimolar expression of the two chains, an IRES (internal ribosomal entry site) was introduced. The mutated 3' UTR (untranslated region) of the alpha-globin gene and a polyA-polyC tail at the 3' end serve for additional stabilizing of the mRNA. The signal peptide of the HLA-A*0201 gene is coded for secretion of the antibody expressed. A His tag was additionally introduced for detection of the antibody. FIG. 6 shows the expression constructs used.

1.3 Preparation of the G/C-Enriched and Translation-Optimized Antibody-Coding mRNA An in vitro transcription was carried out by means of T7 polymerase (T7-Opti mRNA Kit, CureVac, Tubingen, Germany), followed by purification with Pure Messenger™ (CureVac, Tubingen, Germany). For this, a DNase digestion was first carried out, followed by an LiCl precipitation and thereafter an HPLC using a porous reverse phase as the stationary phase (PURE Messenger).

1.4 Detection of RNA-Antibody by Means of Flow Cytometry:

1 million cells were transfected with the mRNA according to one of SEQ ID NO: 5, 10 or 15 (see above), which codes for an antibody as described above, by means of electroporation and were then cultured in the medium for 16 h. The antibody expressed was detected by means of an FITC-coupled His tag antibody. Alternatively, the secreted antibody from the supernatant of transfected cells was added to non-transfected, antigen-expressing cells and, after incubation, detected by the same method.

1.5 In Vitro Detection of an Antibody Coded by an RNA according to the Invention by Means of ELISA:

A microtitre plate was loaded with a murine antibody (1) against a first antigen (HER-2). Cell lysate of antigen-expressing cells was then added to the plate. The antigen was bound here by the murine antigen-specific antibody (1). The supernatant of cells which were transfected with a modified mRNA according to the invention which codes for an HER-2-specific antibody was then added to the microtitre plate. The HER-2-specific antibody (2) contained in the supernatant likewise binds to the antibody-bound antigen, the two antibodies recognizing different domains of the antigen. For detection of the bound antibody (2), anti-human IgG coupled to horseradish peroxidase (3-HRP) was added, the substrate TMB being converted and the result determined photometrically.

1.6 In Vivo Detection of an Antibody Coded by an RNA according to the Invention:

An antibody-coding (m)RNA according to the invention as described above was injected intradermally or intramuscularly into BALB/c mice. 24 h thereafter, the corresponding tissues were removed and protein extracts were prepared. The expression of the antibody was detected by means of ELISA as described here.

1.7 Detection of an Antibody Coded by an RNA according to the Invention by Means of Western Blotting:

The expressed antibodies from the supernatant of cells which were transfected with a modified mRNA which codes for an antibody as described above were separated by means of a polyacrylamide gel electrophoresis and then transferred to a membrane. After incubation with anti-His tag antibody and a second antibody coupled to horseradish peroxidase, the antibody expressed was detected by means of chemoluminescence.

1.8 Tumour Model:

SKOV-3 cells were injected subcutaneously into BALB/c mice. Within the following 28 days, eight portions of 10 µg of a modified mRNA which codes for an antibody as described above were injected into the tail vein of the mice. The tumour growth was monitored over a period of 5 weeks.

2. Example 2.1. Cell Lines

RNA-based expression of humanised antibodies was done in either CHO-K1 or BHK-21 cells. The tumour cell lines BT-474, A-431 and Raji strongly expressing HER2, EGFR and CD20, respectively, were used to record antibody levels. All cell lines except CHO were maintained in RPMI supplemented with FCS and glutamine according to the supplier's information. CHO cells were grown in Ham's F12 supplemented with 10% FCS. All cell lines were obtained from the German collection of cell cultures (DSMZ).

2.2. Antibody Expression

Various amounts of antibody-RNA (G/C enriched as defined by FIGS. 12, 17, 22, 25, 26, 27) encoding the humanised antibodies Herceptin, Erbitux, and Rituxan, respectively, (see the description given above for Example 1) were transfected into either CHO or BHK cells by electroporation. Conditions were as follows: 300 V, 450 µF for CHO and 300 V, 150 µF for BHK. After transfection, cells were seeded onto 24-well cell culture plates at a density of 2-400.000 cells per well. For collection of secreted protein, medium was replaced by 250 µl of fresh medium after cell attachment to the plastic surface. Secreted protein was collected for 24-96 hours and stored at 4° C. In addition, cells were harvested into 50 µl of phosphate buffered saline containing 0.5% BSA and broken up by three freeze-thaw cycles. Cell lysates were cleared by centrifugation and stored at −80° C.

2.3. Western Blot Analysis

In order to detect translation of transfected RNA, proteins from either cell culture supernatants or cell lysates were separated by a 12% SDS-PAGE and blotted onto a nitrocellulose membrane. Humanised antibodies Herceptin (Roche), Erbitux (Merck KGAA), and Mabthera=Rituxan (Roche) were used as controls. After blotting was completed, membranes were consecutively incubated with biotinylated goat anti-human IgG (Dianova), streptavidin coupled to horseradish peroxidase (BD), and a chemiluminescent substrate (SuperSignal West Pico, Pierce). Staining was detected with a Fuji LAS-1000 chemiluminescence camera.

2.4. FACS Analysis 200.000 target cells expressing the respective antigen were incubated with either control antibodies (Herceptin, Erbitux, Mabthera) or cell culture supernatants. For detection of bound antibodies, cells were stained with biotinylated goat anti-human IgG (Dianova) and PE-labelled streptavidin (Invitrogen). Cells were analysed on a FACSCalibur (BD).

The invention claimed is:

1. A composition comprising isolated purified single-stranded linear mRNAs encoding an antibody, comprising RNA sequences encoding:
   (i) a first polypeptide comprising the variable domain of the antibody heavy chain (VH), linked to a heterologous secretory signal coding sequence; and
   (ii) a second polypeptide comprising the variable domain of the antibody light chain (VL), linked to a heterologous secretory signal coding sequence,
   wherein the mRNA has been purified by reverse phase chromatography, and wherein the composition is pharmaceutically acceptable.

2. The composition according to claim 1, wherein the antibody is a humanized antibody or a bispecific antibody.

3. The composition according to claim 1, wherein the mRNA is modified, wherein the modification is a sequence modification compared to a wild type mRNA that encodes the antibody.

4. The composition according to claim 3, wherein the mRNA has a G/C content in the coding region which is greater than the G/C content of the coding region of the wild type mRNA sequence, the coded amino acid sequence being unchanged with respect to the native mRNA.

5. The composition according to claim 3, wherein the coding region of the mRNA is modified compared with the coding region of the wild type mRNA such that at least one codon of the wild type mRNA which codes for a tRNA which is relatively rare in the cell is exchanged for a codon which codes for a tRNA which is relatively frequent in the cell and which carries the same amino acid as the relatively rare tRNA.

6. The composition according to claim 1, wherein the mRNA includes at least one base-modified nucleotide chosen from the group consisting of 2-amino-6-chloropurine riboside 5'-triphosphate, 2-aminoadenosine 5'-triphosphate, 2-thiocytidine 5'-triphosphate, 2-thiouridine 5'-triphosphate, 4-thiouridine 5'-triphosphate, 5-aminoallylcytidine 5'-triphosphate, 5-aminoallyluridine 5'-triphosphate, 5-bromocytidine 5'-triphosphate, 5-bromouridine 5'-triphosphate, 5-iodocytidine 5'-triphosphate, 5-iodouridine 5'-triphosphate, 5-methylcytidine 5'-triphosphate, 5-methyluridine 5'triphosphate, 6-azacytidine 5'-triphosphate, 6-azauridine 5'-triphosphate, 6-chloropurine riboside 5'-triphosphate, 7-deazaadenosine 5'-triphosphate, 7-deazaguanosine 5'-triphosphate, 8-azaadenosine 5'-triphosphate, 8-azidoadenosine 5'-triphosphate, benzimidazole riboside 5'-triphosphate, N1-methyladenosine 5'-triphosphate, N1-methylguanosine 5'-triphosphate, N6-methyladenosine 5'-triphosphate, 06-methylguanosine 5'-triphosphate, pseudouridine 5'-triphosphate, puromycin 5'-triphosphate and xanthosine 5'-triphosphate.

7. The composition according to claim 6, wherein the base-modified nucleotides are chosen from the group consisting of 5-methylcytidine 5'-triphosphate and pseudouridine 5'-triphosphate.

8. The composition according to claim 1, wherein the mRNA additionally has a 5' cap structure chosen from the group consisting of m7G(5')ppp (5'(A,G(5')ppp(5')A and G(5')ppp(5')G.

9. The composition according to claim 1, wherein the mRNA additionally has a poly-A tail of 10 to 200 adenosine nucleotides (SEQ ID NO: 62).

10. The composition according to claim 1, wherein the mRNA additionally has a poly-C tail of 10 to 200 cytosine nucleotides (SEQ ID NO: 54).

11. The composition according to claim 1, wherein the mRNA additionally codes a tag for purification chosen from the group consisting of a polyhistidine tag (HIS tag), a hexahistidine tag (SEQ ID NO: 59), a streptavidin tag (Strep tag), an SBP tag (streptavidin-binding tag), a GST (glutathione S-transferase) tag, a Myc tag, a Swa11 epitope, a FLAG tag and an HA tag.

12. The composition according to claim 3, wherein the modified mRNA comprises sequences encoding the antibody codes for the heavy chains according to SEQ ID NO: 12 and the light chains according to SEQ ID NO: 14.

13. The composition according to claim 1, wherein the mRNA comprises a coding sequence according to SEQ ID NO: 15.

14. The composition according to claim 3, wherein the mRNA comprises a sequence at least 90% identical to the sequence SEQ ID NO: 15 over the total length of the nucleic acid sequence of SEQ ID NO: 15.

15. The composition according to claim 1, wherein the sequences encoding the VH and VL polypeptides are encoded on the same mRNA molecule and are separated by an internal ribosomal entry site (IRES).

16. The composition according to claim 15, wherein the mRNA comprises a poly-A sequence of 10 to 200 adenosine nucleotides and a poly-C sequence of 10 to 200 cytosine nucleotides.

17. The composition according to claim 1, wherein the VH and VL polypeptides comprise the variable domains of Trastuzumab, wherein the antibody binds to HER-2/neu.

18. The composition according to claim 17, wherein:
 (i) sequences encoding the VH and VL polypeptides are encoded on the same mRNA molecule and are separated by an internal ribosomal entry site (IRES); and
 (ii) the mRNA comprises a poly-A sequence of 10 to 200 adenosine nucleotides and a poly-C sequence of 10 to 200 cytosine nucleotides.

19. The composition according to claim 1, wherein the mRNA is modified, wherein the modification is a modification chosen from modifications of the nucleotide compared with a wild type mRNA by introduction of a non-native nucleotide and/or a chemically modified nucleotide.

20. The composition of claim 1, wherein the chromatography is over a porous stationary phase comprising non-alkylated polystyrene-divinylbenzene.

21. The composition according to claim 1, wherein the RNA has been additionally purified by affinity chromatography or gel filtration.

22. The composition according to claim 1, wherein, when expressed in a cell, the composition induces production of a CD-20 binding antibody.

23. The composition according to claim 1, wherein the composition comprises a mRNA encoding:
 (i) a first polypeptide comprising the variable domain heavy chain (VH) of a CD20-binding antibody; and
 (ii) a second polypeptide comprising the variable domain light chain (VL) of a CD20-binding antibody.

24. The composition according to claim 7, wherein the antibody is a bispecific antibody.

25. The composition according to claim 24, wherein the antibody binds to CD40.

26. The composition according to claim 7, wherein the antibody binds to CD40.

27. The composition according to claim 24, wherein the antibody binds to CD3.

28. The composition according to claim 7, wherein the antibody binds to CD3.

29. The composition according to claim 19, wherein the mRNA has a lipid modification.

30. The composition according to claim 19, wherein the mRNA contains on at least one nucleotide of the RNA a modification of a nucleotide, wherein the nucleotides are chosen from 1-methyl-adenine, 2-methyl-adenine, 2-methylthio-N-6-isopentenyl-adenine, N6-methyl-adenine, N6-isopentenyl-adenine, 2-thio-cytosine, 3-methylcytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, dihydrouracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5-methoxycarbonylmethyl-uracil, 5-methoxy-uracil, uracil-5-oxyacetic acid methyl ester, uracil-5-oxyacetic acid (v), pseudouracil, 1-methyl-pseudouracil, queosine, β-D-mannosyl-queosine, wybutoxosine, phosphoramidates, phosphorothioates, peptide nucleotides, methylphosphonates, 7-deazaguanosine, 5-methylcytosine and inosine.

31. The composition of claim 30, wherein the modified nucleotide is 1-methyl-pseudouracil.

* * * * *

UNITED STATES PATENT AND TRADEMARK OFFICE
CERTIFICATE OF CORRECTION

PATENT NO. : 11,421,038 B2
APPLICATION NO. : 12/522214
DATED : August 23, 2022
INVENTOR(S) : Hoerr et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 453 days.

Signed and Sealed this
Eleventh Day of February, 2025

Coke Morgan Stewart
*Acting Director of the United States Patent and Trademark Office*

SEQUENCE LISTING

<160> NUMBER OF SEQ ID NOS: 62

<210> SEQ ID NO 1
<211> LENGTH: 1344
<212> TYPE: DNA

<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody Rituximab - wildtype, heavy chain

<400> SEQUENCE: 1

```
caggcgtatc tgcagcagag cggcgcggaa ctggtgcgcc cgggcgcgag cgtgaaaatg      60
agctgcaaag cgagcggcta cctttacc agctataaca tgcattgggt gaaacagacc      120
ccgcgccagg gcctggaatg gattggcgcg atttatccgg caacggcga taccagctat      180
aaccagaaat ttaaaggcaa agcgaccctg accgtggata aagcagcag caccgcgtat      240
atgcagctga gcagcctgac cagcgaagat agcgcggtgt attttgcgc gcgcgtggtg      300
tattatagca acagctattg gtattttgat gtgtggggca ccggcaccac cgtgaccgtg      360
agcggcccga gcgtgtttcc gctggcgccg agcagcaaaa gcaccagcgg cggcaccgcg      420
gcgctgggct gcctggtgaa agattatttt ccggaaccgg tgaccgtgag ctggaacagc      480
ggcgcgctga ccagcggcgt gcataccttt ccggcggtgc tgcagagcag cggcctgtat      540
agcctgagca gcgtggtgac cgtgccgagc agcagcctgg cacccagac ctatatttgc      600
aacgtgaacc ataaaccgag caacaccaaa gtggataaaa agcggaacc gaaaagctgc      660
gataaaccc atcctgccc gccgtgcccg cgccggaac tgctgggcgg cccgagcgtg      720
tttctgtttc cgccgaaacc gaaagatacc ctgatgatta gccgcacccc ggaagtgacc      780
tgcgtggtgg tggatgtgag ccatgaagat ccggaagtga atttaactg gtatgtggat      840
ggcgtggaag tgcataacgc gaaaaccaaa ccgcgcgaag aacagtataa cagcacctat      900
cgcgtggtga gcgtgctgac cgtgctgcat caggattggc tgaacggcaa agaatataaa      960
tgcaaagtga gcaacaaagc gctgccggcg ccgattgaaa aaaccattag caaagcgaaa      1020
ggccagccgc gcgaaccgca ggtgtatacc ctgccgccga ccgcgatga actgaccaaa      1080
aaccaggtga gcctgacctg cctggtgaaa ggcttttatc cgagcgatat tgcggtggaa      1140
tgggaaagca acggccagcc ggaaaacaac tataaaaacca ccccgccggt gctggatagc      1200
gatggcagct ttttcctgta tagcaaactg accgtggata aagccgctg cagcaggggc      1260
aacgtgttta gctgcagcgt gatgcatgaa gcgctgcata ccattatac ccagaaaagc      1320
ctgagcctga gcccgggcaa ataa                                            1344
```

<210> SEQ ID NO 2
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody Rituximab - GC-optimized heavy chain

<400> SEQUENCE: 2

```
caggcctacc tgcagcagag cggcgcggag ctcgtgcggc cgggggcctc ggtcaagatg      60
agctgcaagg ccagcggcta caccttcacg agctacaaca tgcactgggt gaagcagacc      120
ccgcgccagg gctggagtg atcggcgcc atctaccccg ggaacggcga caccagctac      180
aaccagaagt tcaagggcaa ggcgaccctg acggtggaca gtcgagcag caccgcctac      240
atgcagctca gcagcctgac ctcggaggac agcgccgtct acttctgcgc ccgggtggtg      300
tactacagca acagctactg gtacttcgac gtctggggga ccggcacgac cgtgaccgtg      360
```

```
agcgggccca gcgtcttccc cctggccccc tcgagcaaga gcaccagcgg cggcacggcg      420
gccctcgggt gcctggtgaa ggactacttc cccgagcccg tgaccgtcag ctggaactcg      480
ggcgccctga ccagcggggt gcacaccttc ccggccgtgc tccagagcag cggcctgtac      540
agcctgagct cggtcgtgac ggtgcccagc agcagcctcg ggacccagac ctacatctgc      600
aacgtcaacc acaagcccag caacaccaag gtggacaaga aggcggagcc caagtcgtgc      660
gacaagacgc acacctgccc gccctgcccc gccccgagc tgctgggcgg cccgagcgtg       720
ttcctcttcc cgcccaagcc caaggacacc ctgatgatca gccgcacccc cgaggtcacg      780
tgcgtggtgg tcgacgtgag ccacgaggac cccgaggtga agttcaactg gtacgtcgac      840
ggggtggagg tgcacaacgc caagaccaag ccccggagg agcagtacaa cagcacctac       900
cgcgtcgtga gcgtgctgac cgtcctccac caggactggc tgaacggcaa ggagtacaag      960
tgcaaggtgt cgaacaaggc cctgccggcc cccatcgaga agacgatcag caaggcgaag     1020
gggcagcccc gggagcccca ggtgtacacc ctcccgccca gcgcgacga gctgaccaag      1080 aaccaggtca gcctgacctg cctcgtgaag ggcttctacc ccagcgacat cgccgtggag     1140
tgggagtcga acgggcagcc cgagaacaac tacaagacga cccgcccgt cctggacagc      1200 gacggcagct tcttcctgta cagcaagctc accgtggaca agagccggtg gcagcagggc     1260
aacgtgttca gctgctcggt catgcacgag gccctgcaca accactacac ccagaagagc     1320
ctgagcctca gccccgggaa gtga                                             1344

<210> SEQ ID NO 3
<211> LENGTH: 633
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody Rituximab - wildtype, light chain

<400> SEQUENCE: 3
cagattgtgc tgagccagag cccggcgatt ctgagcgcga gccgggcga aaaagtgacc       60 atgacctgcc gcgcgagcag cagcgtgagc tatatgcatt ggtatcagca gaaaccgggc     120
agcagcccga aaccgtggat ttatgcgccg agcaacctgg cgagcggcgt gccggcgcgc     180
tttagcggca gcggcagcgg caccagctat agcctgacca ttagccgcgt ggaagcggaa     240
gatgcggcga cctattattg ccagcagtgg agctttaacc cgccgacctt tggcgcgggc     300
accaaactgg aactgaaacg caccgtggcg gcgccgagcg tgtttatttt tccgccgagc     360
gatgaacagc tgaaaagcgg caccgcgagc gtggtgtgcc tgctgaacaa ctttatccg      420 cgcgaagcga agtgcagtg gaaagtggat aacgcgctgc agagcggcaa cagccaggaa     480
agcgtgaccg aacaggatag caaagatagc acctatagcc tgagcagcac cctgaccctg     540
agcaaagcgg attatgaaaa acataaagtg tatgcgtgcg aagtgaccca tcagggcctg     600
agcagcccgg tgaccaaaag ctttaaccgc taa                                   633

<210> SEQ ID NO 4
<211> LENGTH: 633
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
```

<223> OTHER INFORMATION: Antibody Rituximab - GC-optimized light chain

<400> SEQUENCE: 4

| | | | | | |
|---|---|---|---|---|---|
| cagatcgtgc | tgagccagtc | gccggccatc | ctcagcgcga | gccccggcga | aaggtcacc | 60 |
| atgacgtgcc | gggccagcag | ctcggtgagc | tacatgcact | ggtaccagca | gaagcccggg | 120 |
| agcagcccca | agccgtggat | ctacgccccc | agcaacctgg | cctcgggcgt | gcccgcgcgc | 180 |
| ttcagcggga | gcggcagcgg | gaccagctac | agcctgacca | tctcgcgggt | cgaggccgag | 240 |
| gacgccgcca | cctactactg | ccagcagtgg | agcttcaacc | cgcccacgtt | cggcgccggc | 300 |
| accaagctcg | agctgaagcg | caccgtggcg | gcccccagcg | tgttcatctt | cccgcccagc | 360 |
| gacgagcagc | tgaagagcgg | gaccgcctcg | gtcgtgtgcc | tcctgaacaa | cttctacccc | 420 |
| cgggaggcca | aggtgcagtg | gaaggtcgac | aacgcgctgc | agagcggcaa | cagccaggag | 480 |
| agcgtgacgg | agcaggacag | caaggacagc | acctactcgc | tcagcagcac | cctgaccctg | 540 |
| agcaaggccg | actacgagaa | gcacaaggtg | tacgcctgcg | aggtcacgca | ccaggggctc | 600 |
| agctcgcccg | tgaccaagag | cttcaaccgc | tga | | | 633 |

<210> SEQ ID NO 5
<211> LENGTH: 2269
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Antibody Rituximab - modified RNA for the light and heavy chains in the total construct

<400> SEQUENCE: 5

| | | | | | |
|---|---|---|---|---|---|
| aagcttacca | tggccgtgat | ggcgccgcgg | accctggtcc | tcctgctgag | cggcgccctc | 60 |
| gccctgacgc | agacctgggc | cgggcaggcc | tacctgcagc | agagcggcgc | ggagctcgtg | 120 |
| cggccggggg | cctcggtcaa | gatgagctgc | aaggccagcg | gctacacctt | cacgagctac | 180 |
| aacatgcact | gggtgaagca | gaccccgcgc | caggggctgg | agtggatcgg | cgccatctac | 240 |
| cccgggaacg | gcgacaccag | ctacaaccag | aagttcaagg | gcaaggcgac | cctgacggtg | 300 |
| gacaagtcga | gcagcaccgc | ctacatgcag | ctcagcagcc | tgacctcgga | ggacagcgcc | 360 |
| gtctacttct | gcgcccgggt | ggtgtactac | agcaacagct | actggtactt | cgacgtctgg | 420 |
| ggaccggca | cgaccgtgac | cgtgagcggg | cccagcgtct | tcccctggc | ccctcgagc | 480 |
| aagagcacca | gcggcggcac | ggcggccctc | gggtgcctgg | tgaaggacta | cttccccgag | 540 |
| cccgtgaccg | tcagctggaa | ctcgggcgcc | ctgaccagcg | gggtgcacac | cttcccggcc | 600 |
| gtgctccaga | gcagcggcct | gtacagcctg | agctcggtcg | tgacggtgcc | cagcagcagc | 660 |
| ctcgggaccc | agacctacat | ctgcaacgtc | aaccacaagc | ccagcaacac | caaggtggac | 720 |
| aagaaggcgg | agcccaagtc | gtgcgacaag | acgcacacct | gcccgccctg | ccccgccccc | 780 |
| gagctgctgg | gcgcccgag | cgtgttcctc | ttcccgccca | gcccaaggga | caccctgatg | 840 |
| atcagccgca | ccccgaggt | cacgtgcgtg | gtggtcgacg | tgagccacga | ggaccccgag | 900 |
| gtgaagttca | actggtacgt | cgacggggtg | gaggtgcaca | acgccaagac | caagcccggg | 960 |
| gaggagcagt | acaacagcac | ctaccgcgtc | gtgagcgtgc | tgaccgtcct | ccaccaggac | 1020 |
| tggctgaacg | gcaaggagta | caagtgcaag | gtgtcgaaca | aggccctgcc | ggcccccatc | 1080 |
| gagaagacga | tcagcaaggc | gaaggggcag | ccccgggagc | cccaggtgta | caccctcccg | 1140 |
| cccagccgcg | acgagctgac | caagaaccag | gtcagcctga | cctgcctcgt | gaagggcttc | 1200 |

```
taccccagcg acatcgccgt ggagtgggag tcgaacgggc agcccgagaa caactacaag    1260
acgaccccgc ccgtcctgga cagcgacggc agcttcttcc tgtacagcaa gctcaccgtg    1320
gacaagagcc ggtggcagca gggcaacgtg ttcagctgct cggtcatgca cgaggccctg    1380
cacaaccact acacccagaa gagcctgagc ctcagccccg gaagcatca tcatcatcat    1440 cattgaccag atctttctga catttctgac atttctgaca tttctgacat ttctgacatt    1500
tctgacattt ctgacatttc tgacatttct gacatttctg acatatgcat accatggccg    1560
tgatggcgcc gcggaccctg gtcctcctgc tgagcggcgc cctcgccctg acgcagacct    1620
gggccgggca gatcgtgctg agccagtcgc cggccatcct cagcgcgagc cccggcgaga    1680
aggtcaccat gacgtgccgg gccagcagct cggtgagcta catgcactgg taccagcaga    1740
agcccgggag cagccccaag ccgtggatct acgcccccag caacctggcc tcgggcgtgc    1800
ccgcgcgctt cagcgggagc ggcagcggga ccagctacag cctgaccatc tcgcgggtcg    1860
aggccgagga cgccgccacc tactactgcc agcagtggag cttcaacccg ccacgttcg    1920 gcgccggcac caagctcgag ctgaagcgca ccgtggcggc ccccagcgtg ttcatcttcc    1980
cgcccagcga cgagcagctg aagagcggaa ccgcctcggt cgtgtgcctc ctgaacaact    2040
tctacccccg ggaggccaag gtgcagtgga aggtcgacaa cgcgctgcag agcggcaaca    2100
gccaggagag cgtgacggag caggacagca aggacagcac ctactcgctc agcagcaccc    2160
tgaccctgag caaggccgac tacgagaagc acaaggtgta cgcctgcgag gtcacgcacc    2220 agggggctcag ctcgcccgtg accaagagct caaccgctg accactagt              2269

<210> SEQ ID NO 6
<211> LENGTH: 1359
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody Cetuximab (= Erbitux) - wildtype,
      heavy chain

<400> SEQUENCE: 6
caggtgcagc tgaaacagag cggcccgggc ctggtgcagc cgagccagag cctgagcatt     60
acctgcaccg tgagcggctt tagcctgacc aactatggcg tgcattgggt cgcgcagagc    120
ccgggcaaag gcctggaatg gctgggcgtg atttggagcg gcggcaacac cgattataac    180
accccgttta ccagccgcct gagcattaac aaagataaca gcaaaagcca ggtgttttt    240 aaaatgaaca gcctgcagag caacgatacc gcgatttatt attgcgcgcg cgcgctgacc    300
tattatgatt atgaatttgc gtattgggc cagggcaccc tggtgaccgt gagcgcggcg    360
agcaccaaag gcccgagcgt gtttccgctg gcgccgagca gcaaaagcac cagcggcggc    420
accgcggcgc tgggctgcct ggtgaaagat tattttccgg aaccggtgac cgtgagctgg    480
aacagcggcg cgctgaccag cggcgtgcat accttccgg cggtgctgca gagcagcggc    540
ctgtatagcc tgagcagcgt ggtgaccgtg ccgagcagca gcctgggcac ccagacctat    600
atttgcaacg tgaaccataa accgagcaac accaaagtgg ataaacgcgt ggaaccgaaa    660
agcccgaaaa gctgcgataa aacccatacc tgcccgccgt gccgggcgcc ggaactgctg    720 ggcgcccga gcgtgtttct gtttccgccg aaaccgaaag ataccctgat gattagccgc    780
accccggaag tgacctgcgt ggtggtggat gtgagccatg aagatccgga agtgaaattt    840
```

| | |
|---|---:|
| aactggtatg tggatggcgt ggaagtgcat aacgcgaaaa ccaaaccgcg cgaagaacag | 900 |
| tataacagca cctatcgcgt ggtgagcgtg ctgaccgtgc tgcatcagga ttggctgaac | 960 |
| ggcaaagaat ataaatgcaa agtgagcaac aaagcgctgc cggcgccgat tgaaaaaacc | 1020 |
| attagcaaag cgaaaggcca gccgcgcgaa ccgcaggtgt ataccctgcc gccgagccgc | 1080 |
| gatgaactga ccaaaaacca ggtgagcctg acctgcctgg tgaaaggctt ttatccgagc | 1140 |
| gatattgcgg tggaatggga aagcaacggc cagccggaaa acaactataa aaccaccccg | 1200 |
| ccggtgctgg atagcgatgg cagcttttt ctgtatagca aactgaccgt ggataaaagc | 1260 |
| cgctggcagc agggcaacgt gtttagctgc agcgtgatgc atgaagcgct gcataaccat | 1320 |
| tatacccaga aaagcctgag cctgagcccg ggcaaataa | 1359 |

<210> SEQ ID NO 7
<211> LENGTH: 1359
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody Cetuximab (= Erbitux) - GC-optimized
      heavy chain

<400> SEQUENCE: 7

| | |
|---|---:|
| caggtgcagc tgaagcagag cggcccgggg ctcgtccagc cctcgcagag cctgagcatc | 60 |
| acctgcacgg tgagcggctt cagcctgacc aactacgggg tgcactgggt ccggcagtcg | 120 |
| cccggcaagg gctcgagtg gctgggcgtg atctggagcg gcgggaacac cgactacaac | 180 |
| acccccttca cgagccgcct gagcatcaac aaggacaaca gcaagtcgca ggtgttcttc | 240 |
| aagatgaaca gcctccagag caacgacacc gccatctact actgcgcgcg ggccctgacc | 300 |
| tactacgact acgagttcgc ctactggggc caggggaccc tggtcacggt gagcgccgcg | 360 |
| agcaccaagg gcccgagcgt gttccccctc gcccccctcga gcaagagcac cagcggcggg | 420 |
| accgccgccc tgggctgcct ggtcaaggac tacttccccg agccggtgac ggtgagctgg | 480 |
| aactcggggg ccctcaccag cggcgtccac accttccccg cggtgctgca gagcagcggg | 540 |
| ctgtacagcc tcagctcggt ggtcaccgtg cccagcagca gcctgggcac gcagacctac | 600 |
| atctgcaacg tgaaccacaa gcccagcaac accaaggtcg acaagcgcgt ggagccgaag | 660 |
| tcgcccaaga gctgcgacaa gacccacacg tgcccgccct gccccgcccc cgagctgctc | 720 |
| ggcgggccca gcgtgttcct gttcccgccc aagcccaagg acaccctgat gatcagccgg | 780 |
| acccccgagg tcacctgcgt ggtggtcgac gtgagccacg aggacccgga ggtgaagttc | 840 |
| aactggtacg tcgacggcgt ggaggtgcac aacgccaaga cgaagcccg cgaggagcag | 900 |
| tacaacagca cctaccgggt cgtgtcggtg ctcaccgtcc tgcaccagga ctggctgaac | 960 |
| gggaaggagt acaagtgcaa ggtgagcaac aaggccctcc ccgcgcccat cgagaagacc | 1020 |
| atcagcaagg ccaagggcca gccgcgcgag ccccaggtgt acacgctgcc cccagccgg | 1080 |
| gacgagctga ccaagaacca ggtcagcctc acctgcctgg tgaaggggtt ctacccgtcg | 1140 |
| gacatcgccg tggagtggga gagcaacggc cagcccgaga caactacaa gaccacgccc | 1200 |
| ccggtcctgg acagcgacgg cagcttcttc ctctacagca agctgaccgt ggacaagagc | 1260 |
| cgctggcagc aggggaacgt gttctcgtgc agcgtcatgc acgaggccct gcacaaccac | 1320 |
| tacacccaga agagcctcag cctgagcccc ggcaagtga | 1359 |

<210> SEQ ID NO 8
<211> LENGTH: 642
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Antibody Cetuximab (= Erbitux) - wildtype,
light chain

<400> SEQUENCE: 8

```
gatattctgc tgacccagag cccggtgatt ctgagcgtga gcccgggcga acgcgtgagc      60
tttagctgcc gcgcgagcca gagcattggc accaacattc attggtatca gcagcgcacc     120
aacggcagcc cgcgcctgct gattaaatat gcgagcgaaa gcattagcgg cattccgagc     180
cgctttagcg gcagcggcag cggcaccgat tttaccctga gcattaacag cgtggaaagc     240
gaagatattg cggattatta ttgccagcag aacaacaact ggccgaccac ctttggcgcg     300
ggcaccaaac tggaactgaa acgcaccgtg gcggcgccga gcgtgtttat ttttccgccg     360
agcgatgaac agctgaaaag cggcaccgcg agcgtggtgt gcctgctgaa caactttat      420 ccgcgcgaag cgaaagtgca gtggaaagtg gataacgcgc tgcagagcgg caacagccag     480
gaaagcgtga ccgaacagga tagcaaagat agcacctata gcctgagcag caccctgacc     540
ctgagcaaag cggattatga aaaacataaa gtgtatgcgt gcgaagtgac ccatcagggc     600
ctgagcagcc cggtgaccaa aagctttaac cgcggcgcgt aa                        642
```

<210> SEQ ID NO 9
<211> LENGTH: 642
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Antibody Cetuximab (= Erbitux) - GC-optimized
light chain

<400> SEQUENCE: 9

```
gacatcctgc tcacccagag cccggtgatc ctgtcggtca gccccggcga gcgggtgagc      60
ttcagctgcc gcgccagcca gtcgatcggg acgaacatcc actggtacca gcagcggacc     120
aacggcagcc ccgcgctgct catcaagtac gcgagcgaga gcatcagcgg gatcccctcg     180
cggttcagcg gcagcgggag cggcaccgac ttcaccctga gcatcaacag cgtggagtcg     240
gaggacatcg ccgactacta ctgccagcag aacaacaact ggccgacgac cttcggcgcc     300
gggaccaagc tggagctcaa gcgcaccgtc gccgcgccca gcgtgttcat cttcccgccc     360
agcgacgagc agctgaagag cggcacggcc agcgtggtct gcctgctcaa caacttctac     420
ccccgggagg ccaaggtgca gtggaaggtg gacaacgccc tgcagtcggg gaacagccag     480
gagagcgtca ccgagcagga cagcaaggac agcacctaca gcctgtcgag caccctcacg     540
ctgagcaagg ccgactacga gaagcacaag gtgtacgcgt gcgaggtgac ccaccagggc     600
ctgagcagcc ccgtcaccaa gtcgttcaac cgcggcgcct ga                        642
```

<210> SEQ ID NO 10
<211> LENGTH: 2293
<212> TYPE: DNA
<213> ORGANISM: Artificial Sequence
<220> FEATURE:
<223> OTHER INFORMATION: Description of Artificial Sequence: Synthetic
polynucleotide <220> FEATURE:
<223> OTHER INFORMATION: Antibody Cetuximab (= Erbitux) - total construct with GC-optimized heavy and light chains

<400> SEQUENCE: 10

| | | | | | |
|---|---|---|---|---|---|
| aagcttacca | tggccgtgat | ggcgccgcgg | accctggtcc | tcctgctgag | cggcgccctc | 60 |
| gccctgacgc | agacctgggc | cgggcaggtg | cagctgaagc | agagcggccc | ggggctcgtc | 120 |
| cagccctcgc | agagcctgag | catcacctgc | acggtgagcg | gcttcagcct | gaccaactac | 180 |
| ggggtgcact | gggtccggca | gtcgcccggc | aaggggctcg | agtggctggg | cgtgatctgg | 240 |
| agcggcggga | acaccgacta | caacaccccc | ttcacgagcc | gcctgagcat | caacaaggac | 300 |
| aacagcaagt | cgcaggtgtt | cttcaagatg | aacagcctcc | agagcaacga | caccgccatc | 360 |
| tactactgcg | cgcgggccct | gacctactac | gactacgagt | tcgcctactg | gggccagggg | 420 |
| accctggtca | cggtgagcgc | cgcgagcacc | aagggcccga | gcgtgttccc | cctcgccccc | 480 |
| tcgagcaaga | gcaccagcgg | cgggaccgcc | gccctgggct | gcctggtcaa | ggactacttc | 540 |
| cccgagccgg | tgacggtgag | ctggaactcg | ggggccctca | ccagcggcgt | ccacaccttc | 600 |
| cccgcggtgc | tgcagagcag | cgggctgtac | agcctcagct | cggtggtcac | cgtgcccagc | 660 |
| agcagcctgg | gcacgcagac | ctacatctgc | aacgtgaacc | acaagcccag | caacaccaag | 720 |
| gtcgacaagc | gcgtggagcc | gaagtcgccc | aagagctgcg | acaagaccca | cacgtgcccg | 780 |
| ccctgccccg | cccccgagct | gctcggcggg | ccagcgtgt | tcctgttccc | gcccaagccc | 840 |
| aaggacaccc | tgatgatcag | ccggaccccc | gaggtcacct | gcgtggtggt | cgacgtgagc | 900 |
| cacgaggacc | cggaggtgaa | gttcaactgg | tacgtcgacg | gcgtggaggt | gcacaacgcc | 960 |
| aagacgaagc | ccgcgagga | gcagtacaac | agcacctacc | gggtcgtgtc | ggtgctcacc | 1020 |
| gtcctgcacc | aggactggct | gaacgggaag | gagtacaagt | gcaaggtgag | caacaaggcc | 1080 |
| ctccccgcgc | ccatcgagaa | gaccatcagc | aaggcaagg | gccagccgcg | cgagccccag | 1140 |
| gtgtacacgc | tgcccccag | ccgggacgag | ctgaccaaga | accaggtcag | cctcacctgc | 1200 |
| ctggtgaagg | ggttctaccc | gtcggacatc | gccgtggagt | gggagagcaa | cggccagccc | 1260 |
| gagaacaact | acaagaccac | gccccgggtc | ctggacagcg | acggcagctt | cttcctctac | 1320 |
| agcaagctga | ccgtggacaa | gagccgctgg | cagcagggga | acgtgttctc | gtgcagcgtc | 1380 |
| atgcacgagg | ccctgcacaa | ccactacacc | cagaagagcc | tcagcctgag | ccccggcaag | 1440 |
| catcatcatc | atcatcattg | accagatctt | tctgacattt | ctgacatttc | tgacatttct | 1500 |
| gacatttctg | acatttctga | catttctgac | atttctgaca | tttctgacat | ttctgacata | 1560 |
| tgcataccat | ggccgtgatg | gcgccgcgga | ccctggtcct | cctgctgagc | ggcgccctcg | 1620 |
| ccctgacgca | gacctgggcc | ggggacatcc | tgctcaccca | gagcccggtg | atcctgtcgg | 1680 |
| tcagccccgg | cgagcgggtg | agcttcagct | gccgcgccag | ccagtcgatc | gggacgaaca | 1740 |
| tccactggta | ccagcagcgg | accaacggca | gcccccgcct | gctcatcaag | tacgcgagcg | 1800 |
| agagcatcag | cgggatcccc | tcgcggttca | gcggcagcgg | gagcggcacc | gacttcaccc | 1860 |
| tgagcatcaa | cagcgtggag | tcggaggaca | tcgccgacta | ctactgccag | cagaacaaca | 1920 |
| actggccgac | gaccttcggc | gccgggacca | agctggagct | caagcgcacc | gtcgccgcgc | 1980 |
| ccagcgtgtt | catcttcccg | cccagcgacg | agcagctgaa | gagcggcacg | gccagcgtgg | 2040 |
| tctgcctgct | caacaacttc | tacccccggg | aggccaaggt | gcagtggaag | gtggacaacg | 2100 |
| ccctgcagtc | ggggaacagc | caggagagcg | tcaccgagca | ggacagcaag | gacagcacct | 2160 |
| acagcctgtc | gagcaccctc | acgctgagca | aggccgacta | cgagaagcac | aaggtgtacg | 2220 |

```
cgtgcgaggt gacccaccag ggcctgagca gccccgtcac caagtcgttc aaccgcggcg    2280
cctgaccact agt                                                       2293
```

<210> SEQ ID NO 11
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody Trastuzumab (= Herceptin) - wildtype,
      heavy chain

<400> SEQUENCE: 11

```
gaagtgcagc tggtggaaag cggcggcggc ctggtgcagc cgggcggcag cctgcgcctg      60
agctgcgcgg cgagcggctt taacattaaa gataccctata ttcattgggt gcgccaggcg    120
ccgggcaaag cctggaatg gtggcgcgc atttatccga ccaacggcta tacccgctat      180
gcggatagcg tgaaaggccg ctttaccatt agcgcggata ccagcaaaaa caccgcgtat    240
ctgcagatga acagcctgcg cgcggaagat accgcggtgt attattgcag ccgctggggc    300
ggcgatggct tttatgcgat ggattattgg ggccaggca cctggtgac cgtgagcagc      360 gcgagcacca aaggcccgag cgtgtttccg ctggcgccga gcagcaaaag caccagcggc    420
ggcaccgcgg cgctgggctg cctggtgaaa gattattttc cggaaccggt gaccgtgagc    480
tggaacagcg gcgcgctgac cagcggcgtg cataccttc cggcggtgct gcagagcagc    540
ggcctgtata gcctgagcag cgtggtgacc gtgccgagca gcagcctggg cacccagacc    600
tatatttgca acgtgaacca taaaccgagc aacaccaaag tggataaaaa agtggaaccg    660
ccgaaaagct gcgataaaac ccatacctgc ccgccgtgcc cggcgccgga actgctgggc    720
ggcccgagcg tgtttctgtt ccgccgaaa ccgaaagata ccctgatgat tagccgcacc    780
ccggaagtga cctgcgtggt ggtggatgtg agccatgaag atccggaagt gaaatttaac    840
tggtatgtgg atggcgtgga agtgcataac gcgaaaacca accgcgcga agaacagtat    900 aacagcacct atcgcgtggt gagcgtgctg accgtgctgc atcaggattg gctgaacggc    960
aaagaatata atgcaaagt gagcaacaaa gcgctgccgg cgccgattga aaaaccatt    1020 agcaaagcga aggccagcc gcgcgaaccg caggtgtata ccctgccgcc gagccgcgat   1080
gaactgacca aaaaccaggt gagcctgacc tgcctggtga aaggcttta tccgagcgat   1140 attgcggtgg aatgggaaag caacggccag ccggaaaaca actataaaac cacccccgcc   1200
gtgctggata gcgatggcag cttttttctg tatagcaaac tgaccgtgga taaaagccgc   1260
tggcagcagg gcaacgtgtt tagctgcagc gtgatgcatg aagcgctgca taaccattat   1320
acccagaaaa gcctgagcct gagcccgggc aaataa                              1356
```

<210> SEQ ID NO 12
<211> LENGTH: 1356
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody Trastuzumab (= Herceptin) -
      GC-optimized heavy chain

<400> SEQUENCE: 12

| | |
|---|---|
| gaggtgcagc tggtcgagag cggcggggc tcgtgcagc gggcgggtc gctgcggctg | 60 |
| agctgcgccg cgagcgggtt caacatcaag gacacctaca tccactgggt gcgccaggcc | 120 |
| cccggcaagg gcctcgagtg ggtcgcccgg atctacccca cgaacgggta caccccgctac | 180 |
| gccgacagcg tgaagggccg gttcaccatc agcgcggaca cctcgaagaa cacggcctac | 240 |
| ctgcagatga acagcctgcg cgccgaggac accgccgtgt actactgcag ccggtggggc | 300 |
| ggcgacgggt tctacgccat ggactactgg gggcagggca ccctcgtcac cgtgagcagc | 360 |
| gcgtcgacga aggggcccag cgtgttcccg ctggccccca gcagcaagag caccagcggc | 420 |
| gggaccgccg ccctgggctg cctcgtcaag gactacttcc ccgagcccgt gaccgtgtcg | 480 |
| tggaacagcg gcgcgctgac gagcggggtc cacaccttcc cggccgtgct gcagagcagc | 540 |
| ggcctctact cgctgagcag cgtggtcacc gtgcccagca gcagcctggg gacccagacg | 600 |
| tacatctgca acgtgaacca caagccctcg aacaccaagg tcgacaagaa ggtggagccc | 660 |
| ccgaagagct gcgacaagac ccacacctgc ccgccctgcc ccgcccccga gctcctgggc | 720 |
| gggcccagcg tgttcctgtt cccgcccaag cccaaggaca cgctcatgat cagccgcacc | 780 |
| cccgaggtca cctgcgtggt ggtcgacgtg agccacgagg accccgaggt gaagttcaac | 840 |
| tggtacgtcg acggcgtgga ggtgcacaac gccaagacca gccgcggga ggagcagtac | 900 |
| aactcgacgt accgcgtcgt gagcgtgctg accgtcctgc accaggactg gctcaacggc | 960 |
| aaggagtaca agtgcaaggt gagcaacaag gccctgcccg cgcccatcga gaagaccatc | 1020 |
| agcaaggcca aggggcagcc ccgggagccg caggtgtaca ccctgccccc cagccgcgac | 1080 |
| gagctcacga gaaccaggt cagcctgacc tgcctggtga agggcttcta ccctcggac | 1140 |
| atcgccgtgg agtgggagag caacgggcag ccggagaaca actacaagac cacccccgccc | 1200 |
| gtcctcgaca cgcgacggcag cttcttcctg tacagcaagc tgacggtgga caagtcgcgg | 1260 |
| tggcagcagg gcaacgtgtt cagctgcagc gtcatgcacg aggccctcca caaccactac | 1320 |
| acccagaaga gcctgagcct gagccccggg aagtga | 1356 |

```
<210> SEQ ID NO 13
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody Trastuzumab (= Herceptin) - wildtype,
      light chain

<400> SEQUENCE: 13
```

| | |
|---|---|
| gatattcaga tgacccagag cccgagcagc ctgagcgcga gcgtgggcga tcgcgtgacc | 60 |
| attacctgcc gcgcgagcca ggatgtgaac accgcggtgg cgtggtatca gcagaaaccg | 120 |
| ggcaaagcgc cgaaactgct gatttatagc gcgagctttc tgtatagcgg cgtgccgagc | 180 |
| cgctttagcg gcagccgcag cggcaccgat tttaccctga ccattagcag cctgcagccg | 240 |
| gaagattttg cgacctatta ttgccagcag cattatacca ccccgccgac ctttggccag | 300 |
| ggcaccaaag tggaaattaa acgcaccgtg gcggcgccag cgtgttat ttttccgccg | 360 |
| agcgatgaac agctgaaaag cggcaccgcg agcgtggtgt gcctgctgaa caacttttat | 420 |
| ccgcgcgaag cgaaagtgca gtggaaagtg ataacgcgc tgcagagcgg caacagccag | 480 |
| gaaagcgtga ccgaacagga tagcaaagat agcacctata gcctgagcag caccctgacc | 540 |
| ctgagcaaag cggattatga aaaacataaa gtgtatgcgt gcgaagtgac ccatcagggc | 600 | ctgagcagcc cggtgaccaa aagctttaac cgcggcgaat gctaa       645

<210> SEQ ID NO 14
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody Trastuzumab (= Herceptin) -
      GC-optimized light chain

<400> SEQUENCE: 14
gacatccaga tgacccagag cccgtcgagc ctgagcgcca gcgtgggcga ccgggtcacg       60
atcacctgcc gcgcgagcca ggacgtgaac accgccgtgg cctggtacca gcagaagccc      120
gggaaggccc ccaagctcct gatctactcg gcgagcttcc tgtacagcgg cgtccccagc      180
cggttcagcg gtcgcgcag cggcaccgac ttcacgctca ccatcagcag cctgcagccg       240
gaggacttcg ccacctacta ctgccagcag cactacacca cgcccccac cttcgggcag       300 ggcaccaagg tggagatcaa gcggaccgtg gccgccccca gcgtcttcat cttcccgccc      360
agcgacgagc agctgaagtc gggcacggcc agcgtggtgt gcctcctgaa caacttctac      420
ccccgcgagg cgaaggtcca gtggaaggtg acaacgcccc tgcagagcgg aacagccag       480 gagagcgtga ccgagcagga ctcgaaggac agcacctaca gcctcagcag caccctgacg      540
ctgagcaagg ccgactacga gaagcacaag gtctacgcct gcgaggtgac ccaccagggg      600
ctctcgagcc ccgtgaccaa gagcttcaac cggggcgagt gctga                     645

<210> SEQ ID NO 15
<211> LENGTH: 2295
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Antibody Trastuzumab (= Herceptin) - total
      construct with GC-optimized heavy und light chain

<400> SEQUENCE: 15
aagcttacca tggccgtgat ggcgccgcgg accctggtcc tcctgctgag cggcgccctc       60
gccctgacgc agacctgggc cggggaggtg cagctggtcg agagcggcgg gggcctcgtg      120
cagccgggcg gtcgctgcg gctgagctgc gccgcgagcg gttcaacat caaggacacc        180 tacatccact gggtgcgcca ggcccccggc aagggcctcg agtgggtcgc ccggatctac      240
cccacgaacg gtacaccccg ctacgccgac agcgtgaagg gccggttcac catcagcgcg      300
gacacctcga gaacacggc ctacctgcag atgaacagcc tgcgcgccga ggacaccgcc       360
gtgtactact gcagccggtg gggcggcgac gggttctacg ccatggacta ctgggggcag      420
ggcaccctcg tcaccgtgag cagcgcgtcg acgaagggc ccagcgtgtt cccgctggcc       480
cccagcagca gagcaccag cggcgggacc gccgccctgg gctgcctcgt caaggactac      540
ttccccgagc ccgtgaccgt gtcgtggaac agcggcgcg tgacgagcgg ggtccacacc       600
ttcccggccg tgctgcagag cagcggcctc tactcgctga gcagcgtggt caccgtgccc      660
agcagcagcc tggggaccca gacgtacatc tgcaacgtga accacaagcc ctcgaacacc      720
aaggtcgaca agaaggtgga gccccgaag agctgcgaca gacccacac ctgcccgccc        780

```
tgccccgccc ccgagctcct gggcgggccc agcgtgttcc tgttcccgcc caagcccaag    840
gacacgctca tgatcagccg cacccccgag gtcacctgcg tggtggtcga cgtgagccac    900
gaggaccccg aggtgaagtt caactggtac gtcgacggcg tggaggtgca acgccaag     960 accaagccgc gggaggagca gtacaactcg acgtaccgcg tcgtgagcgt gctgaccgtc   1020
ctgcaccagg actggctcaa cggcaaggag tacaagtgca aggtgagcaa caaggccctg   1080
cccgcgccca tcgagaagac catcagcaag gccaaggggc agccccggga gccgcaggtg   1140
tacaccctgc cccccagccg cgacgagctc acgaagaacc aggtcagcct gacctgcctg   1200
gtgaagggct tctaccccctc ggacatcgcc gtggagtggg agagcaacgg gcagccggag   1260
aacaactaca agaccacccc gcccgtcctc gacagcgacg gcagcttctt cctgtacagc   1320
aagctgacgg tggacaagtc gcggtggcag cagggcaacg tgttcagctg cagcgtcatg   1380
cacgaggccc tccacaacca ctacacccag aagagcctga gcctgagccc cgggaagcat   1440
catcatcatc atcattgacc agatctttct gacatttctg acatttctga catttctgac   1500
atttctgaca tttctgacat ttctgacatt tctgacattt ctgacatttc tgacatatgc   1560
ataccatggc cgtgatggcg ccgcggaccc tggtcctcct gctgagcggc gccctcgccc   1620
tgacgcagac ctgggccggg gacatccaga tgacccagag cccgtcgagc ctgagcgcca   1680
gcgtgggcga ccgggtcacg atcacctgcc gcgcgagcca ggacgtgaac accgccgtgg   1740
cctggtacca gcagaagccc gggaaggccc ccaagctcct gatctactcg gcgagcttcc   1800
tgtacagcgg cgtccccagc cggttcagcg gtcgcgcag cggcaccgac ttcacgctca   1860
ccatcagcag cctgcagccg gaggacttcg ccacctacta ctgccagcag cactacacca   1920
cgccccccac cttcgggcag ggcaccaagg tggagatcaa gcggaccgtg gccgccccca   1980
gcgtcttcat cttcccgccc agcgacgagc agctgaagtc gggcacggcc agcgtggtgt   2040
gcctcctgaa caacttctac ccccgcgagg cgaaggtcca gtggaaggtg gacaacgccc   2100
tgcagagcgg gaacagccag gagagcgtga ccgagcagga ctcgaaggac agcacctaca   2160
gcctcagcag cacccctgacg ctgagcaagg ccgactacga aagcacaag gtctacgcct   2220 gcgaggtgac ccaccagggg ctctcgagcc ccgtgaccaa gagcttcaac cggggcgagt   2280
gctgatgacc actag                                                   2295
```

<210> SEQ ID NO 16  
<211> LENGTH: 13  
<212> TYPE: RNA  
<213> ORGANISM: Artificial Sequence  
<220> FEATURE:  
<223> OTHER INFORMATION: Description of Artificial Sequence: Synthetic kozak-sequence oligonucleotide

<400> SEQUENCE: 16
gccgccacca ugg                                                      13

<210> SEQ ID NO 17  
<211> LENGTH: 15  
<212> TYPE: DNA  
<213> ORGANISM: Artificial Sequence  
<220> FEATURE:  
<223> OTHER INFORMATION: Description of Artificial Sequence: Synthetic generic stabilizing oligonucleotide  
<220> FEATURE:  
<223> OTHER INFORMATION: Description of Combined DNA/RNA Molecule: Synthetic generic stabilizing oligonucleotide  
<220> FEATURE:  
<221> NAME/KEY: modified_base  
<222> LOCATION: (1)..(1)

```
<223> OTHER INFORMATION: c or u
<220> FEATURE:
<221> NAME/KEY: modified_base
<222> LOCATION: (5)..(5)
<223> OTHER INFORMATION: a, c, u, g, unknown or other
<220> FEATURE:
<221> NAME/KEY: modified_base
<222> LOCATION: (9)..(9)
<223> OTHER INFORMATION: u or a
<220> FEATURE:
<221> NAME/KEY: modified_base
<222> LOCATION: (10)..(10)
<223> OTHER INFORMATION: Pyrimidine
<220> FEATURE:
<221> NAME/KEY: modified_base
<222> LOCATION: (13)..(13)
<223> OTHER INFORMATION: c or u
<220> FEATURE:
<223> OTHER INFORMATION: see specification as filed for detailed
      description of substitutions and preferred embodiments

<400> SEQUENCE: 17
nccancccnn ucncc                                                      15

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: localization sequence for the endoplasmic
      reticulum

<400> SEQUENCE: 18

Lys Asp Glu Leu
1

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: localization sequence for the endoplasmic
      reticulum

<400> SEQUENCE: 19

Asp Asp Glu Leu
1

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: localization sequence for the endoplasmic
      reticulum

<400> SEQUENCE: 20

Asp Glu Glu Leu
1

<210> SEQ ID NO 21
<211> LENGTH: 4
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: localization sequence for the endoplasmic
      reticulum

<400> SEQUENCE: 21

Gln Glu Asp Leu
1

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: localization sequence for the endoplasmic
      reticulum

<400> SEQUENCE: 22

Arg Asp Glu Leu
1

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: localization sequence for the nucleus

<400> SEQUENCE: 23

Pro Lys Lys Lys Arg Lys Val
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: localization sequence for the nucleus

<400> SEQUENCE: 24

Pro Gln Lys Lys Ile Lys Ser
1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: localization sequence for the nucleus

<400> SEQUENCE: 25

Gln Pro Lys Lys Pro
1               5
```

```
<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: localization sequence for the nucleus

<400> SEQUENCE: 26

Arg Lys Lys Arg
1

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: localization sequence for the nuclear region

<400> SEQUENCE: 27

Arg Lys Lys Arg Arg Gln Arg Arg Arg Ala His Gln
1               5                   10

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: localization sequence for the nuclear region

<400> SEQUENCE: 28

Arg Gln Ala Arg Arg Asn Arg Arg Arg Trp Arg Glu Arg Gln Arg
1               5                   10                  15

<210> SEQ ID NO 29
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: localization sequence for the nuclear region

<400> SEQUENCE: 29

Met Pro Leu Thr Arg Arg Arg Pro Ala Ala Ser Gln Ala Leu Ala Pro
1               5                   10                  15

Pro Thr Pro

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: localization sequence for the endosomal
      compartment

<400> SEQUENCE: 30
```

```
Met Asp Asp Gln Arg Asp Leu Ile Ser Asn Asn Glu Gln Leu Pro
1               5                   10                  15

<210> SEQ ID NO 31
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Myristoylation sequence, likalizing the
      antibody to the mitochondrial matrix
<220> FEATURE:
<221> NAME/KEY: MOD_RES
<222> LOCATION: (7)..(8)
<223> OTHER INFORMATION: Any naturally occurring amino acid
<220> FEATURE:
<221> NAME/KEY: MOD_RES
<222> LOCATION: (32)..(32)
<223> OTHER INFORMATION: Any naturally occurring amino acid

<400> SEQUENCE: 31

Met Leu Phe Asn Leu Arg Xaa Xaa Leu Asn Asn Ala Ala Phe Arg His
1               5                   10                  15

Gly His Asn Phe Met Val Arg Asn Phe Arg Cys Gly Gln Pro Leu Xaa
            20                  25                  30

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Sequence for localization of antibodies to the
      plasma membrane

<400> SEQUENCE: 32

Gly Cys Val Cys Ser Ser Asn Pro
1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Sequence for localization of antibodies to the
      plasma membrane

<400> SEQUENCE: 33

Gly Gln Thr Val Thr Thr Pro Leu
1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Sequence for localization of antibodies to the
      plasma membrane

<400> SEQUENCE: 34
```

Gly Gln Glu Leu Ser Gln His Glu
1               5

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Sequence for localization of antibodies to the
      plasma membrane

<400> SEQUENCE: 35

Gly Asn Ser Pro Ser Tyr Asn Pro
1               5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Sequence for localization of antibodies to the
      plasma membrane

<400> SEQUENCE: 36

Gly Val Ser Gly Ser Lys Gly Gln
1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Sequence for localization of antibodies to the
      plasma membrane

<400> SEQUENCE: 37

Gly Gln Thr Ile Thr Thr Pro Leu
1               5

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Sequence for localization of antibodies to the
      plasma membrane

<400> SEQUENCE: 38

Gly Gln Thr Leu Thr Thr Pro Leu
1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic

```
                  peptide
<220> FEATURE:
<223> OTHER INFORMATION: Sequence for localization of antibodies to the
      plasma membrane

<400> SEQUENCE: 39

Gly Gln Ile Phe Ser Arg Ser Ala
1               5

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Sequence for localization of antibodies to the
      plasma membrane

<400> SEQUENCE: 40

Gly Gln Ile His Gly Leu Ser Pro
1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Sequence for localization of antibodies to the
      plasma membrane

<400> SEQUENCE: 41

Gly Ala Arg Ala Ser Val Leu Ser
1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Sequence for localization of antibodies to the
      plasma membrane

<400> SEQUENCE: 42

Gly Cys Thr Leu Ser Ala Glu Glu
1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Sequence for localization of antibodies to the
      endoplasmic reticulum

<400> SEQUENCE: 43

Gly Gln Asn Leu Ser Thr Ser Asn
1               5
```

```
<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Sequence for localization of antibodies to the
      nucleus

<400> SEQUENCE: 44

Gly Ala Ala Leu Thr Ile Leu Val
1               5

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Sequence for localization of antibodies to the
      nucleus

<400> SEQUENCE: 45

Gly Ala Ala Leu Thr Leu Leu Gly
1               5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Sequence for localization of antibodies to the
      nucleus endoplasmic reticulum and the cytoplasma

<400> SEQUENCE: 46

Gly Ala Gln Val Ser Ser Gln Lys
1               5

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Sequence for localization of antibodies to the
      nucleus endoplasmic reticulum and the cytoplasma

<400> SEQUENCE: 47

Gly Ala Gln Leu Ser Arg Asn Thr
1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Sequence for localization of antibodies to the
      golgi apparatus, the nucleus, the cytoplasma and
      the cytoskeleton
```

<400> SEQUENCE: 48

Gly Asn Ala Ala Ala Ala Lys Lys
1               5

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Sequence for localization of antibodies to the
      cytoplasma and the cytoskeleton

<400> SEQUENCE: 49

Gly Asn Glu Ala Ser Tyr Pro Leu
1               5

<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Sequence for localization of antibodies to the
      plasma membrane and the cytoskeleton

<400> SEQUENCE: 50

Gly Ser Ser Lys Ser Lys Pro Lys
1               5

<210> SEQ ID NO 51
<211> LENGTH: 2269
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Alternative sequence of the construct of Fig.
      12 (antibody rituximab), wherein the restriction sites have been
      modified as compared to SEQ ID No. 5 of Fig. 12.

<400> SEQUENCE: 51
aagcttacca tggccgtgat ggcgccgcgg accctggtcc tcctgctgag cggcgccctc        60
gccctgacgc agacctgggc cgggcaggcc tacctgcagc agagcggcgc ggagctcgtg       120
cggccggggg cctcggtcaa gatgagctgc aaggccagcg gctacacctt cacgagctac       180
aacatgcact gggtgaagca gacccccgcg caggggctgg agtggatcgg cgccatctac       240
cccgggaacg gcgacaccag ctacaaccag aagttcaagg gcaaggcgac cctgacggtg       300
gacaagtcga gcagcaccgc ctacatgcag ctcagcagcc tgacctcgga ggacagcgcc       360
gtctacttct gcgcccgggt ggtgtactac agcaacagct actggtactt cgacgtctgg       420
gggaccggca cgaccgtgac cgtgagcggg cccagcgtct tccccctggc ccctcgagc        480 aagagcacca gcggcggcac ggcggccctc ggtgcctgg tgaaggacta cttccccgag        540
cccgtgaccg tcagctggaa ctcgggcgcc ctgaccagcg gggtgcacac cttcccggcc       600
gtgctccaga gcagcggcct gtacagcctg agctcggtcg tgacggtgcc cagcagcagc       660
ctcgggaccc agacctacat ctgcaacgtc aaccacaagc ccagcaacac caaggtggac       720

```
aagaaggcgg agcccaagtc gtgcgacaag acgcacacct gcccgccctg ccccgccccc      780
gagctgctgg gcggcccgag cgtgttcctc ttcccgccca gcccaagga cacccctgatg     840 atcagccgca cccccgaggt cacgtgcgtg gtggtcgacg tgagccacga ggaccccgag     900
gtgaagttca actggtacgt cgacggggtg gaggtgcaca cgccaagac caagcccgg       960 gaggagcagt acaacagcac ctaccgcgtc gtgagcgtgc tgaccgtcct ccaccaggac    1020
tggctgaacg gcaaggagta caagtgcaag gtgtcgaaca aggccctgcc ggcccccatc   1080
gagaagacga tcagcaaggc gaaggggcag ccccgggagc cccaggtgta caccctcccg   1140
cccagccgcg acgagctgac caagaaccag gtcagcctga cctgcctcgt gaagggcttc   1200
taccccagcg acatcgccgt ggagtgggag tcgaacgggc agcccgagaa caactacaag   1260 acgacccgc ccgtcctgga cagcgacggc agcttcttcc tgtacagcaa gctcaccgtg    1320
gacaagagcc ggtggcagca gggcaacgtg ttcagctgct cggtcatgca cgaggccctg    1380
cacaaccact acacccagaa gagcctgagc ctcagccccg ggaagcatca tcatcatcat   1440
cattgaccat gcatttctga catttctgac atttctgaca tttctgacat ttctgacatt    1500
tctgacattt ctgacatttc tgacatttct gacatttctg acatagatct accatggccg   1560
tgatggcgcc gcggaccctg gtcctcctgc tgagcggcgc cctcgccctg acgcagacct   1620
gggccgggca gatcgtgctg agccagtcgc cggccatcct cagcgcgagc cccggcgaga   1680
aggtcaccat gacgtgccgg gccagcagct cggtgagcta catgcactgg taccagcaga   1740
agcccgggag cagccccaag ccgtggatct acgcccccag caacctggcc tcgggcgtgc   1800
ccgcgcgctt cagcgggagc ggcagcggga ccagctacag cctgaccatc tcgcgggtcg   1860
aggccgagga cgccgccacc tactactgcc agcagtggag cttcaacccg cccacgttcg   1920 gcgcggcac caagctcgag ctgaagcgca ccgtggcggc cccagcgtg ttcatcttcc     1980 cgcccagcga cgagcagctg aagagcggga ccgcctcggt cgtgtgcctc ctgaacaact   2040 tctaccccg ggaggccaag gtgcagtgga aggtcgacaa cgcgctgcag agcggcaaca    2100
gccaggagag cgtgacggag caggacagca aggacagcac ctactcgctc agcagcaccc   2160
tgaccctgag caaggccgac tacgagaagc acaaggtgta cgcctgcgag gtcacgcacc   2220
aggggctcag ctcgcccgtg accaagagct tcaaccgctg accactagt              2269
```

<210> SEQ ID NO 52
<211> LENGTH: 2293
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Alternative sequence of the construct of Fig. 17 (antibody cetuximab), wherein the restriction sites have been modified as compared to SEQ ID No. 10 of Fig. 17.

<400> SEQUENCE: 52

```
aagcttacca tggccgtgat ggcgccgcgg accctggtcc tcctgctgag cggcgccctc      60
gccctgacgc agacctgggc cgggcaggtg cagctgaagc agagcggccc ggggctcgtc    120
cagccctcgc agagcctgag catcacctgc acggtgagcg gcttcagcct gaccaactac    180
ggggtgcact gggtccggca gtcgcccggc aaggggctcg agtggctggg cgtgatctgg    240
agcggcggga caccgactca aacccccc ttcacgagcc gcctgagcat caacaaggac      300
aacagcaagt cgcaggtgtt cttcaagatg aacagcctcc agagcaacga caccgccatc    360
```

```
tactactgcg cgcgggcect gacctactac gactacgagt tcgcctactg gggccagggg      420
accctggtca cggtgagcgc cgcgagcacc aagggcccga gcgtgttccc cctcgccccc      480
tcgagcaaga gcaccagcgg cgggaccgcc gccctgggct gcctggtcaa ggactacttc      540
cccgagccgg tgacggtgag ctggaactcg ggggccctca ccagcggcgt ccacaccttc      600
cccgcggtgc tgcagagcag cgggctgtac agcctcagct cggtggtcac cgtgcccagc      660
agcagcctgg gcacgcagac ctacatctgc aacgtgaacc acaagcccag caacaccaag      720
gtcgacaagc gcgtggagcc gaagtcgccc aagagctgcg acaagaccca cgtgcccg        780
ccctgccccg cccccgagct gctcggcggg cccagcgtgt tcctgttccc gcccaagccc      840
aaggacaccc tgatgatcag ccggacccc gaggtcacct gcgtggtggt cgacgtgagc       900
cacgaggacc cggaggtgaa gttcaactgg tacgtcgacg gcgtggaggt gcacaacgcc      960
aagacgaagc cccgcgagga gcagtacaac agcacctacc gggtcgtgtc ggtgctcacc     1020
gtcctgcacc aggactggct gaacgggaag gagtacaagt gcaaggtgag caacaaggcc     1080
ctccccgcgc ccatcgagaa gaccatcagc aaggccaagg ccagccgcg cgagccccag      1140
gtgtacacgc tgccccccag ccgggacgag ctgaccaaga accaggtcag cctcacctgc     1200
ctggtgaagg ggttctaccc gtcggacatc gccgtggagt gggagagcaa cggccagccc     1260
gagaacaact acaagaccac gcccccggtc ctggacagcg acggcagctt cttcctctac     1320
agcaagctga ccgtggacaa gagccgctgg cagcagggga cgtgttctc gtgcagcgtc      1380
atgcacgagg ccctgcacaa ccactacacc cagaagagcc tcagcctgag ccccggcaag     1440
catcatcatc atcatcattg accatgcatt tctgacattt ctgacatttc tgacatttct     1500
gacatttctg acatttctga catttctgac atttctgaca tttctgacat tctgacata     1560
gatctaccat ggccgtgatg gcgccgcgga ccctggtcct cctgctgagc ggcgccctcg     1620
ccctgacgca gacctgggcc ggggacatcc tgctcaccca gagcccggtg atcctgtcgg     1680
tcagccccgg cgagcgggtg agcttcagct gccgcgccag ccagtcgatc gggacgaaca     1740
tccactggta ccagcagcgg accaacggca gccccgcct gctcatcaag tacgcgagcg     1800
agagcatcag cgggatcccc tcgcggttca gcggcagcgg gagcggcacc gacttcaccc     1860
tgagcatcaa cagcgtggag tcggaggaca tcgccgacta ctactgccag cagaacaaca     1920
actggccgac gaccttcggc gccgggacca agctggagct caagcgcacc gtcgccgcgc     1980
ccagcgtgtt catcttcccg cccagcgacg agcagctgaa gagcggcacg gccagcgtgg     2040
tctgcctgct caacaacttc taccccgggg aggccaaggt gcagtggaag gtggacaacg     2100
ccctgcagtc ggggaacagc caggagagcg tcaccgagca ggacagcaag gacagcacct     2160
acagcctgtc gagcaccctc acgctgagca aggccgacta cgagaagcac aaggtgtacg     2220
cgtgcgaggt gacccaccag ggcctgagca gccccgtcac caagtcgttc aaccgcggcg     2280
cctgaccact agt                                                        2293
```

<210> SEQ ID NO 53
<211> LENGTH: 2295
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Alternative sequence of the construct of Fig. 22 (antibody trastuzumab), wherein the restriction sites have been modified as compared to SEQ ID No. 15 of Fig. 22.

<400> SEQUENCE: 53

```
aagcttacca tggccgtgat ggcgccgcgg accctggtcc tcctgctgag cggcgccctc    60
gccctgacgc agacctgggc cggggaggtg cagctggtcg agagcggcgg gggcctcgtg   120
cagccgggcg gtcgctgcg gctgagctgc gccgcgagcg ggttcaacat caaggacacc   180
tacatccact gggtgcgcca ggcccccggc aagggcctcg agtgggtcgc ccggatctac   240
cccacgaacg ggtacacccg ctacgccgac agcgtgaagg gccggttcac catcagcgcg   300
gacacctcga gaacacggc ctacctgcag atgaacagcc tgcgcgccga ggacaccgcc   360
gtgtactact gcagccggtg gggcggcgac gggttctacg ccatggacta ctggggggcag   420
ggcaccctcg tcaccgtgag cagcgcgtcg acgaaggggc ccagcgtgtt cccgctggcc   480
cccagcagca agagcaccag cggcgggacc gccgccctgg gctgcctcgt caaggactac   540
ttccccgagc ccgtgaccgt gtcgtggaac agcgcgcgc tgacgagcgg ggtccacacc   600
ttcccggccg tgctgcagag cagcggcctc tactcgctga gcagcgtggt caccgtgccc   660
agcagcagcc tggggaccca gacgtacatc tgcaacgtga accacaagcc ctcgaacacc   720
aaggtcgaca gaaggtgga gccccgaag agctgcgaca agaccacac ctgcccgccc   780
tgccccgccc ccgagctcct gggcgggccc agcgtgttcc tgttcccgcc caagcccaag   840
gacacgctca tgatcagccg cacccccgag gtcacctgcg tggtggtcga cgtgagccac   900
gaggacccg aggtgaagtt caactggtac gtcgacggcg tggaggtgca caacgccaag   960
accaagccgc gggaggagca gtacaactcg acgtaccgcg tcgtgagcgt gctgaccgtc  1020
ctgcaccagg actggctcaa cggcaaggag tacaagtgca aggtgagcaa caaggccctg  1080
cccgcgccca tcgagaagac catcagcaag gccaaggggc agccccggga gccgcaggtg  1140
tacaccctgc cccccagccg cgacgagctc acgaagaacc aggtcagcct gacctgcctg  1200
gtgaagggct tctacccctc ggacatcgcc gtggagtggg agagcaacgg gcagccggag  1260
aacaactaca agaccacccc gcccgtcctc gacagcgacg gcagcttctt cctgtacagc  1320
aagctgacgg tggacaagtc gcggtggcag cagggcaacg tgttcagctg cagcgtcatg  1380
cacgaggccc tccacaacca ctacacccag aagagcctga gcctgagccc cgggaagcat  1440
catcatcatc atcattgacc atgcatttct gacatttctg acatttctga catttctgac  1500
atttctgaca tttctgacat ttctgacatt tctgacattt ctgacatttc tgacatagat  1560
ctaccatggc cgtgatggcg ccgcggaccc tggtcctcct gctgagcggc gccctcgccc  1620
tgacgcagac ctgggccggg gacatccaga tgacccagag cccgtcgagc ctgagcgcca  1680
gcgtgggcga ccgggtcacg atcacctgcc gcgcgagcca ggacgtgaac accgccgtgg  1740
cctggtacca gcagaagccc gggaaggccc ccaagctcct gatctactcg gcgagcttcc  1800
tgtacagcgg cgtccccagc cggttcagcg gctcgcgcag cggcaccgac ttcacgctca  1860
ccatcagcag cctgcagccg gaggacttcg ccacctacta ctgccagcag cactacacca  1920
cgccccccac cttcgggcag ggcaccaagg tggagatcaa gcggaccgtg gccgccccca  1980
gcgtcttcat cttcccgccc agcgacgagc agctgaagtc gggcacggcc agcgtggtgt  2040
gcctcctgaa caacttctac ccccgcgagg cgaaggtcca gtggaaggtg gacaacgccc  2100
tgcagagcgg gaacagccag gagagcgtga ccgagcagga ctcgaaggac agcacctaca  2160
gcctcagcag cacccctgacg ctgagcaagg ccgactacga gaagcacaag gtctacgcct  2220
gcgaggtgac ccaccagggg ctctcgagcc ccgtgaccaa gagcttcaac cggggcgagt  2280
gctgatgacc actag                                                    2295
```

<210> SEQ ID NO 54
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(200)
<223> OTHER INFORMATION: This sequence may encompass 10 to 200 cytosine
      nucleotides, wherein some nucleotides may be absent
<220> FEATURE:
<223> OTHER INFORMATION: see specification as filed for detailed
      description of substitutions and preferred embodiments

<400> SEQUENCE: 54
cccccccccc cccccccccc cccccccccc cccccccccc cccccccccc cccccccccc      60
cccccccccc cccccccccc cccccccccc cccccccccc cccccccccc cccccccccc     120
cccccccccc cccccccccc cccccccccc cccccccccc cccccccccc cccccccccc     180
cccccccccc cccccccccc                                                 200

<210> SEQ ID NO 55
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(100)
<223> OTHER INFORMATION: This sequence may encompass 10 to 100 cytosine
      nucleotides, wherein some nucleotides may be absent
<220> FEATURE:
<223> OTHER INFORMATION: see specification as filed for detailed
      description of substitutions and preferred embodiments

<400> SEQUENCE: 55
cccccccccc cccccccccc cccccccccc cccccccccc cccccccccc cccccccccc      60
cccccccccc cccccccccc cccccccccc cccccccccc                           100

<210> SEQ ID NO 56
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(70)
<223> OTHER INFORMATION: This sequence may encompass 20 to 70 cytosine
      nucleotides, wherein some nucleotides may be absent
<220> FEATURE:
<223> OTHER INFORMATION: see specification as filed for detailed
      description of substitutions and preferred embodiments

<400> SEQUENCE: 56
cccccccccc cccccccccc cccccccccc cccccccccc cccccccccc cccccccccc      60
cccccccccc                                                             70

<210> SEQ ID NO 57
<211> LENGTH: 60
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(60)
<223> OTHER INFORMATION: This sequence may encompass 20 to 60 cytosine
      nucleotides, wherein some nucleotides may be absent
<220> FEATURE:
<223> OTHER INFORMATION: see specification as filed for detailed
      description of substitutions and preferred embodiments

<400> SEQUENCE: 57
cccccccccc cccccccccc cccccccccc cccccccccc cccccccccc cccccccccc    60

<210> SEQ ID NO 58
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(40)
<223> OTHER INFORMATION: This sequence may encompass 10 to 40 cytosine
      nucleotides, wherein some nucleotides may be absent
<220> FEATURE:
<223> OTHER INFORMATION: see specification as filed for detailed
      description of substitutions and preferred embodiments

<400> SEQUENCE: 58
cccccccccc cccccccccc cccccccccc cccccccccc                          40

<210> SEQ ID NO 59
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 59

His His His His His His
1               5

<210> SEQ ID NO 60
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
catcatcatc atcatcat                                                  18

<210> SEQ ID NO 61
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
atggccgtga tggcgccgcg gaccctggtc ctcctgctga gcggcgccct cgccctgacg    60
cagacctggg ccggg                                                     75
```

```
<210> SEQ ID NO 62
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(200)
<223> OTHER INFORMATION: This sequence may encompass 10 to 200 adenosine
      nucleotides, wherein some nucleotides may be absent
<220> FEATURE:
<223> OTHER INFORMATION: see specification as filed for detailed
      description of substitutions and preferred embodiments

<400> SEQUENCE: 62
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180
aaaaaaaaaa aaaaaaaaaa                                                 200
```